(12) United States Patent
Meng

(10) Patent No.: US 8,426,460 B2
(45) Date of Patent: Apr. 23, 2013

(54) DIMERIC AVERMECTIN AND MILBEMYCIN DERIVATIVES

(75) Inventor: Charles Q. Meng, Johns Creek, GA (US)

(73) Assignee: Merial Limited, Duluth, GA (US)

( * ) Notice: Subject to any disclaimer, the term of this patent is extended or adjusted under 35 U.S.C. 154(b) by 34 days.

(21) Appl. No.: 12/631,249

(22) Filed: Dec. 4, 2009

(65) Prior Publication Data
US 2010/0144859 A1 Jun. 10, 2010

Related U.S. Application Data

(60) Provisional application No. 61/119,761, filed on Dec. 4, 2008.

(51) Int. Cl.
*A61K 31/35* (2006.01)
(52) U.S. Cl.
USPC .......................................................... 514/456
(58) Field of Classification Search .................... None
See application file for complete search history.

(56) References Cited

FOREIGN PATENT DOCUMENTS

JP 10017568 A2 1/1998
JP 10-17568 * 10/1998

OTHER PUBLICATIONS

Sato et al Machine Translation.*
STN Search Report (Accession No. 2007:1348019 containing summary of CN 101074253 (published Nov. 21, 2001).*
Patani et al (Chem Rev 96:3147-3176, 1996).*
Zakson-Aiken et al (J Med Entomol 38(4):576-580, 2001—Abstract only).*

* cited by examiner

*Primary Examiner* — Craig Ricci
(74) *Attorney, Agent, or Firm* — Judy Jarecki-Black; John Ezcurra; Merial Limited

(57) ABSTRACT

This invention provides for novel antiparasitic and pesticidal derivatives of avermectin and milbemycin compounds in which two avermectin or milbemycin members are linked together by a chemical linker. The resulting compounds may be used in veterinary compositions which are used in treating, controlling and preventing of endo- and ectoparasite infections and infestations in animals or for combating pests in plants or plant propagation material.

19 Claims, No Drawings

DIMERIC AVERMECTIN AND MILBEMYCIN DERIVATIVES

CROSS REFERENCE TO RELATED APPLICATIONS

This application claims the benefit of priority to U.S. Provisional Patent Application No. 61/119,761, filed on Dec. 4, 2008, which is incorporated herein by reference in its entirety.

FIELD OF THE INVENTION

This invention provides for novel antiparasitic derivatives of the avermectin and milbemycin families in which two avermectin or milbemycin molecules are linked by a chemical linker. The resulting compounds may be used in oral, parental or topical veterinary formulations for treating, controlling and preventing of endo- and ectoparasite infections/infestations in mammals, such as horses, cattle, sheep, swine, dogs, cats and humans, as well as birds and fish.

BACKGROUND OF THE INVENTION

Animals and humans suffer from endoparasitical infections including, for example, helminthiasis which is most frequently caused by a group of parasitic worms described as nematodes or roundworms. These parasites cause severe economic losses in pigs, sheep, horses, and cattle as well as poultry. Parasites which occur in the gastrointestinal tract of animals and humans include those of the genera *Ancylostoma, Necator, Ascaris, Strongyloides, Trichinella, Capillaria, Toxocara, Toxascaris, Trichuris, Enterobius, Haemonchus, Ostergagia, Trichostrongylus, Oesophagostomum, Cooperia, Bunostomum, Strongylus, Cyathostomum* and parasites which are found in the blood or other tissues and organs such as *Dirofileria, Onchocerca, Dictyocaulus*.

Macrolide anthelmintic compounds may be used for treating endo- and ectoparasite infections and infestations in mammals and birds. Compounds that belong to this class include the avermectin and milbemycin series of macrolides. These compounds are potent antiparasitic agents that are effective against a wide range of internal and external parasites. Avermectins and milbemycins share the same common 16-membered macrocyclic lactone ring; however, milbemycins do not possess the disaccharide substituent on the 13-position of the lactone ring. In addition to treating parasitic insects, ticks and mites, avermectins and milbemycins are used to treat endoparasite infections in warm-blooded animals.

The avermectins may be isolated from the fermentation broth of an avermectin producing strain of *Streptomyces avermitilis* and derivatives thereof. The production, isolation and structural determination of the avermectins are documented in Albers-Schonberg, et. al, *J. Am. Chem. Soc.* 1981, 103, 4216-4221 and references cited therein. The description of the morphological characteristics of the culture is described in U.S. Pat. No. 4,310,519, which is incorporated herein by reference. The eight different naturally occurring avermectins have the following structures:

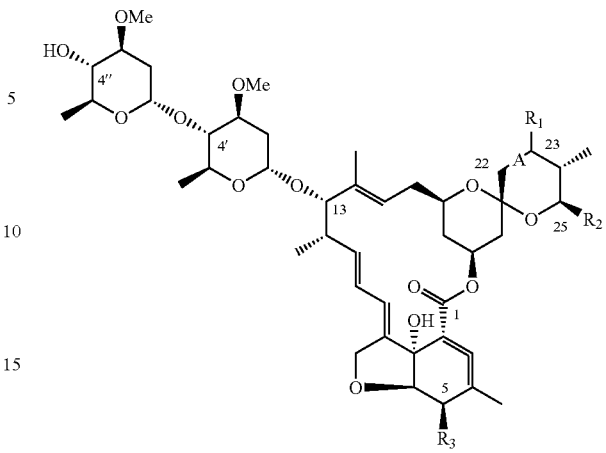

wherein A at the 22,23 position indicates a single or a double bond; $R_1$ is hydrogen or hydroxyl; $R_2$ is iso-propyl or sec-butyl; and $R_3$ is hydroxy or methoxy. Conventional differentiation of the naturally occurring congeners is denoted as follows:

| congener | (A) | $R_1$ | $R_2$ | $R_3$ |
|---|---|---|---|---|
| A1a | double bond | —H | sec-butyl | —OCH$_3$ |
| A1b | double bond | —H | iso-propyl | —OCH$_3$ |
| A2a | single bond | —OH | sec-butyl | —OCH$_3$ |
| A2b | single bond | —OH | iso-propyl | —OCH$_3$ |
| B1a | double bond | —H | sec-butyl | —OH |
| B1b | double bond | —H | iso-propyl | —OH |
| B2a | single bond | —OH | sec-butyl | —OH |
| B2b | single bond | —OH | iso-propyl | —OH |

Isolation of the avermectins generally provides a mixture of the "a" and "b" components in a ratio of 4:1, respectively. Separation of the "a" and "b" components can be achieved via standard chromatographic techniques, however this is seldom done in practice as the minimal differences in the $R_2$ substituents of these derivatives confer little effect on chemical reactivity or biological activity of the compounds. Thus, the presence of the mixture is indicated by referring to the congeners as A1, A2, B1, or B2 while omitting the "a" and "b" designation.

The milbemycins are the aglycone derivatives of the avermectins, such as those described, for example in U.S. Pat. Nos. 4,144,352; 4,791,134; and 6,653,342, which are incorporated herein by reference. Particularly important anthelmintics of this family include moxidectin, as described, for example in U.S. Pat. Nos. 7,348,417; and 4,916,154 (and references cited therein, all incorporated herein by reference).

The avermectin and milbemycin series of compounds either are natural products or are semi-synthetic derivatives. The natural product avermectins are disclosed in U.S. Pat. No. 4,310,519, and the 22,23-dihydro avermectin compounds are disclosed in U.S. Pat. No. 4,199,569, all of which are incorporated herein by reference. The synthesis of avermectins has been documented (*J. Am. Chem. Soc.* 1989, 111, 2967; *J. Am. Chem. Soc.* 1986, 108, 2776) and research on deconjugation and epimerization of avermectin derivatives is also described in Hanessian, et al (*J. Am. Chem. Soc.* 1987, 109, 7063) and Fraser-Reid, et al (*J. Am. Chem. Soc.* 1987, 109, 933). For a general discussion of avermectins, which includes a discussion of their uses in humans and animals, see "Ivermectin and Abamectin," W. C. Campbell, ed., Springer-Verlag, New York (1989). Naturally occurring milbemycins are described in Aoki et al., U.S. Pat. No. 3,950,360 as well as in the various references cited in "The Merck Index" 12$^{th}$ ed., S. Budavari, Ed., Merck & Co., Inc. Whitehouse Station, New Jersey (1996).

Examples of avermectins include abamectin, dimadectin, doramectin, emamectin, eprinomectin, ivermectin, latidectin, lepimectin, and selamectin. Examples of milbemycins include milbemectin, milbemycin D, moxidectin and nemadectin. Also included are the 5-oxo and 5-oxime derivatives of said avermectins and milbemycins, respectively.

The macrocyclic lactone compounds are known in the art and can easily be obtained commercially or through synthesis techniques known in the art. Reference is made to the widely available technical and commercial literature. For avermectins, such as ivermectin and abamectin, reference may be made, for example, to the work "Ivermectin and Abamectin", 1989, by M. H. Fischer and H. Mrozik, William C. Campbell, published by Springer Verlag., or Albers-Schönberg et al. (1981), "Avermectins Structure Determination", *J. Am. Chem. Soc.*, 103, 4216-4221. For doramectin, *"Veterinary Parasitology"*, vol. 49, No. 1, July 1993, 5-15 may be consulted. For milbemycins, reference may be made, inter alia, to Davies H. G. et al., 1986, "Avermectins and Milbemycins", *Nat. Prod. Rep.*, 3, 87-121, Mrozik H. et al., 1983, Synthesis of Milbemycins from Avermectins, *Tetrahedron Lett.*, 24, 5333-5336, U.S. Pat. No. 4,134,973 and EP 0 677 054.

The avermectins and milbemycins demonstrate potent antiparasitic activity while being relatively non-toxic to most mammalian species. As a result, the avermectin/milbemycin family has been the focus of extensive chemical modification studies, which are outlined, for example, in U.S. Pat. Nos. 4,199,569; 4,310,519; 4,423,209; 4,427,663; 4,457,920; 4,806,527; 4,831,016; 4,855,317; 4,859,657; 4,871,719; 4,873,224; 4,874,749; 4,895,837; 4,906,619, 4,920,148; 4,963,582; 4,973,711; 4,978,677; 5,015,630, 5,023,241; 5,030,622; 5,055,454; 5,055,596; 5,057,499; 5,077,308; 5,162,363; 5,169,839; 5,208,222; 5,244,879; 5,262,400; 5,830,875; and 7,250,402. Chemical modifications have also been induced via spiking the fermentation broth with acids, which are subsequently incorporated at the C-25 position of the avermectins (EP 0 214 731, and *Arch. Biochem. Biophys* 1989, 269, 544-547). All of these documents and references cited therein, as well as the references cited herein, are expressly incorporated by reference.

Notwithstanding the excellent progress in antiparasitic research, concerns remain with respect to increasingly common reports of resistance among veterinary parasites (*Parasitology* 2005, 131, S179-190). Thus, there remains an ongoing need for novel endectocides and anthelmintic treatments in veterinary medicine. It is an object of this invention to provide novel endectocides and anthelmintic compounds and formulations, as well as methods of treatment using such compounds. That the invention performs as herein described is surprising, unexpected and non obvious.

All documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

Citation or identification of any document in this application does not constitute an admission that such document is available a prior art to the present invention.

SUMMARY OF THE INVENTION

The instant invention provides for, inter alia, novel dimeric avermectin/milbemycin compounds, compositions and uses thereof, wherein the 13-, 4'- or 4"-positions of two monomeric avermectin or milbemycin derivatives may be joined via a chemical linker. These compounds may be further substituted at the 4-, 5-, 23-, and 25-positions. Thus, it is an object of the invention to describe such compounds.

One object of the invention is to provide a compound of formula (I):

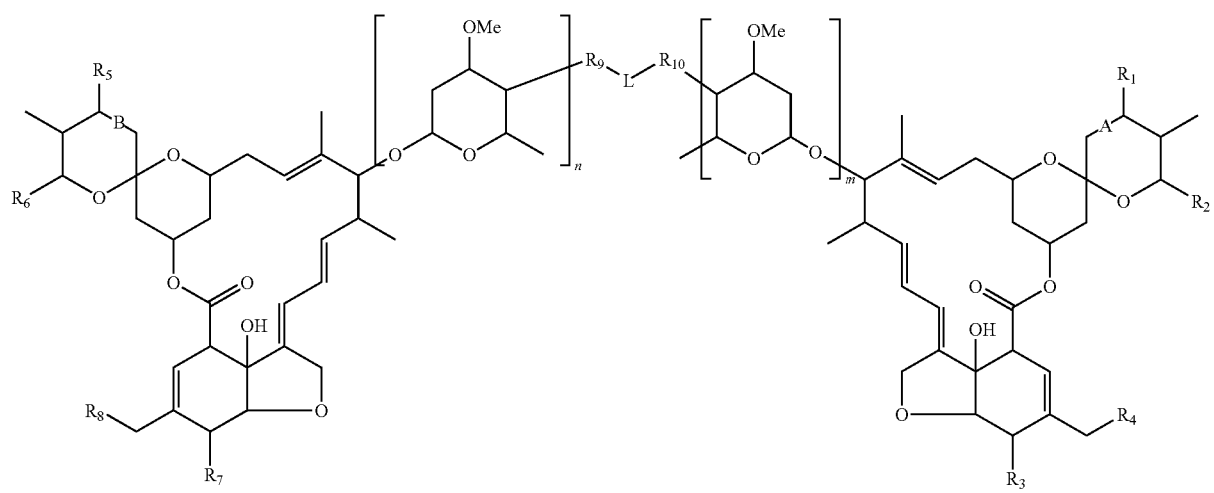

wherein:

A is a single or double bond;

B is a single or double bond;

$R_1$ and $R_5$ are independently hydrogen, hydroxyl, oxo, oximino or alkoxyimino, provided that $R_1$ is hydroxyl only when A is a single bond, and that $R_5$ is hydroxyl only when B is a single bond;

$R_2$ and $R_6$ are independently linear or branched $C_1$-$C_8$ alkyl, $C_2$-$C_8$ alkenyl, or $C_3$-$C_8$ cycloalkyl;

$R_3$ and $R_7$ are independently hydroxyl, methoxy, oxo, hydroximino, or alkoxyimino;

$R_4$ and $R_8$ are independently hydrogen, hydroxyl, $C_1$-$C_8$ alkanoyloxy, benzoyloxy, di-$C_1$-$C_8$ alkylamino benzoyloxy, $(C_1$-$C_8$ alkoxy$)_p$, $C_1$-$C_8$ alkylthio, $C_1$-$C_8$ alkylthioalkoxy or oleandrosyloxy;

$R_9$ and $R_{10}$ are independently diradical groups selected from a bond, O, $NR_{11}$, —$NR_{11}C(\!=\!O)$—, —$NR_{11}C(\!=\!S)$—, —$NR_{11}C(\!=\!O)O$—, —$ONR_{11}C(\!=\!O)$—, —$ONR_{11}C(\!=\!O)O$—, —$ONR_{11}C(\!=\!O)NR_{11}$—, —$OC(\!=\!O)O$—, —$N(R_{11})C(\!=\!O)N(R_{11})$—, —$N(R_{11})C(\!=\!S)N(R_{11})$—, —$N(R_{11})S(O)_2N(R_{11})$—, —$N(R_{11})S(O)_2$—, —$N(R_{11})SON(R_{11})$—, —$N(R_{11})S(O)$—, —$C(\!=\!NR_{11})$—, —$C(\!=\!O)$—, —$C(\!=\!O)N(R_{11})$—, and —$C(\!=\!S)N(R_{11})$—;

$R_{11}$ is H or $R_2$;

L is a diradical linker selected from a bond, $C_1$-$C_{20}$ alkylene, $C_2$-$C_{20}$ alkenylene, $C_2$-$C_{20}$ alkynylene, $C_3$-$C_8$ cycloalkylene, arylene, aryloxy arylene, heteroarylene, or any combination thereof, which may optionally contain a N, O, S, P, or Si atom; and wherein said linker may optionally be substituted with one or more groups selected from cyano, nitro, hydroxy, halogen, O, N, S, $C_1$-$C_6$ alkyl, $C_3$-$C_8$ cycloalkyl, $C_1$-$C_6$ alkoxy, $C_1$-$C_6$ thioalkyl, oxo, oximino, and alkoxyimino; m and n are independently 0, 1, or 2; and p is 1-3. The linker L in the compounds of formula (I) may connect the two macrocyclic lactone monomers at any carbon atom in the chain or through any two atoms in a ring linker. For example, when the linker is a phenylene group, the two monomers may be substituted to the phenylene linker in an ortho-, meta- or para-relationship to each other. Similarly, when the linker is an alkylene chain, the two macrocylic lactone monomers may be connected to any two atoms of the linker chain, including internal atoms as well as the terminal atoms in the alkylene chain.

Further, this invention provides for antiparasitic compositions comprising the compounds of formula (I), non-limiting examples of which may include spot-on and pour-on formulations and formulations for oral and injectable administration. Thus, a second object of this invention is to provide antiparasitic compositions comprising the compounds of formula (I) for the prevention and treatment of parasitic infections and infestations in an animal.

Another object of the invention is to provide compositions for combating pests that are harmful to plants, plant propagation material or material derived from wood.

A third object of this invention is to provide methods of treatment and prevention of parasitic infections or infestations of animals, which comprise treating the infected animal with an effective antiparasitic amount of a compound of formula (I).

A fourth object of this invention is to provide methods for combating pests on plants, plant propagation material or material derived from wood, which comprises treating the infected plant, or the soil in which the infected plant grows, or the wood-derived material with a pesticidally effective amount of a compound of formula (I).

It is noted that the invention does not intend to encompass within the scope of the invention any previously disclosed compound, product, process of making the product or method of using the product, which meets the written description and enablement requirements of the USPTO (35 U.S.C. 112, first paragraph) or the EPO (Article 83 of the EPC), such that the applicant(s) reserve the right and hereby disclose a disclaimer of any previously described product, method of making the product or process of using the product. It is therefore an intention of the invention to not explicitly cover compounds, products, processes of making products or compounds, or methods of using products or compounds that are explicitly disclosed in the prior art or whose novelty is destroyed by prior art, including without limitation any prior art herein mentioned; and the applicant(s) explicitly reserve the right to introduce into any claim a disclaimer as to any previously disclosed compound, product, process of making the product or method of using the product. Specifically, the compounds of the invention are not intended to encompass avermectin/milbemycin or previously disclosed derivatives of avermectin/milbemycin.

These and other embodiments are disclosed or are obvious from and encompassed by, the following Detailed Description.

DETAILED DESCRIPTION

The compounds of the invention and compositions comprising the compounds are highly effective for the treatment or prevention of parasitic infections or infestations in or on mammals, fish and birds, and in particular, humans, cats, dogs, horses, chickens, pigs, sheep and cattle with the aim of ridding these hosts of all the parasites commonly encountered by mammals, fish and birds.

The compounds and compositions of the invention are also active against pests that damage agricultural material, and may be effectively used to treat and protect plants, crops, plant propagation material, property containing wood or derived from wood, from harmful pests.

Accordingly, the present invention provides methods for preventing and treating parasites in or on animals, comprising administering a parasiticidally effective amount of a compound of formula (I), or a pharmaceutically acceptable salt thereof, to the animal. The invention also provides a method for combating or controlling pests and for protecting crops, growing plants, plant propagation material, and wood-containing material, or material derived from wood, from infestation by pests, comprising contacting the pests, crops, plants, plant propagation material, or the soil or water in which the plants is growing, or the wood-containing material or material derived from wood, with a pesticidally effective amount of a compound of formula (I), or an agriculturally acceptable salt thereof.

As used herein, the following terms have the meanings ascribed to them unless specified otherwise. In this disclosure and in the claims, terms such as "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Unless otherwise specifically noted or apparent by context, "active agent" or "active ingredient" or "therapeutic agent" as used in this specification, means a dimeric avermectin or dimeric milbemycin, compound of the invention It is also noted that in this disclosure and the appended claims and/or paragraphs, the term "dimeric avermectin", "dimeric milbemycin", or "dimeric avermectin/milbemycin" as used to describe the invention is intended to include all stereoisomers and crystalline forms (which include hydrated forms, polymorphic forms and amorphous forms) thereof.

The compounds of the instant invention have the following structural formula (I):

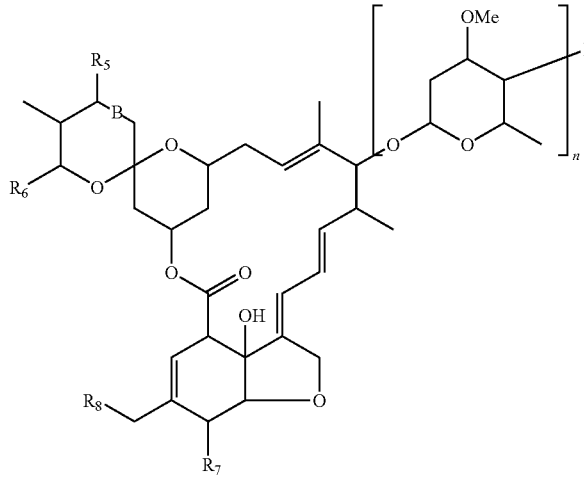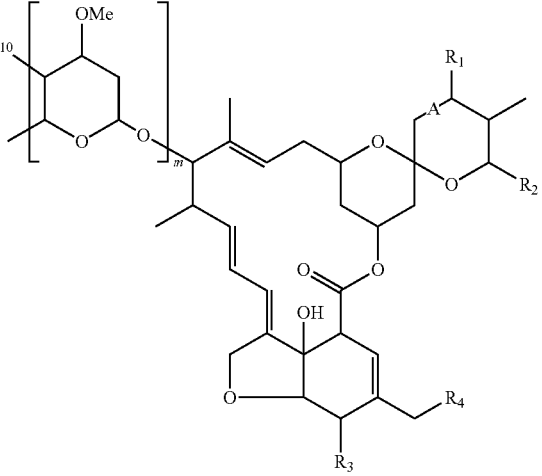

(I)

wherein:
A is a single or double bond;
B is a single or double bond;
$R_1$ and $R_5$ are independently hydrogen, hydroxyl, oxo, oximino or alkoxyimino, provided that $R_1$ is hydroxyl only when A is a single bond, and that $R_5$ is hydroxyl only when B is a single bond;
$R_2$ and $R_6$ are independently linear or branched $C_1$-$C_8$ alkyl, $C_2$-$C_8$ alkenyl, or $C_3$-$C_8$ cycloalkyl;
$R_3$ and $R_7$ are independently hydroxyl, methoxy, oxo, hydroximino, or alkoxyimino;
$R_4$ and $R_8$ are independently hydrogen, hydroxyl, $C_1$-$C_8$ alkanoyloxy, benzoyloxy, di-$C_1$-$C_8$ alkylamino benzoyloxy, ($C_1$-$C_8$ alkoxy)$_p$, $C_1$-$C_8$ alkylthio, $C_1$-$C_8$ alkylthioalkoxy and oleandrosyloxy;
$R_9$ and $R_{10}$ are independently diradical groups selected from a bond, O, $NR_{11}$, —$NR_{11}C(=O)$—, —$NR_{11}C(=S)$—, —$NR_{11}C(=O)O$—, —$ONR_{11}C(=O)$—, —$ONR_{11}C(=O)O$—, —$ONR_{11}C(=O)NR_{11}$—, —$OC(=O)O$—, —$N(R_{11})C(=O)N(R_{11})$—, —$N(R_{11})C(=S)N(R_{11})$—, —$N(R_{11})S(O)_2N(R_{11})$—, —$N(R_{11})S(O)_2$—, —$N(R_{11})SON(R_{11})$—, —$N(R_{11})S(O)$—, —$C(=NR_{11})$—, —$C(=O)$—, —$C(=O)N(R_{11})$—, and —$C(=S)N(R_{11})$—;
$R_{11}$ is H or $R_2$;
L is a diradical linker selected from a bond, $C_1$-$C_{20}$ alkylene, $C_2$-$C_{20}$ alkenylene, $C_2$-$C_{20}$ alkynylene, $C_3$-$C_8$ cycloalkylene, arylene, aryloxy arylene, heteroarylene, and any combination thereof, which may optionally contain a N, O, S, P, or Si atom;
wherein said linker may optionally be substituted with one or more of cyano, nitro, hydroxy, halogen, O, N, S, $C_1$-$C_6$ alkyl, $C_3$-$C_8$ cycloalkyl, $C_1$-$C_6$ alkoxy, $C_1$-$C_6$ thioalkyl, oxo, oximino, or alkoxyimino;
m and n are independently 0, 1, or 2; and
p is 1-3;
or pharmaceutically acceptable salts thereof; wherein $R_9$ and $R_{10}$ may be connected to any two atoms of linker L.

In one embodiment of formula (I), L is $C_1$-$C_{12}$alkylene or arylene.

In another embodiment of formula (I), L is $C_2$-$C_6$alkylene.

In another embodiment, the invention provides for a compound of formula (I) wherein: $R_9$ and $R_{10}$ are independently nitrogen or oxygen and $R_1$, $R_5$, $R_2$, $R_6$, $R_3$, $R_4$, $R_7$, $R_8$, L, A, B, n and m are as defined above.

In another embodiment, the invention provides for a compound of formula (I) wherein $R_9$ and $R_{10}$ are independently oxygen or nitrogen; L is a $C_2$-$C_{20}$ alkylene linker; and $R_1$, $R_5$, $R_2$, $R_6$, $R_3$, $R_4$, $R_7$, $R_8$, A, B, n and m are as defined above.

In still another embodiment, the invention provides a compound of formula (I) wherein $R_9$ and $R_{10}$ are independently —$OC(=O)O$—, —$N(R_{11}S(O)_2N(R_{11})$—, —$N(R_{11}S(O)_2$—, —$NR_{11}C(=O)O$—, —$NR_{11}C(=O)NR_{11}$—, —$ONR_{11}C(=O)$—, —$ONR_{11}C(=O)O$— or —$ONR_{11}C(=O)NR_{11}$—; L is a $C_2$-$C_8$alkylene linker; and $R_1$, $R_5$, $R_2$, $R_6$, $R_3$, $R_4$, $R_7$, $R_8$, A, B, n and m are as defined above.

In still another embodiment, the invention provides for a compound of formula (I) wherein:
$R_1$ and $R_5$ are hydrogen;
$R_2$ and $R_6$ are independently isopropyl, sec-butyl or cyclohexyl;
$R_3$ and $R_7$ are independently hydroxyl, methoxy or hydroximino;
$R_4$ and $R_8$ are hydrogen;
$R_9$ and $R_{10}$ are independently oxygen, $NR_{11}$, —$ONR_{11}C(=O)$—, —$ONR_{11}C(=O)NR_{11}$—, —$ONR_{11}C(=O)O$—, —$NR_{11}C(=O)NR_{11}$—, —$NR_{11}C(=O)O$—, —$N(R_{11})S(O)_2N(R_{11})$—, —$N(R_{11})S(O)_2$—, —$NR_{11}C(=O)$— or —$OC(=O)O$—;
L is a $C_2$-$C_{20}$ alkylene linker; and
m and n are 2.

In another embodiment, the invention provides for a compound of formula (I) wherein:
$R_1$ and $R_5$ are hydrogen;
$R_2$ and $R_6$ are independently isopropyl, sec-butyl or cyclohexyl;
$R_3$ and $R_7$ are independently hydroxyl, methoxy or hydroximino;
$R_4$ and $R_8$ are hydrogen;
$R_9$ and $R_{10}$ are independently —$ONR_{11}C(=O)$—, —$ONR_{11}C(=O)NR_{11}$—, —$ONR_{11}C(=O)O$—, —$NR_{11}C(=O)NR_{11}$—, or —$NR_{11}C(=O)O$—;
L is a $C_2$-$C_{20}$ alkylene linker; and
m and n are 2.

In still another embodiment, the invention provides for a compound of formula (I) wherein:

$R_1$ and $R_5$ are hydrogen;
$R_2$ and $R_6$ are independently isopropyl, sec-butyl or cyclohexyl;
$R_3$ and $R_7$ are independently hydroxyl, methoxy or hydroximino;
$R_4$ and $R_8$ are hydrogen;
$R_9$ and $R_{10}$ are independently —N($R_{11}$S(O)$_2$N($R_{11}$)—, —N($R_{11}$S(O)$_2$—, —NR$_{11}$C(=O)— or —OC(=O)O—;
L is a $C_2$-$C_{20}$ alkylene linker; and
m and n are 2.

Another embodiment provides for a compound of formula (I) wherein:
A is a single bond;
B is a single bond;
$R_1$ and $R_5$ are hydrogen;
$R_2$ and $R_6$ are cyclohexyl;
$R_3$ and $R_7$ are hydroximino;
$R_4$ and $R_8$ are hydrogen;
$R_9$ and $R_{10}$ are oxygen or $NR_{11}$;
L is a $C_2$-$C_{20}$ alkyl linker; and
m and n are 1.

In another embodiment the invention provides for a compound of formula (I) wherein:
A is a single bond;
B is a single bond;
$R_1$ and $R_5$ are hydrogen;
$R_2$ and $R_6$ are cyclohexyl;
$R_3$ and $R_7$ are hydroximino;
$R_4$ and $R_8$ are hydrogen;
$R_9$ and $R_{10}$ are independently —ONR$_{11}$C(=O)—, —ONR$_{11}$C(=O)NR$_{11}$—, —ONR$_{11}$C(=O)O—, —NR$_{11}$C(=O)NR$_{11}$—, or —NR$_{11}$C(=O)O—;
L is a $C_2$-$C_{20}$ alkyl linker; and
m and n are 1.

Another embodiment provides for a compound of formula (I) wherein:
A is a single bond;
B is a single bond;
$R_1$ and $R_5$ are hydrogen;
$R_2$ and $R_6$ are cyclohexyl;
$R_3$ and $R_7$ are hydroximino;
$R_4$ and $R_8$ are hydrogen;
$R_9$ and $R_{10}$ are independently —N($R_{11}$S(O)$_2$N($R_{11}$)—, —N($R_{11}$S(O)$_2$—, —NR$_{11}$C(=O)— or —OC(=O)O—;
L is a $C_2$-$C_{20}$ alkyl linker; and
m and n are 1.

Another embodiment of the invention provides for a compound of formula (I) wherein:
A is a single bond;
B is a single bond;
$R_1$ and $R_5$ are independently H, OH or alkoxyimino;
$R_2$ and $R_6$ are branched $C_2$-$C_8$ alkenyl;
$R_3$ and $R_7$ are hydroxyl;
$R_4$ and $R_8$ are hydrogen;
$R_9$ and $R_{10}$ are independently oxygen or $NR_{11}$;
L is a $C_2$-$C_{20}$ alkyl linker; and
m and n are 0.

In another embodiment the invention provides for a compound of formula (I) wherein:
A is a single bond;
B is a single bond;
$R_1$ and $R_5$ are independently H, OH or alkoxyimino;
$R_2$ and $R_6$ are branched $C_2$-$C_8$ alkenyl;
$R_3$ and $R_7$ are hydroxyl;
$R_4$ and $R_8$ are hydrogen;
$R_9$ and $R_{10}$ are independently —ONR$_{11}$C(=O)—, —ONR$_{11}$C(=O)NR$_{11}$—, —ONR$_{11}$C(=O)O—, —NR$_{11}$C(=O)NR$_{11}$—, or —NR$_{11}$C(=O)O—;
L is a $C_2$-$C_{20}$ alkyl linker; and
m and n are 0.

In still another embodiment, the invention provides for a compound of formula (I) wherein:
A is a single bond;
B is a single bond;
$R_1$ and $R_5$ are independently H, OH or alkoxyimino;
$R_2$ and $R_6$ are branched $C_2$-$C_8$ alkenyl;
$R_3$ and $R_7$ are hydroxyl;
$R_4$ and $R_8$ are hydrogen;
$R_9$ and $R_{10}$ are independently —N($R_{11}$S(O)$_2$N($R_{11}$)—, —N($R_{11}$S(O)$_2$—, —NR$_{11}$C(=O)— or —OC(=O)O—;
L is a $C_2$-$C_{20}$ alkyl linker; and
m and n are 0.

Another embodiment provides for a compound of formula (I) wherein:
$R_2$ and $R_6$ are independently linear or branched $C_1$-$C_8$ alkyl, $C_2$-$C_8$ alkenyl, or $C_3$-$C_8$ cycloalkyl;
$R_3$ and $R_7$ are independently hydrogen, hydroxyl, methoxy, oxo, hydroximino, or alkoxyimino;
$R_4$ and $R_8$ are independently hydrogen, hydroxyl, $C_1$-$C_8$ alkanoyloxy, benzoyloxy, di-$C_1$-$C_8$ alkylamino benzoyloxy, ($C_1$-$C_8$ alkoxy)$_p$, $C_1$-$C_8$ alkylthio, $C_1$-$C_8$ alkylthioalkoxy or oleandrosyloxy;
$R_9$ and $R_{10}$ are oxygen, $NR_{11}$, —ONR$_{11}$C(=O)—, —ONR$_{11}$C(=O)NR$_{11}$—, —ONR$_{11}$C(=O)O—, —NR$_{11}$C(=O)NR$_{11}$—, —NR$_{11}$C(=O)O—, —N($R_{11}$)S(O)$_2$N($R_{11}$)—, —N($R_{11}$)S(O)$_2$—, —NR$_{11}$C(=O)— or —OC(=O)O—; and
L is an arylene linker;
wherein said linker may optionally be substituted with one or more groups selected from cyano, nitro, hydroxy, and halogen.

Another embodiment the invention provides for a compound of formula (I) wherein:
$R_1$ and $R_5$ are hydrogen;
$R_2$ and $R_6$ are independently isopropyl, sec-butyl or cyclohexyl;
$R_3$ and $R_7$ are independently hydroxyl, methoxy or hydroximino;
$R_4$ and $R_8$ are hydrogen;
$R_9$ and $R_{10}$ are oxygen or $NR_{11}$;
L is an arylene linker;
wherein said linker may optionally be substituted with one or more groups selected from cyano, nitro, hydroxy, and halogen; and
m and n are 2.

In another embodiment the invention provides for a compound of formula (I) wherein:
$R_1$ and $R_5$ are hydrogen;
$R_2$ and $R_6$ are independently isopropyl, sec-butyl or cyclohexyl;
$R_3$ and $R_7$ independently are hydroxyl, methoxy or hydroximino;
$R_4$ and $R_8$ are hydrogen;
$R_9$ and $R_{10}$ are independently —ONR$_{11}$C(=O)—, —ONR$_{11}$C(=O)NR$_{11}$—, —ONR$_{11}$C(=O)O—, —NR$_{11}$C(=O)NR$_{11}$—, or —NR$_{11}$C(=O)O—;
L is an arylene linker;
wherein said linker may optionally be substituted with one or more groups selected from cyano, nitro, hydroxy, and halogen; and
m and n are 2.

In still another embodiment, the invention provides for a compound of formula (I) wherein:

$R_1$ and $R_5$ are hydrogen;
$R_2$ and $R_6$ are independently isopropyl, sec-butyl or cyclohexyl;
$R_3$ and $R_7$ are independently hydroxyl, methoxy or hydroximino;
$R_4$ and $R_8$ are hydrogen;
$R_9$ and $R_{10}$ are independently $-N(R_{11}S(O)_2N(R_{11})-$, $-N(R_{11}S(O)_2-$, $-NR_{11}C(=O)-$ or $-OC(=O)O-$;
L is an arylene linker;
wherein said linker may optionally be substituted with one or more groups selected from cyano, nitro, hydroxy, and halogen; and
m and n are 2

Another embodiment the invention provides for a compound of formula (I) wherein:

A is a single bond;
B is a single bond;
$R_1$ and $R_5$ are hydrogen;
$R_2$ and $R_6$ are cyclohexyl;
$R_3$ and $R_7$ are hydroximino;
$R_4$ and $R_8$ are hydrogen;
$R_9$ and $R_{10}$ independently are oxygen or $NR_{11}$;
L is an arylene linker;
wherein said linker may optionally be substituted with one or more groups selected from cyano, nitro, hydroxy, and halogen; and
m and n are 1.

Another embodiment of the first object of the invention provides for a compound of formula (I) wherein:

A is a single bond;
B is a single bond;
$R_1$ and $R_5$ are alkoxyimino;
$R_2$ and $R_6$ are branched $C_2$-$C_8$ alkenyl;
$R_3$ and $R_7$ are hydroxyl;
$R_4$ and $R_8$ are hydrogen;
$R_9$ and $R_{10}$ are independently oxygen or $NR_{11}$;
L is an arylene linker;
wherein said linker may optionally be substituted with one or more groups selected from cyano, nitro, hydroxy, and halogen; and
m and n are 0.

Another embodiment of the invention provides for a compound of formula (I) wherein:

$R_9$ and $R_{10}$ are independently selected from $-NR_{11}C(=O)-$, $-NR_{11}C(=O)O-$, $-NR_{11}C(=O)NR_{11}-$, $-ONR_{11}C(=O)-$, $-ONR_{11}C(=O)O-$, $-ONR_{11}C(=O)NR_{11}-$, $-N(R_{11}S(O)_2N(R_{11})-$, $-N(R_{11}S(O)_2-$, $-NR_{11}C(=O)-$ or $-OC(=O)O-$;
$R_{11}$ is H or $R_2$;
L is a linker selected from $C_2$-$C_{20}$ alkylene, $C_2$-$C_{20}$ alkenylene, $C_2$-$C_{20}$ alkynylene, $C_3$-$C_8$ cycloalkylene, arylene, aryloxy arylene, heteroarylene, or any combination thereof, which may optionally contain a N, O, S, P, or Si atom; and
wherein said linker may optionally be substituted with one or more groups selected from cyano, nitro, hydroxy, halogen, O, N, S, $C_1$-$C_6$ alkyl, $C_3$-$C_8$ cycloalkyl, $C_1$-$C_6$ alkoxy, $C_1$-$C_6$ thioalkyl, oxo, oximino, and alkoxyimino.

Another embodiment of the invention provides for a compound of formula (I) wherein:

$R_9$ and $R_{10}$ are independently $-ONR_{11}C(=O)-$, $-ONR_{11}C(=O)NR_{11}-$, $-ONR_{11}C(=O)O-$, $-NR_{11}C(=O)NR_{11}-$, $-NR_{11}C(=O)O-$, $-N(R_{11})S(O)_2N(R_{11})-$, $-N(R_{11})S(O)_2-$, $-NR_{11}C(=O)-$ or $-OC(=O)O-$;
$R_{11}$ is H or $R_2$;
L is a $C_1$-$C_{20}$ alkylene linker.

Another embodiment of the invention provides for a compound of formula (I) wherein:

A is a single or double bond;
B is a single or double bond;
$R_1$ and $R_5$ are hydrogen or hydroxyl;
$R_2$ and $R_6$ are independently isopropyl, sec-butyl or cyclohexyl;
$R_3$ and $R_7$ are hydroxyl, methoxy or hydroximino;
$R_4$ and $R_8$ are hydrogen;
$R_9$ and $R_{10}$ are independently $-NR_{11}C(=O)NR_{11}-$, or $-NR_{11}C(=O)O-$;
$R_{11}$ is hydrogen;
L is a $C_1$-$C_{20}$ alkylene linker; and
m and n are 2;
or pharmaceutically acceptable salts thereof.

In another embodiment, the invention provides for a compound of formula (I) wherein:

A is a single or double bond;
B is a single or double bond;
$R_1$ and $R_5$ are hydrogen or hydroxyl;
$R_2$ and $R_6$ are independently isopropyl, sec-butyl or cyclohexyl;
$R_3$ and $R_7$ are hydroxyl, methoxy or hydroximino;
$R_4$ and $R_8$ are hydrogen;
$R_9$ and $R_{10}$ are independently $-ONR_{11}C(=O)-$, $-ONR_{11}C(=O)NR_{11}-$ or $-ONR_{11}C(=O)O-$;
$R_{11}$ is hydrogen;
L is a $C_1$-$C_{20}$ alkylene linker; and
m and n are 2.

In another embodiment, the invention provides for a compound of formula (I) wherein:

A is a single or double bond;
B is a single or double bond;
$R_1$ and $R_5$ are independently hydrogen or hydroxyl;
$R_2$ and $R_6$ are independently selected from the group consisting of isopropyl, sec-butyl and cyclohexyl;
$R_3$ and $R_7$ are independently hydroxyl, methoxy or hydroximino;
$R_4$ and $R_8$ are hydrogen;
$R_9$ and $R_{10}$ are independently $-N(R_{11}S(O)_2N(R_{11})-$, $-N(R_{11}S(O)_2-$, $-NR_{11}C(=O)-$ or $-OC(=O)O-$;
$R_{11}$ is hydrogen;
L is a $C_1$-$C_{20}$ alkylene linker; and
m and n are 2

Another embodiment of the first object of the invention provides for a compound of formula (I) wherein:

A is a single bond;
B is a single bond;
$R_1$ and $R_5$ are hydrogen;
$R_2$ and $R_6$ are cyclohexyl;
$R_3$ and $R_7$ are independently hydroximino, hydroxyl or methoxy;
$R_4$ and $R_8$ are hydrogen;
$R_9$ and $R_{10}$ are independently $-NR_{11}C(=O)NR_{11}-$, or $-NR_{11}C(=O)O-$;
$R_{11}$ is hydrogen;
L is a $C_1$-$C_{20}$ alkylene linker; and
m and n are 1;
or pharmaceutically acceptable salts thereof.

In still another embodiment, the invention provides for a compound of formula (I) wherein:

A is a single bond;
B is a single bond;
$R_1$ and $R_5$ are hydrogen;

$R_2$ and $R_6$ are cyclohexyl;
$R_3$ and $R_7$ are independently hydroximino, hydroxyl or methoxy;
$R_4$ and $R_8$ are hydrogen;
$R_9$ and $R_{10}$ are independently —$ONR_{11}C(=O)$—, —$ONR_{11}C(=O)NR_{11}$— or —$ONR_{11}C(=O)O$—;
$R_H$ is hydrogen;
L is a $C_1$-$C_{20}$ alkylene linker; and
m and n are 1.

In yet another embodiment of the first object of the invention provides for a compound of formula (I) wherein:
A is a single bond;
B is a single bond;
$R_1$ and $R_5$ are hydrogen;
$R_2$ and $R_6$ are cyclohexyl;
$R_3$ and $R_7$ are independently hydroximino, hydroxyl or methoxy;
$R_4$ and $R_8$ are hydrogen;
$R_9$ and $R_{10}$ are independently —$N(R_{11}S(O)_2N(R_{11})$—, —$N(R_{11}S(O)_2$—, —$NR_{11}C(=O)$— or —$OC(=O)O$—;
$R_{11}$ is hydrogen;
L is a $C_1$-$C_{20}$ alkylene linker; and
m and n are 1.

Another embodiment of the first object of the invention provides for a compound of formula (I) wherein:
A is a single bond;
B is a single bond;
$R_1$ and $R_5$ are alkoxyimino;
$R_2$ and $R_6$ are branched $C_2$-$C_8$ alkenyl;
$R_3$ and $R_7$ are hydroxyl;
$R_4$ and $R_8$ are hydrogen;
$R_9$ and $R_{10}$ are $NR_{11}$;
$R_{11}$ is hydrogen;
L is a $C_1$-$C_{20}$ alkylene linker; and
m and n are 0;
or pharmaceutically acceptable salts thereof.

Another embodiment of the first object of the invention provides for a compound of formula (I) wherein:
A is a single or double bond;
B is a single or double bond;
$R_1$ and $R_5$ are independently hydrogen, hydroxyl, oxo, oximino or alkoxyimino, provided that $R_1$ is hydroxyl only when A is a single bond, and that $R_5$ is hydroxyl only when B is a single bond;
$R_2$ and $R_6$ are independently linear or branched $C_1$-$C_8$ alkyl, $C_2$-$C_8$ alkenyl, or $C_3$-$C_8$ cycloalkyl;
$R_3$ and $R_7$ are independently hydroxyl, methoxy, oxo, hydroximino, and alkoxyimino;
$R_4$ and $R_8$ are independently selected from the group consisting of hydrogen, hydroxyl, $C_1$-$C_8$ alkanoyloxy, benzoyloxy, di-$C_1$-$C_8$ alkylamino benzoyloxy, ($C_1$-$C_8$ alkoxy)$_p$, $C_1$-$C_8$ alkylthio, $C_1$-$C_8$ alkylthioalkoxy or oleandrosyloxy;
$R_9$ and $R_{10}$ are —$NR_{11}C(=O)$—;
$R_{11}$ is H or $R_2$;
L is a $C_1$-$C_{20}$ alkylene linker;
m and n are independently 0, 1, or 2; and
p is 1-3;
or pharmaceutically acceptable salts thereof.

Another embodiment of the first object of the invention provides for a compound of formula (I) wherein:
A is a single or double bond;
B is a single or double bond;
$R_1$ and $R_5$ are hydrogen or hydroxy;
$R_2$ and $R_6$ are independently isopropyl, sec-butyl or cyclohexyl;
$R_3$ and $R_7$ are independently hydroxyl, methoxy or hydroximino;
$R_4$ and $R_8$ are hydrogen;
$R_9$ and $R_{10}$ are —$NR_{11}C(=O)$—;
$R_{11}$ is hydrogen;
L is a $C_1$-$C_{20}$ alkylene linker; and
m and n are 2;
or pharmaceutically acceptable salts thereof.

Another embodiment of the first object of the invention provides for a compound of formula (I) wherein:
A is a single bond;
B is a single bond;
$R_1$ and $R_5$ are independently hydrogen or hydroxy;
$R_2$ and $R_6$ are cyclohexyl;
$R_3$ and $R_7$ are independently hydroxyl, methoxy or hydroximino;
$R_4$ and $R_8$ are hydrogen;
$R_9$ and $R_{10}$ are —$NR_{11}C(=O)$—;
$R_{11}$ is hydrogen;
L is a $C_1$-$C_{20}$ alkylene linker; and
m and n are 1;
or pharmaceutically acceptable salts thereof.

Another embodiment of the first object of the invention provides for a compound of formula (I) wherein:
A is a single bond;
B is a single bond;
$R_1$ and $R_5$ are independently hydrogen, hydroxy or alkoxyimino;
$R_2$ and $R_6$ are independently branched $C_2$-$C_8$ alkenyl, sec-butyl or iso-propyl;
$R_3$ and $R_7$ are hydroxyl;
$R_4$ and $R_8$ are hydrogen;
$R_9$ and $R_{10}$ are —$NR_{11}C(=O)$—;
$R_{11}$ is hydrogen;
L is a $C_1$-$C_{20}$ alkylene linker; and
m and n are 0;
or pharmaceutically acceptable salts thereof.

Another embodiment of the invention provides for a compound of formula (I) wherein:
A is a single or double bond;
B is a single or double bond;
$R_1$ and $R_5$ are independently hydrogen, hydroxyl, oxo, oximino or alkoxyimino, provided that $R_1$ is hydroxyl only when A is a single bond, and that $R_5$ is hydroxyl only when B is a single bond;
$R_2$ and $R_6$ are independently linear or branched $C_1$-$C_8$ alkyl, $C_2$-$C_8$ alkenyl, or $C_3$-$C_8$ cycloalkyl;
$R_3$ and $R_7$ are independently hydroxyl, methoxy, oxo, hydroximino, or alkoxyimino;
$R_4$ and $R_8$ are independently hydrogen, hydroxyl, $C_1$-$C_8$ alkanoyloxy, benzoyloxy, di-$C_1$-$C_8$ alkylamino benzoyloxy, ($C_1$-$C_8$ alkoxy)$_p$, $C_1$-$C_8$ alkylthio, $C_1$-$C_8$ alkylthioalkoxy or oleandrosyloxy;
$R_9$ and $R_{10}$ are —$NR_{11}C(=O)O$—;
$R_{11}$ is H or $R_2$;
L is a $C_1$-$C_{10}$ alkylene linker;
m and n are independently 0, 1, or 2; and
p is 1-3;
or pharmaceutically acceptable salts thereof.

Another embodiment of the invention provides for a compound of formula (I) wherein:
A is a single or double bond;
B is a single or double bond;
$R_1$ and $R_5$ are independently hydrogen or hydroxy;
$R_2$ and $R_6$ are independently isopropyl, sec-butyl or cyclohexyl;
$R_3$ and $R_7$ are independently hydroxyl, methoxy or hydroximino;
$R_4$ and $R_8$ are hydrogen;

$R_9$ and $R_{10}$ are —$NR_{11}C(=O)O$—;
$R_{11}$ is hydrogen;
L is a $C_1$-$C_{10}$ alkylene linker; and
m and n are 2;
or pharmaceutically acceptable salts thereof.

Another embodiment of the first object of the invention provides for a compound of formula (I) wherein:
A is a single bond;
B is a single bond;
$R_1$ and $R_5$ are independently hydrogen or hydroxyl;
$R_2$ and $R_6$ are cyclohexyl;
$R_3$ and $R_7$ are independently hydroxy, methoxy, or hydroximino;
$R_4$ and $R_8$ are hydrogen;
$R_9$ and $R_{10}$ are —$NR_{11}C(=O)O$—;
$R_{11}$ is hydrogen;
L is a $C_1$-$C_{10}$ alkylene linker; and
m and n are 1;
or pharmaceutically acceptable salts thereof.

Another embodiment of the first object of the invention provides for a compound of formula (I) wherein:
A is a single bond;
B is a single bond;
$R_1$ and $R_5$ are alkoxyimino;
$R_2$ and $R_6$ are branched $C_2$-$C_8$ alkenyl;
$R_3$ and $R_7$ are hydroxyl;
$R_4$ and $R_8$ are hydrogen;
$R_9$ and $R_{10}$ are —$NR_{11}C(=O)O$—;
$R_{11}$ is hydrogen;
L is a $C_1$-$C_{10}$ alkylene linker; and
m and n are 0;
or pharmaceutically acceptable salts thereof.

Another embodiment of the invention provides for a compound of formula (I) wherein:
A is a single or double bond;
B is a single or double bond;
$R_1$ and $R_5$ are independently hydrogen, hydroxyl, oxo, oximino or alkoxyimino, provided that $R_1$ is hydroxyl only when A is a single bond, and that $R_5$ is hydroxyl only when B is a single bond;
$R_2$ and $R_6$ are independently linear or branched $C_1$-$C_8$ alkyl, $C_2$-$C_8$ alkenyl, or $C_3$-$C_8$ cycloalkyl;
$R_3$ and $R_7$ are independently hydroxyl, methoxy, oxo, hydroximino, or alkoxyimino;
$R_4$ and $R_8$ are independently hydrogen, hydroxyl, $C_1$-$C_8$ alkanoyloxy, benzoyloxy, di-$C_1$-$C_8$ alkylamino benzoyloxy, ($C_1$-$C_8$ alkoxy)$_p$, $C_1$-$C_8$ alkylthio, $C_1$-$C_8$ alkylthioalkoxy or oleandrosyloxy;
$R_9$ and $R_{10}$ are —$NR_{11}C(=O)NR_{11}$—;
$R_{11}$ is H or $R_2$;
L is a $C_1$-$C_{10}$ alkylene linker;
m and n are independently 0, 1, or 2; and
p is 1-3;
or pharmaceutically acceptable salts thereof.

Another embodiment of the invention provides for a compound of formula (I) wherein:
A is a single or double bond;
B is a single or double bond;
$R_1$ and $R_5$ are independently hydrogen or hydroxy;
$R_2$ and $R_6$ are independently isopropyl, sec-butyl or cyclohexyl;
$R_3$ and $R_7$ are independently hydroxyl, methoxy or hydroximino;
$R_4$ and $R_8$ are hydrogen;
$R_9$ and $R_{10}$ are $NR_{11}C(=O)NR_{11}$;
$R_{11}$ is hydrogen;
L is a $C_1$-$C_{10}$ alkylene linker; and
m and n are 2;
or pharmaceutically acceptable salts thereof.

Another embodiment of the first object of the invention provides for a compound of formula (I) wherein:
A is a single bond;
B is a single bond;
$R_1$ and $R_5$ are independently hydrogen or hydroxy;
$R_2$ and $R_6$ are cyclohexyl;
$R_3$ and $R_7$ are independently hydroxyl, methoxy or hydroximino;
$R_4$ and $R_8$ are hydrogen;
$R_9$ and $R_{10}$ are $NR_{11}C(=O)NR_{11}$;
$R_{11}$ is hydrogen;
L is a $C_1$-$C_{10}$ alkylene linker; and
m and n are 1;
or pharmaceutically acceptable salts thereof.

Another embodiment of the first object of the invention provides for a compound of formula (I) wherein:
A is a single bond;
B is a single bond;
$R_1$ and $R_5$ are independently hydrogen, hydroxy or alkoxyimino;
$R_2$ and $R_6$ are branched $C_2$-$C_8$ alkenyl;
$R_3$ and $R_7$ are independently hydroxyl or methoxy;
$R_4$ and $R_8$ are hydrogen;
$R_9$ and $R_{10}$ are $NR_{11}C(=O)NR_{11}$;
$R_{11}$ is hydrogen;
L is a $C_1$-$C_{10}$ alkylene linker; and
m and n are 0;
or pharmaceutically acceptable salts thereof.

Another embodiment of the invention provides for a compound of formula (I) wherein:
A is a double bond;
B is a double bond;
$R_1$ and $R_5$ are independently hydrogen or hydroxy;
$R_2$ and $R_6$ are independently isopropyl, sec-butyl or cyclohexyl;
$R_3$ and $R_7$ are independently hydroxyl or methoxy;
$R_4$ and $R_8$ are hydrogen;
$R_9$ and $R_{10}$ are independently —$ONR_{11}C(=O)$—, —$ONR_{11}C(=O)NR_{11}$—, or —$ONR_{11}C(=O)O$—;
$R_{11}$ is hydrogen;
L is a $C_1$-$C_{10}$ alkylene linker; and
m and n are 2.

In yet another embodiment, the invention provides for a compound of formula (I) wherein:
A is a double bond;
B is a double bond;
$R_1$ and $R_5$ are independently hydrogen or hydroxy;
$R_2$ and $R_6$ are independently isopropyl, sec-butyl or cyclohexyl;
$R_3$ and $R_7$ are independently hydroxyl or methoxy;
$R_4$ and $R_8$ are hydrogen;
$R_9$ and $R_{10}$ are independently —$NR_{11}C(=O)NR_{11}$—, or —$NR_{11}C(=O)O$—;

$R_{11}$ is hydrogen;
L is a $C_1$-$C_{10}$ alkylene linker; and
m and n are 2.

In another embodiment, the invention provides for a compound of formula (I) wherein:
A is a double bond;
B is a double bond;
$R_1$ and $R_5$ are hydrogen;
$R_2$ and $R_6$ are independently isopropyl or sec-butyl;
$R_3$ and $R_7$ are independently hydroxyl or methoxy;
$R_4$ and $R_8$ are hydrogen;
$R_9$ and $R_{10}$ are independently —$ONR_{11}C(=O)$—, —$ONR_{11}C(=O)NR_{11}$—, or —$ONR_{11}C(=O)O$—;
$R_{11}$ is hydrogen;
L is a $C_2$-$C_8$ alkylene linker; and
m and n are 2.

In yet another embodiment, the invention provides for a compound of formula (I) wherein:
A is a double bond;
B is a double bond;
$R_1$ and $R_5$ are hydrogen;
$R_2$ and $R_6$ are independently isopropyl or sec-butyl;
$R_3$ and $R_7$ are independently hydroxyl or methoxy;
$R_4$ and $R_8$ are hydrogen;
$R_9$ and $R_{10}$ are independently —$NR_{11}C(=O)NR_{11}$— or —$NR_{11}C(=O)O$—;
$R_{11}$ is hydrogen;
L is a $C_2$-$C_8$ alkylene linker; and
m and n are 2.

In another embodiment, the invention provides for a compound of formula (I) wherein:
A is a double bond;
B is a double bond;
$R_1$ and $R_5$ are hydrogen;
$R_2$ and $R_6$ are independently isopropyl or sec-butyl;
$R_3$ and $R_7$ are independently hydroxyl or methoxy;
$R_4$ and $R_8$ are hydrogen;
$R_9$ and $R_{10}$ are independently —$ONR_{11}C(=O)$—, —$ONR_{11}C(=O)NR_{11}$—, or —$ONR_{11}C(=O)O$—;
$R_{11}$ is hydrogen;
L is a $C_2$-$C_8$ alkylene linker; and
m and n are 1.

In another embodiment, the invention provides for a compound of formula (I) wherein:
A is a double bond;
B is a double bond;
$R_1$ and $R_5$ are hydrogen;
$R_2$ and $R_6$ are independently isopropyl or sec-butyl;
$R_3$ and $R_7$ are independently hydroxyl or methoxy;
$R_4$ and $R_8$ are hydrogen;

$R_9$ and $R_{10}$ are independently —$NR_{11}C(=O)NR_{11}$— or —$NR_{11}C(=O)O$—;
$R_{11}$ is hydrogen;
L is a $C_2$-$C_8$ alkylene linker; and
m and n are 1.

In another embodiment, the invention provides for a compound of formula (I) wherein:
A is a double bond;
B is a double bond;
$R_1$ and $R_5$ are hydrogen;
$R_2$ and $R_6$ are independently isopropyl or sec-butyl;
$R_3$ and $R_7$ are independently hydroxyl or methoxy;
$R_4$ and $R_8$ are hydrogen;
$R_9$ and $R_{10}$ are independently —$ONR_{11}C(=O)$—, —$ONR_{11}C(=O)NR_{11}$—, or —$ONR_{11}C(=O)O$—;
$R_{11}$ is hydrogen;
L is a $C_2$-$C_8$ alkylene linker; and
m and n are 0.

In another embodiment, the invention provides for a compound of formula (I) wherein:
A is a double bond;
B is a double bond;
$R_1$ and $R_5$ are hydrogen;
$R_2$ and $R_6$ are independently isopropyl or sec-butyl;
$R_3$ and $R_7$ are independently hydroxyl or methoxy;
$R_4$ and $R_8$ are hydrogen;
$R_9$ and $R_{10}$ are independently —$NR_{11}C(=O)NR_{11}$— or —$NR_{11}C(=O)O$—;
$R_{11}$ is hydrogen;
L is a $C_2$-$C_8$ alkylene linker; and
m and n are 0.

In various embodiments, the invention provides macrocyclic lactone dimer compounds shown in Tables 1, 2 and 3 below, where the monomer is avermectin B1. The first number in the compound number (i.e. 1-B1-1 from Table 1) corresponds to the groups $R_9$ and $R_{10}$ and the last number (i.e. 1-B1-1) refers to the carbon number of the alkylene group. For example, 1-B1-5 corresponds to a compound of formula (I) where $R_9$ and $R_{10}$ are $NR_{11}$ and linker L is a C5 alkylene group. The compounds in Tables 1 and 2 include all stereoisomers. The structure shown in the third column of Table 3 is the saccharide portion of the molecule that includes groups $R_9$, $R_{10}$ and L bonded to the 4'-position of the avermectin B1 residue.

Table 1 below shows various compounds of formula (I) derived from avermectin B1a wherein A and B are both double bonds, $R_1$ and $R_5$ are hydrogen, $R_2$ and $R_6$ are sec-butyl, $R_4$ and $R_8$ are hydrogen, $R_3$ and $R_7$ are OH; $R_9$, $R_{10}$, and linker L are as defined in the table, $R_{11}$ is hydrogen or $C_1$-$C_8$ alkyl, and m and n are each 2.

TABLE 1

| Compound | $R_9$ | $R_{10}$ | L |
|---|---|---|---|
| 1-B1a-1 to 1-B1a-10 | $NR_{11}$ | $NR_{11}$ | $C_1$-$C_{10}$ alkylene |
| 2-B1a-1 to 2-B1a-10 | —$NR_{11}C(=O)$— | —$NR_{11}C(=O)$— | $C_1$-$C_{10}$ alkylene |
| 3-B1a-1 to 3-B1a-10 | —$NR_{11}C(=O)O$— | —$NR_{11}C(=O)O$— | $C_1$-$C_{10}$ alkylene |
| 4-B1a-1 to 4-B1a-10 | —$N(R_{11})C(=O)N(R_{11})$— | —$N(R_{11})C(=O)N(R_{11})$— | $C_1$-$C_{10}$ alkylene |
| 5-B1a-1 to 5-B1a-10 | —$N(R_{11})S(O)_2$— | —$N(R_{11})S(O)_2$— | $C_1$-$C_{10}$ alkylene |
| 6-B1a-1 to 6-B1a-10 | —$ONR_{11}C(=O)NR_{11}$— | —$ONR_{11}C(=O)NR_{11}$— | $C_1$-$C_{10}$ alkylene |
| 7-B1a-1 to 7-B1a-10 | —$ONR_{11}C(=O)O$— | —$ONR_{11}C(=O)O$— | $C_1$-$C_{10}$ alkylene |
| 8-B1a-1 to 8-B1a-10 | —$NR11C(=O)O$— | —$NR11C(=O)O$— | $C_1$-$C_{10}$ alkylene |

TABLE 1-continued

| Compound | $R_9$ | $R_{10}$ | L |
|---|---|---|---|
| 9-B1a-1 to 9-B1a-10 | —$ONR_{11}C(=O)O$— | —$ONR_{11}C(=O)O$— | $C_1$-$C_{10}$ alkylene |
| 10-B1a | $NR_{11}$ | $NR_{11}$ | phenylene |
| 11-B1a | —$NR_{11}C(=O)$— | —$NR_{11}C(=O)$— | phenylene |
| 12-B1a | —$NR_{11}C(=O)O$— | —$NR_{11}C(=O)O$— | phenylene |
| 13-B1a | —$N(R_{11})C(=O)N(R_{11})$— | —$N(R_{11})C(=O)N(R_{11})$— | phenylene |
| 14-B1a | —$N(R_{11})S(O)_2$— | —$N(R_{11})S(O)_2$— | phenylene |
| 15-B1a | —$ONR_{11}C(=O)NR_{11}$— | —$ONR_{11}C(=O)NR_{11}$— | phenylene |
| 16-B1a | —$ONR_{11}C(=O)O$— | —$ONR_{11}C(=O)O$— | phenylene |
| 17-B1a | —$NR_{11}C(=O)O$— | —$NR_{11}C(=O)O$— | Phenylene |
| 18-B1a | —$ONR_{11}C(=O)O$— | —$ONR_{11}C(=O)O$— | Phenylene |

Table 2 below shows various compounds of formula (I) derived from avermectin B1b wherein A and B are both double bonds, $R_1$ and $R_5$ are hydrogen, $R_2$ and $R_6$ are iso-propyl, $R_4$ and $R_8$ are hydrogen, $R_3$ and $R_7$ are OH; $R_9$, $R_{10}$, and linker L are as defined in the table, $R_{11}$ is hydrogen or $C_1$-$C_8$ alkyl, and m and n are each 2.

TABLE 2

| Compound | $R_9$ | $R_{10}$ | L |
|---|---|---|---|
| 1-B1b-1 to 1-B1b-10 | $NR_{11}$ | $NR_{11}$ | $C_1$-$C_{10}$ alkylene |
| 2-B1b-1 to 2-B1b-10 | —$NR_{11}C(=O)$— | —$NR_{11}C(=O)$— | $C_1$-$C_{10}$ alkylene |
| 3-B1b-1 to 3-B1b-10 | —$NR_{11}C(=O)O$— | —$NR_{11}C(=O)O$— | $C_1$-$C_{10}$ alkylene |
| 4-B1b-1 to 4-B1b-10 | —$N(R_{11})C(=O)N(R_{11})$— | —$N(R_{11})C(=O)N(R_{11})$— | $C_1$-$C_{10}$ alkylene |
| 5-B1b-1 to 5-B1b-10 | —$N(R_{11})S(O)_2$— | —$N(R_{11})S(O)_2$— | $C_1$-$C_{10}$ alkylene |
| 6-B1b-1 to 6-B1b-10 | —$ONR_{11}C(=O)NR_{11}$— | —$ONR_{11}C(=O)NR_{11}$— | $C_1$-$C_{10}$ alkylene |
| 7-B1b-1 to 7-B1b-10 | —$ONR_{11}C(=O)O$— | —$ONR_{11}C(=O)O$— | $C_1$-$C_{10}$ alkylene |
| 8-B1b-1 to 8-B1b-10 | —$NR_{11}C(=O)O$— | —$NR_{11}C(=O)O$— | $C_1$-$C_{10}$ alkylene |
| 9-B1b-1 to 9-B1b-10 | —$ONR_{11}C(=O)O$— | —$ONR_{11}C(=O)O$— | $C_1$-$C_{10}$ alkylene |
| 10-B1b | $NR_{11}$ | $NR_{11}$ | phenylene |
| 11-B1b | —$NR_{11}C(=O)$— | —$NR_{11}C(=O)$— | phenylene |
| 12-B1b | —$NR_{11}C(=O)O$— | —$NR_{11}C(=O)O$— | phenylene |
| 13-B1b | —$N(R_{11})C(=O)N(R_{11})$— | —$N(R_{11})C(=O)N(R_{11})$— | phenylene |
| 14-B1b | —$N(R_{11})S(O)_2$— | —$N(R_{11})S(O)_2$— | phenylene |
| 15-B1b | —$ONR_{11}C(=O)NR_{11}$— | —$ONR_{11}C(=O)NR_{11}$— | phenylene |
| 16-B1b | —$ONR_{11}C(=O)O$— | —$ONR_{11}C(=O)O$— | phenylene |
| 17-B1b | —$NR_{11}C(=O)O$— | —$NR_{11}C(=O)O$— | Phenylene |
| 18-B1b | —$ONR_{11}C(=O)O$— | —$ONR_{11}C(=O)O$— | Phenylene |

In other embodiments, the invention provides macrocyclic lactone dimer compounds 1-B2a-1 to 18-B2a derived from avermectin B2a wherein A and B are both single bonds, $R_1$ and $R_5$ are OH, $R_2$ and $R_6$ are sec-butyl, $R_4$ and $R_8$ are hydrogen, $R_3$ and $R_7$ are OH; $R_9$, $R_{10}$, and linker L are as defined in the Table 1 above for the corresponding compound numbers, $R_{11}$ is hydrogen or $C_1$-$C_8$ alkyl, and m and n are each 2.

In other embodiments, the invention provides macrocyclic lactone dimer compounds 1-B2b to 18-B2b derived from avermectin B2b wherein A and B are both single bonds, $R_1$ and $R_5$ are OH, $R_2$ and $R_6$ are iso-propyl, $R_4$ and $R_8$ are hydrogen, $R_3$ and $R_7$ are OH; $R_9$, $R_{10}$, and linker L are as defined in the Table 1 above for the corresponding compound numbers, $R_{11}$ is hydrogen or $C_1$-$C_8$ alkyl, and m and n are each 2.

In still other embodiments, the invention provides macrocyclic lactone dimer compounds 1-A1a-1 to 18-A1a derived from avermectin A1a wherein A and B are both double bonds, $R_1$ and $R_5$ are hydrogen, $R_2$ and $R_6$ are sec-butyl, $R_4$ and $R_8$ are hydrogen, $R_3$ and $R_7$ are methoxy; $R_9$, $R_{10}$, and linker L are as defined in the Table 1 above for the corresponding compound numbers, $R_{11}$ is hydrogen or $C_1$-$C_8$ alkyl, and m and n are each 2.

In other embodiments, the invention provides macrocyclic lactone dimer compounds 1-A1b-1 to 18-A1b derived from avermectin A1b wherein A and B are both double bonds, $R_1$ and $R_5$ are hydrogen, $R_2$ and $R_6$ are iso-propyl, $R_4$ and $R_8$ are hydrogen, $R_3$ and $R_7$ are methoxy; $R_9$, $R_{10}$, and linker L are as defined in the Table 1 above for the corresponding compound numbers, $R_{11}$ is hydrogen or $C_1$-$C_8$ alkyl, and m and n are each 2.

In other embodiments, the invention provides macrocyclic lactone dimer compounds 1-A2a-1 to 18-A2a derived from avermectin A2a wherein A and B are both single bonds, $R_1$ and $R_5$ are OH, $R_2$ and $R_6$ are sec-butyl, $R_4$ and $R_8$ are hydrogen, $R_3$ and $R_7$ are methoxy; $R_9$, $R_{10}$, and linker L are as defined in the Table 1 above for the corresponding compound numbers, $R_{11}$ is hydrogen or $C_1$-$C_8$ alkyl, and m and n are each 2.

In yet other embodiments, the invention provides macrocyclic lactone dimer compounds 1-A2b-1 to 18-A2b derived from avermectin A2b wherein A and B are both single bonds, $R_1$ and $R_5$ are OH, $R_2$ and $R_6$ are iso-propyl, $R_4$ and $R_8$ are hydrogen, $R_3$ and $R_7$ are methoxy; $R_9$, $R_{10}$, and linker L are as defined in the Table 1 above for the corresponding compound numbers, $R_{11}$ is hydrogen or $C_1$-$C_8$ alkyl, and m and n are each 2.

In still other embodiments of the invention, macrocyclic lactone dimer compounds are provided wherein $R_9$, $R_{10}$ and L are as defined for the corresponding numbered compounds 1-B1b-1 to 18-B1b in Table 1 for the corresponding compound numbers, $R_{11}$ is hydrogen or $C_1$-$C_8$ alkyl, and variables A, B, $R_1$, $R_5$, $R_2$, $R_6$, $R_4$, $R_8$, $R_3$, $R_7$ m and n correspond to the substituents of the macrocyclic lactones dimadectin, doramectin, emamectin, eprinomectin, ivermectin, latidectin, lepimectin, or selamectin.

In still other embodiments of the invention, macrocyclic lactone dimer compounds are provided wherein $R_9$, $R_{10}$ and L are as defined for the corresponding numbered compounds 1-B1b-1 to 18-B1b in Table 1 for the corresponding compound numbers, $R_{11}$ is hydrogen or $C_1$-$C_8$ alkyl, and variables A, B, $R_1$, $R_5$, $R_2$, $R_6$, $R_4$, $R_8$, $R_3$, $R_7$ m and n correspond to the substituents of the milbemycin compounds milbemectin, milbemycin D, moxidectin or nemadectin.

In yet other embodiments of the invention, macrocyclic lactone dimer compounds are provided wherein $R_9$, $R_{10}$ and L are as defined for the corresponding numbered compounds 1-B1b-1 to 18-B1b in Table 1, $R_{11}$ is hydrogen or $C_1$-$C_8$ alkyl, and the macrocyclic acid lactone monomer is a 5-oxo or 5-oxime derivative of an avermectins or milbemycin compound.

In various embodiments, the invention provides macrocyclic lactone dimer compounds shown in Table 3 below, where the monomer is avermectin B1a. The structure shown in the third column is the saccharide portion of the molecule that includes groups $R_9$, $R_{10}$ and L bonded to the 4'-position, and where Z is an avermectin B1a residue having the following structure:

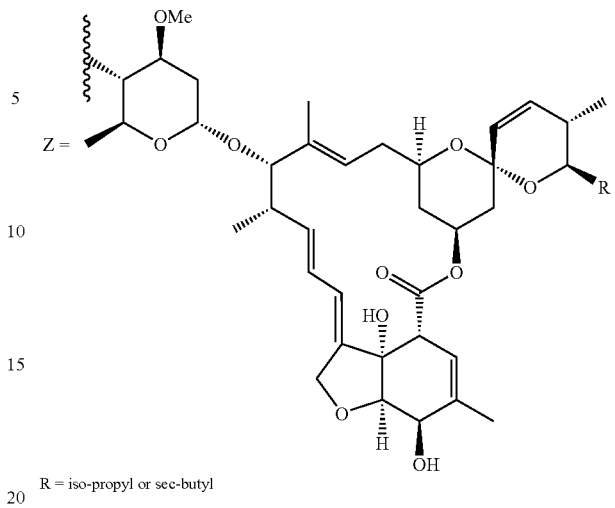

R = iso-propyl or sec-butyl

The compound numbering in Table 3 is consistent with the methodology described above for Tables 1 and 2, where the last number corresponds to the different compounds having various alkylene carbon chains. For Example, compound 19-B1-2 refers to a compound of the structure shown in the second column having a C2 alkylene linker L, 19-B1-3 refers to a compound having the shown structure with a C3 alkylene chain for linker L, and so on.

TABLE 3

Avermectin B1 Dimer Compounds

| Compound | Dimer Structure |
| --- | --- |
| 19-B1-1 to 19-B1-10 | (structure shown, n = 1-10) |
| 20-B1-1 to 20-B1-10 | (structure shown, n = 1-10) |
| 21-B1-1 to 21-B1-10 | (structure shown, n = 1-10) |
| 22-B1-1 to 22-B1-10 | (structure shown, n = 1-10) |

TABLE 3-continued
Avermectin B1 Dimer Compounds
| Compound | Dimer Structure |
|---|---|
| 23-B1-1 to 23-B1-10 | 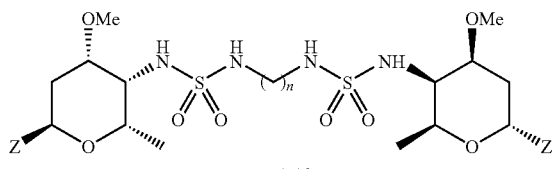<br>n = 1-10 |
| 24-B1 | 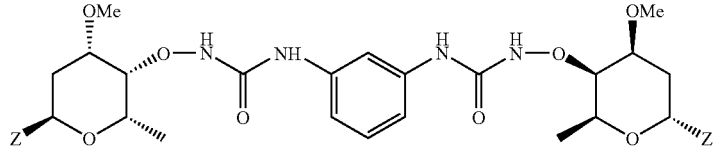 |
| 25-B1 | 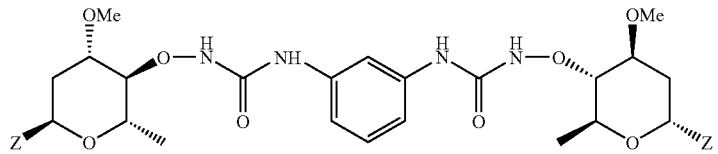 |
| 26-B1 | 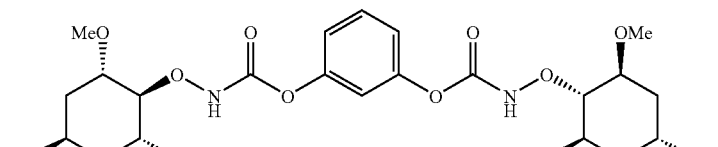 |
| 27-B1 | 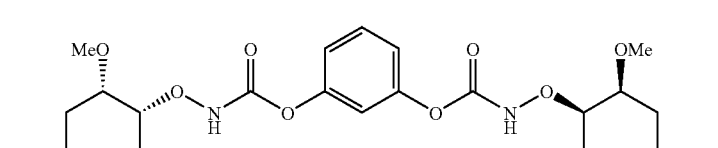 |
| 28-B1-1 to 28-B1-10 | 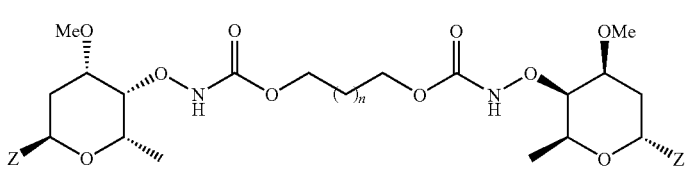<br>n = 1-10 |
| 29-B1-1 to 29-B1-10 | 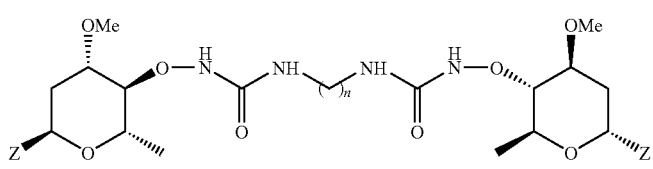<br>n = 1-10 |

TABLE 3-continued

Avermectin B1 Dimer Compounds

| Compound | Dimer Structure |
|---|---|
| 30-B1-2 to 30-B1-10 | 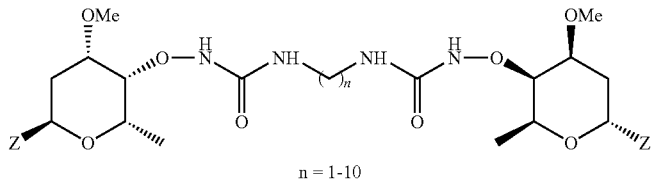<br>n = 1-10 |
| 31-B1-1 to 31-B1-10 | 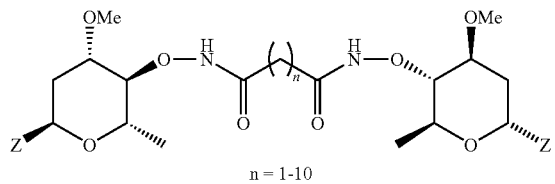<br>n = 1-10 |
| 32-B1-1 to 32-B1-10 | 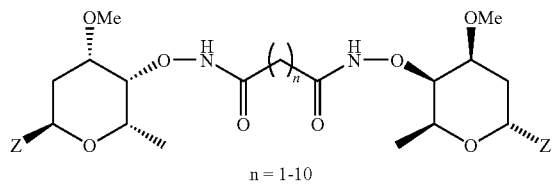<br>n = 1-10 |
| 33-B1-1 to 33-B1-10 | 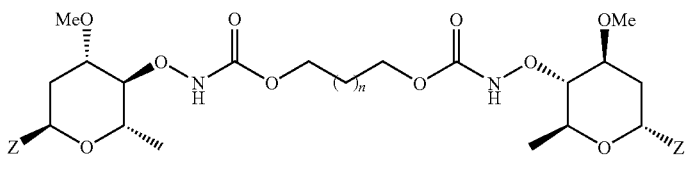<br>n = 1-10 |

One embodiment of the second object of the invention provides a composition useful for the treatment or prevention of a parasitic infection in an animal which comprises an inert carrier and an effective amount of a compound of formula (I).

The invention also provides compositions useful for combating or controlling pests and for protecting crops, growing plants, plant propagation material, and wood-containing material, or material derived from wood from infestation by pests, comprising a pesticidally effective amount of a compound of formula (I), or an agriculturally acceptable salt thereof, in combination with an agriculturally acceptable carrier.

One embodiment of the third object of the invention provides for a method for the treatment or prevention of parasitic infections and infestations in or on an animal, which comprises administering an effective amount of a compound of formula (I) to the animal in need thereof.

One embodiment of the fourth object of the invention provides for a method for controlling pests on plants or plant propagation material, which comprises treating the plant or plant propagation material, or the soil in which the infected plant grows, with an effective amount of a compound of formula (I).

In still another embodiment of the invention, a method is provided for the treatment or prevention of a parasitic infestation at a locus, which comprises administering or applying a parasiticidally effective amount of a compound of formula (I), or pharmaceutically acceptable salts thereof, to the locus. With respect to animal health applications, "locus" is intended to mean a habitat, breeding ground, area, material or environment in which a parasite is growing or may grow, including in or on an animal.

Still further embodiments of the objects of the invention will become apparent as described herein.

The compounds of formula (I) are prepared by the application or adaptation of known methods (i.e. methods heretofore used or described in the chemical literature); or methods described in one or more of U.S. Pat. Nos. 4,199,569; 4,310,519; 4,423,209; 4,427,663; 4,457,920, 4,806,527; 4,831,016; 4,855,317; 4,859,657; 4,871,719; 4,873,224; 4,874,749; 4,895,837; 4,906,619, 4,920,148; 4,963,582; 4,973,711; 4,978,677; 5,015,630, 5,023,241, 5,030,622; 5,055,454; 5,055,596; 5,057,499; 5,077,308; 5,089,490; 5,162,363; 5,169,839; 5,208,222; 5,244,879; 5,262,400; 5,830,875; 7,250,402; and EP 0 214 731, all of which are incorporated herein by reference in their entirety. It will be appreciated by persons skilled in the art that the order of synthetic transformations employed may be varied, and will depend on factors such as the nature of other functional groups present in a particular substrate, the availability of key intermediates, and the protecting group strategy to be adopted.

In one embodiment of the invention, compounds of formula (I) wherein $R_9$ and $R_{10}$ are oxygen or $NR_{11}$, and L is an alkylene linker may be prepared according to the method described in Scheme 1.

Scheme 1.
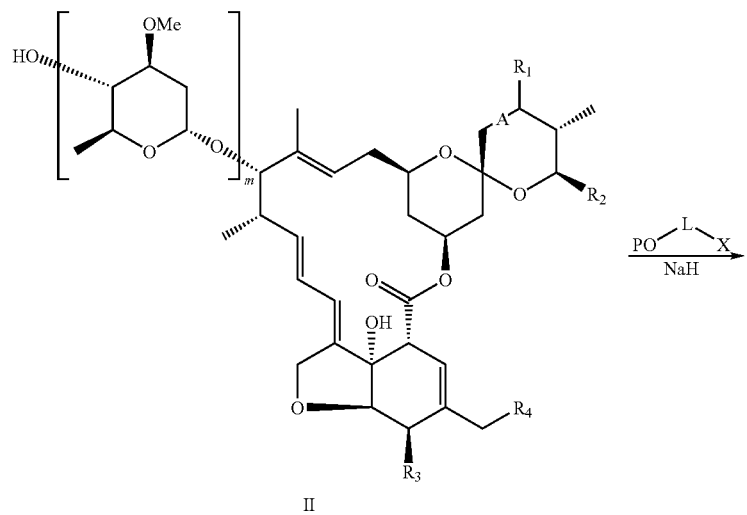
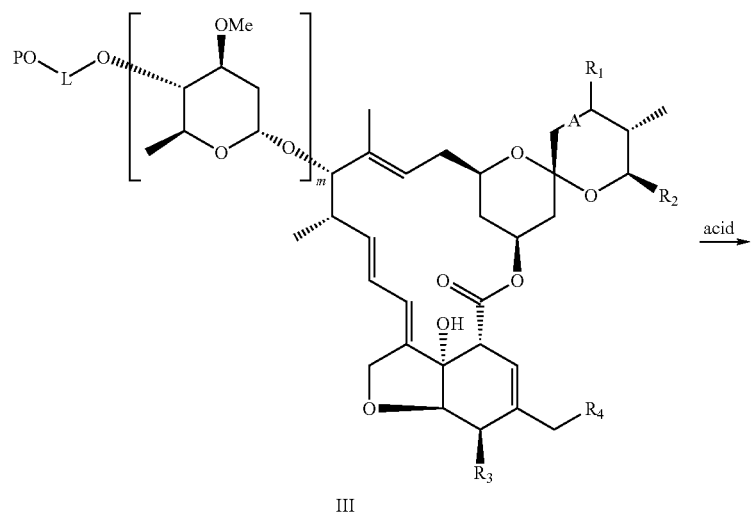
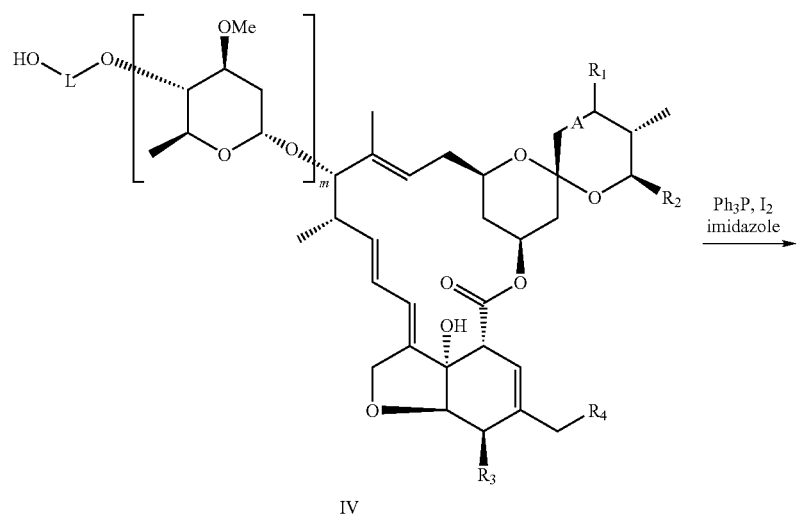

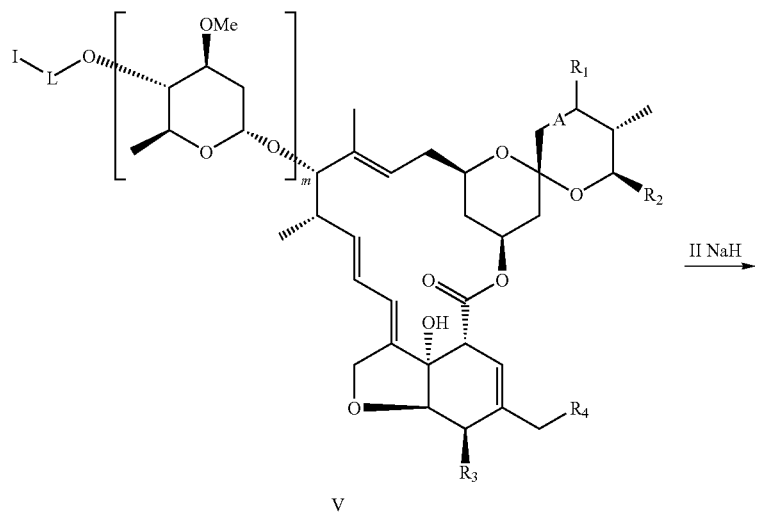

V

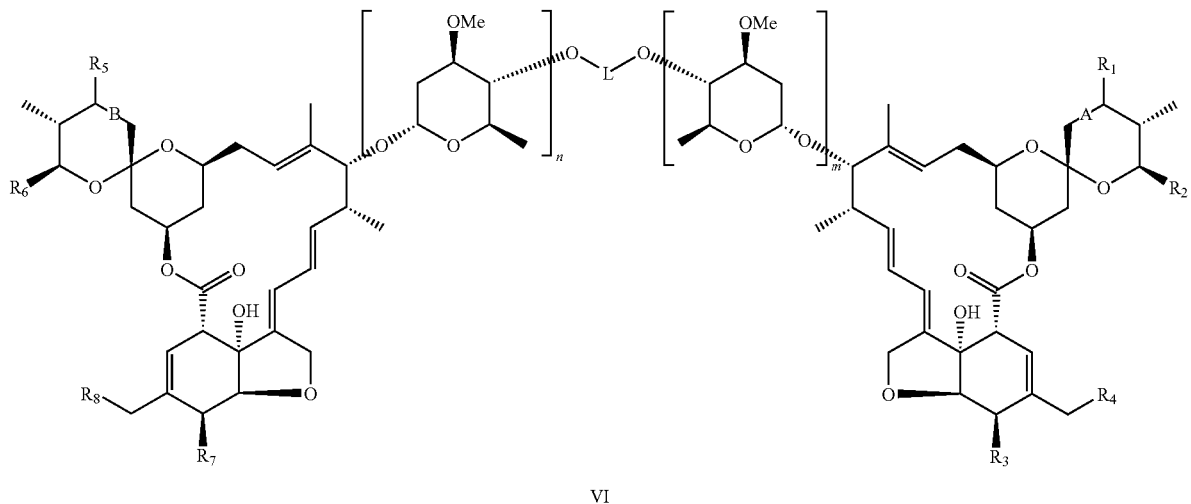

VI

Avermectin and milbemycin derivatives may be alkylated, for example, by treating the 13, 4'- or 4"-hydroxy avermectin compound (II) with a base such as a metal hydride in an appropriate solvent, followed by addition of linker molecule with an appropriate leaving group (X), where P is a protecting group.

Removal of the terminal protecting group P may be followed by conversion of the resultant alcohol to an appropriate leaving group, such as a halide or sulfonate ester. Displacement of the leaving group may be achieved via treatment with a second 13-, 4'- or 4"-hydroxy avermectin/milbemycin derivative (II) in the presence of a base such as a metal hydride to provide the desired dimeric avermectin/milbemycin derivative (VI).

In another embodiment of the first object of the invention, compounds of formula (I) wherein $R_9$ and $R_{10}$ are —$NR_{11}C(O)$—, and L is an alkylene linker may be prepared according to the method described in Scheme 2.

Scheme 2.
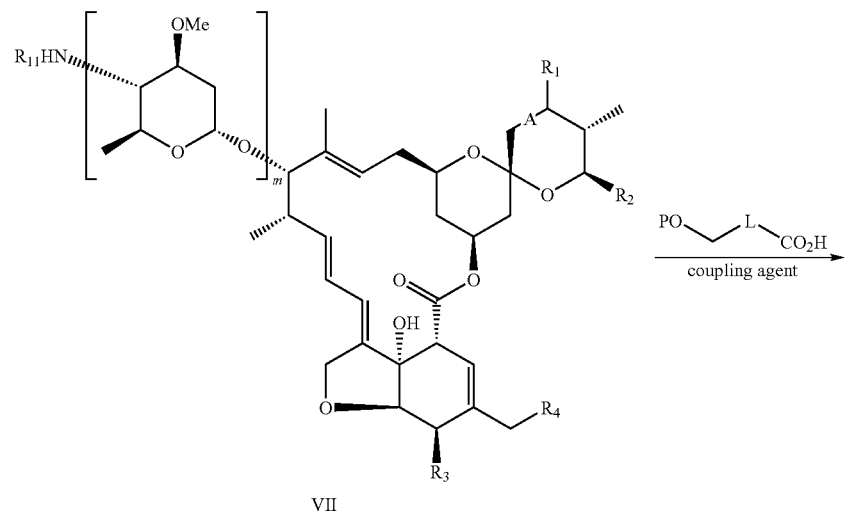
VII
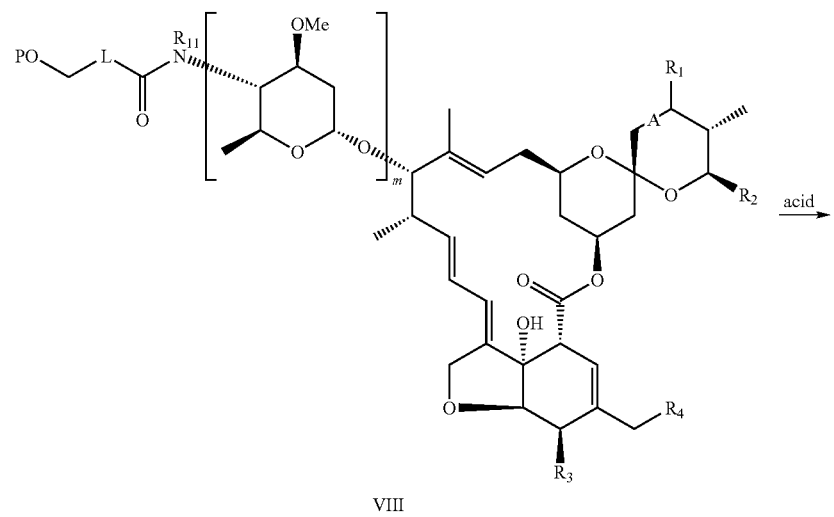
VIII
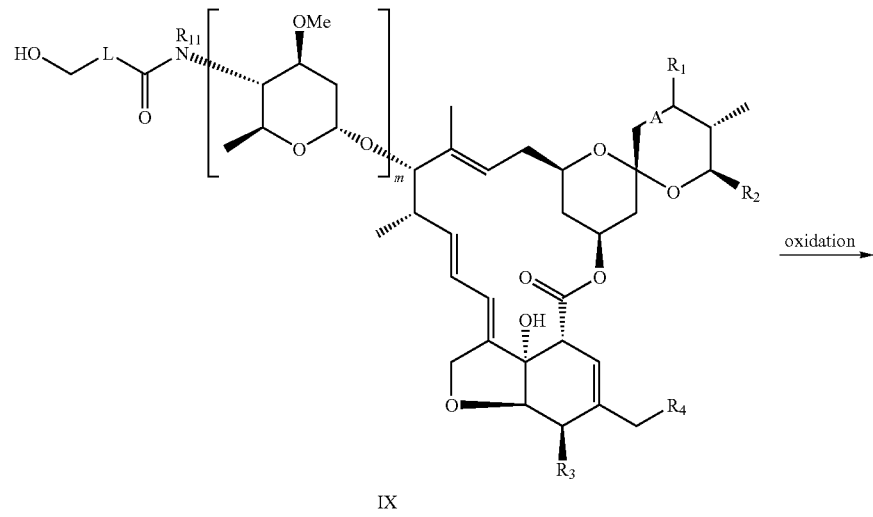
IX

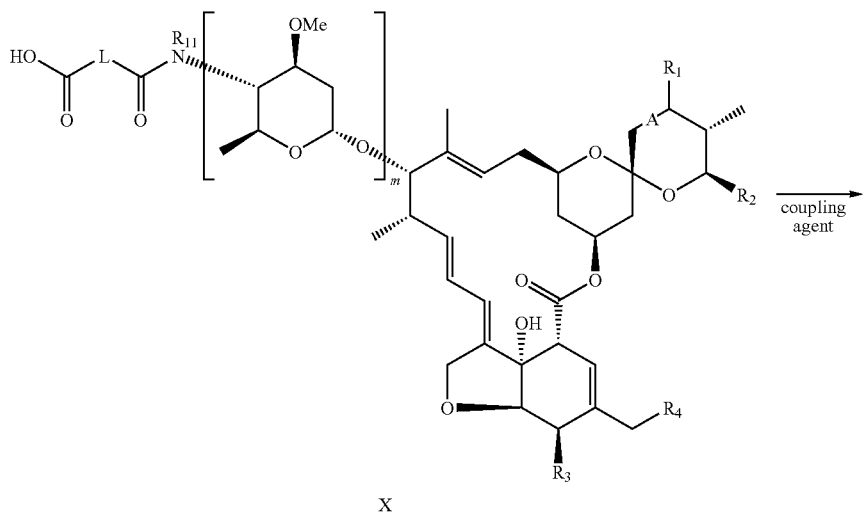

X

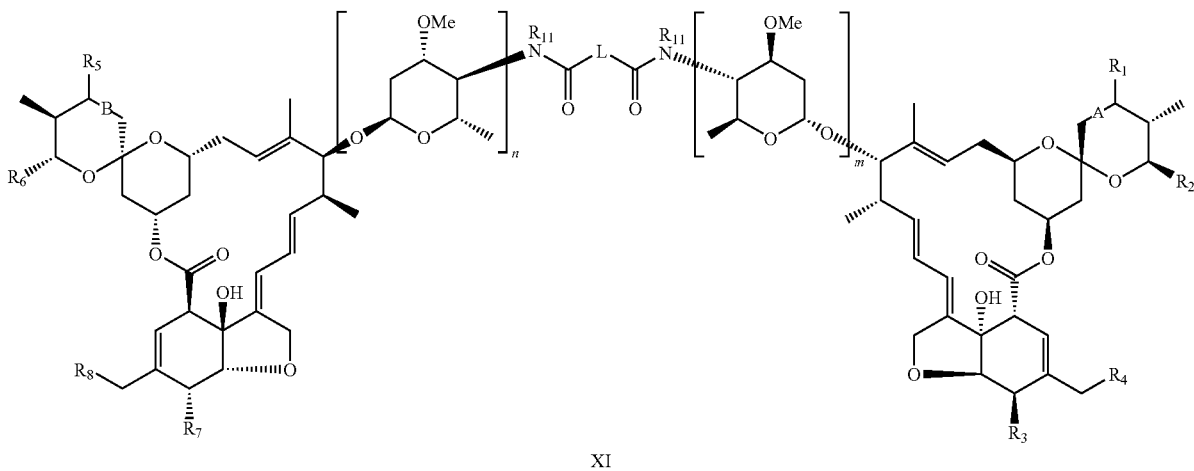

XI

Avermectin/milbemycin derivatives may be acylated, for example, by treating the 13-, 4'- or 4"-amino compound (VII) with a linker chain L terminating with an acid halide or an acid, along with an appropriate activating agent such as a known peptide coupling agent including, but not limited to, a carbodiimide coupling agent, a phosphonium or uronium coupling agents and the like, to generate (VIII).

Removal of the terminal protecting group P may be followed by oxidation of the alcohol to a carboxylic acid. Coupling of the acid (X) with a second 13-, 4'- or 4"-amino derivative (VII) may be performed using an appropriate activating agent to provide the desired dimeric avermectin/milbemycin derivative (XI).

In a still another embodiment of the first object of the invention, compounds of formula (I) wherein $R_9$ and $R_{10}$ are —$NR_{11}C(O)O$—, and L is an alkylene linker may be prepared according to the method described in Scheme 3.

Scheme 3.
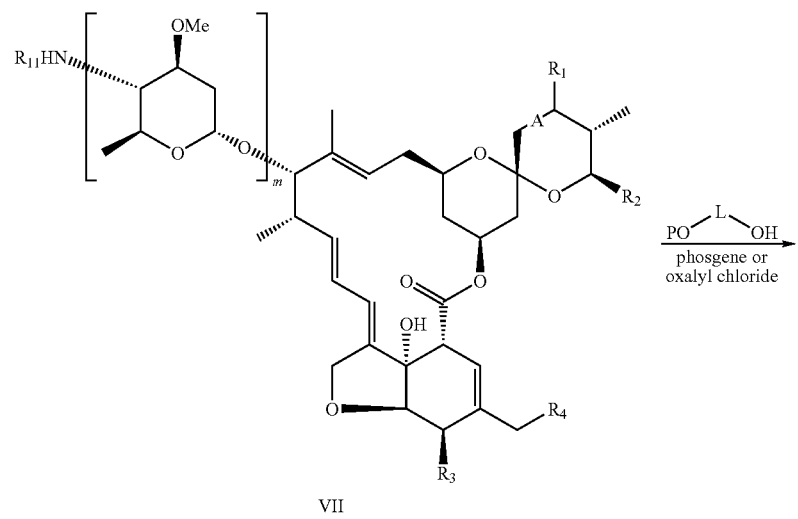
VII
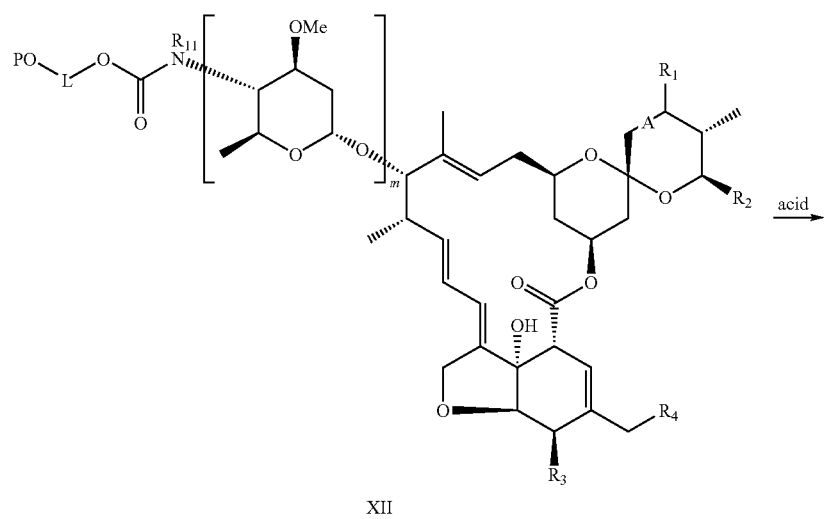
XII
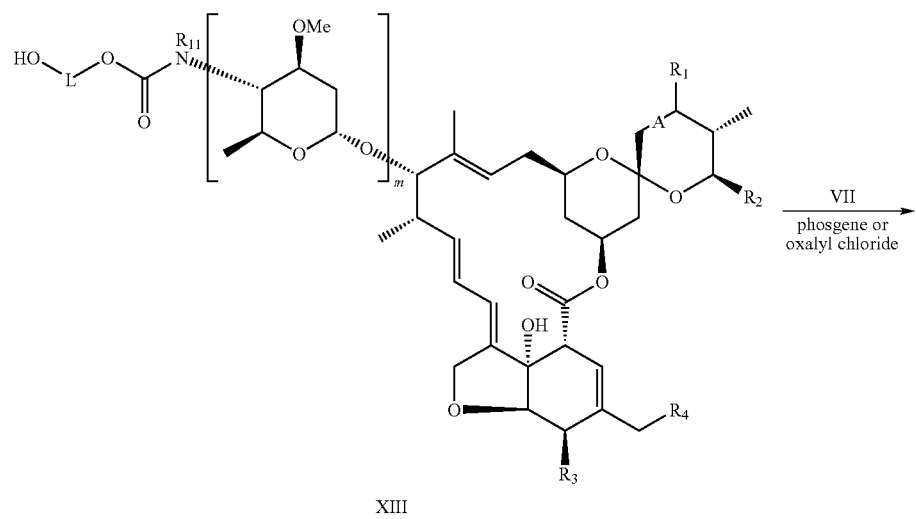
XIII

-continued

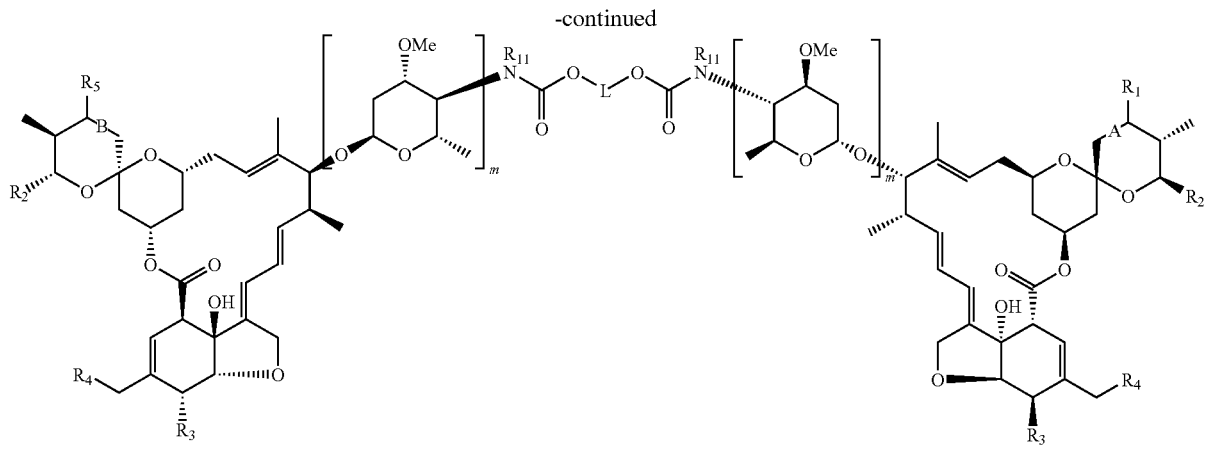

XIV

Avermectin/milbemycin derivatives may be converted into their corresponding carbamates, for example, by treating the 13-, 4'- or 4"-amino compound (VII) with an agent such as triphosgene or oxalyl chloride in the presence of an appropriate linker molecule containing an alcohol functionality to generate a carbamate (XII).

Removal of the protecting group P may be followed by treatment of the alcohol with a second 13-, 4'- or 4"-amino derivative (VII) in the presence of triphosgene or oxalyl chloride to provide the desired dimeric avermectin/milbemycin derivative (XIV).

In a still another embodiment of the first object of the invention, compounds of formula (I) wherein $R_9$ and $R_{10}$ are oxygen, and L is an arylene linker may be prepared according to the method described in Scheme 4.

Scheme 4.

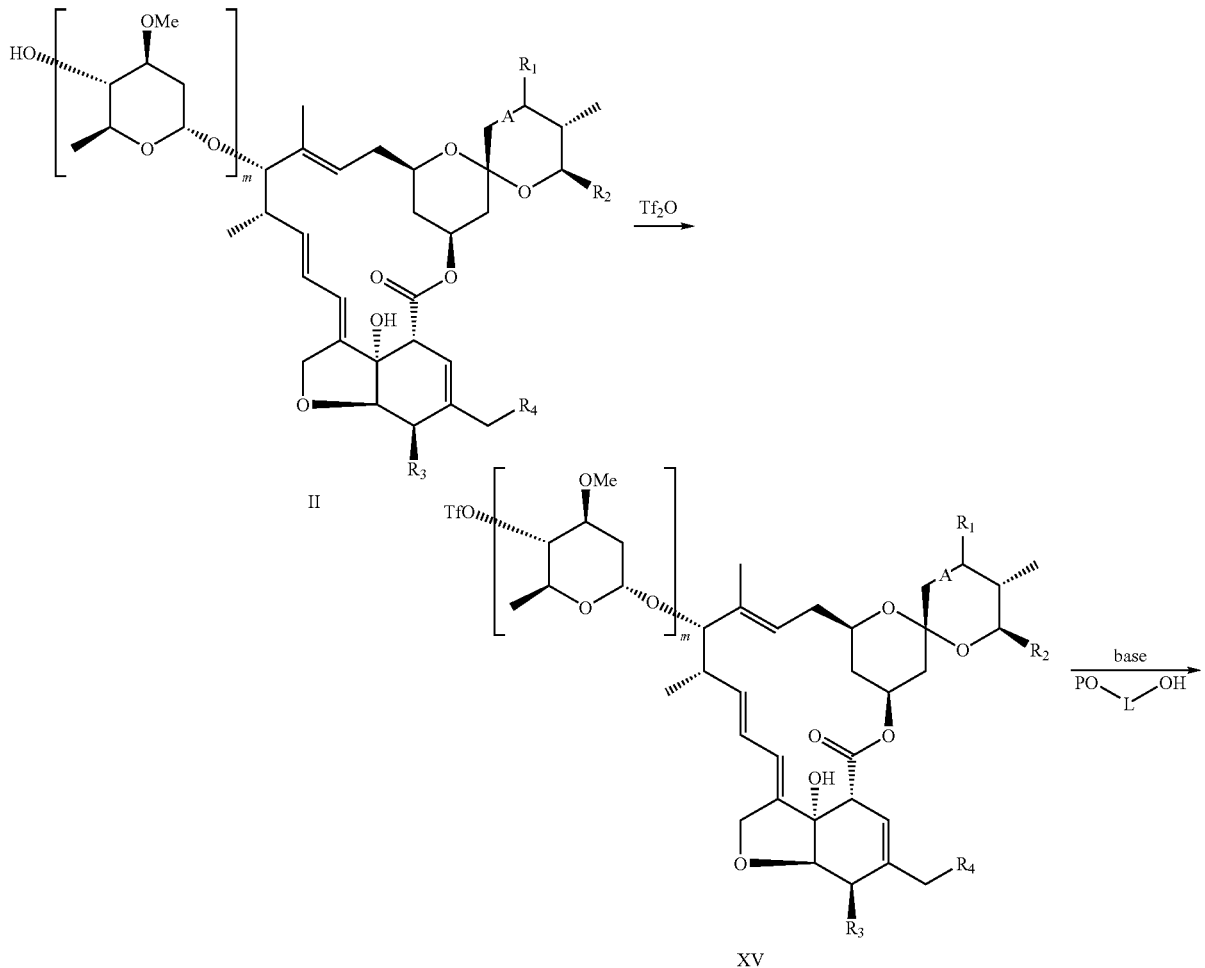

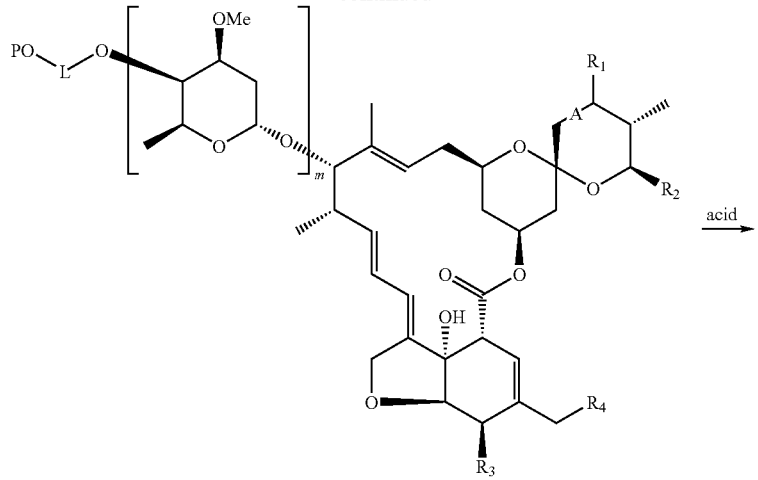

XVI

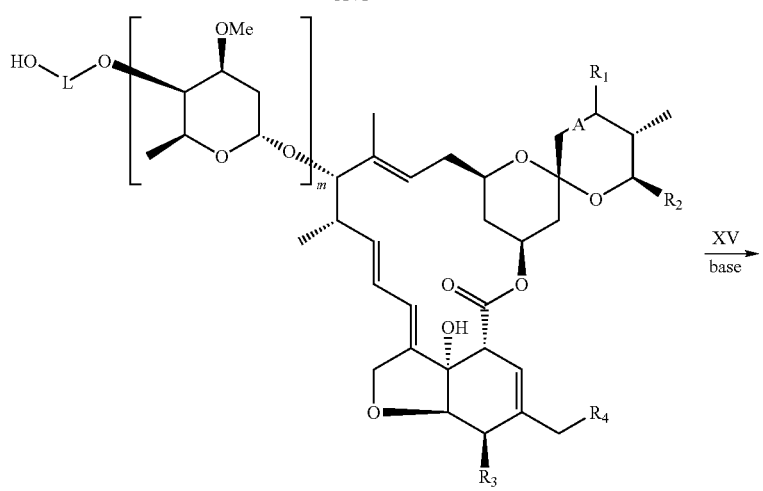

XVII

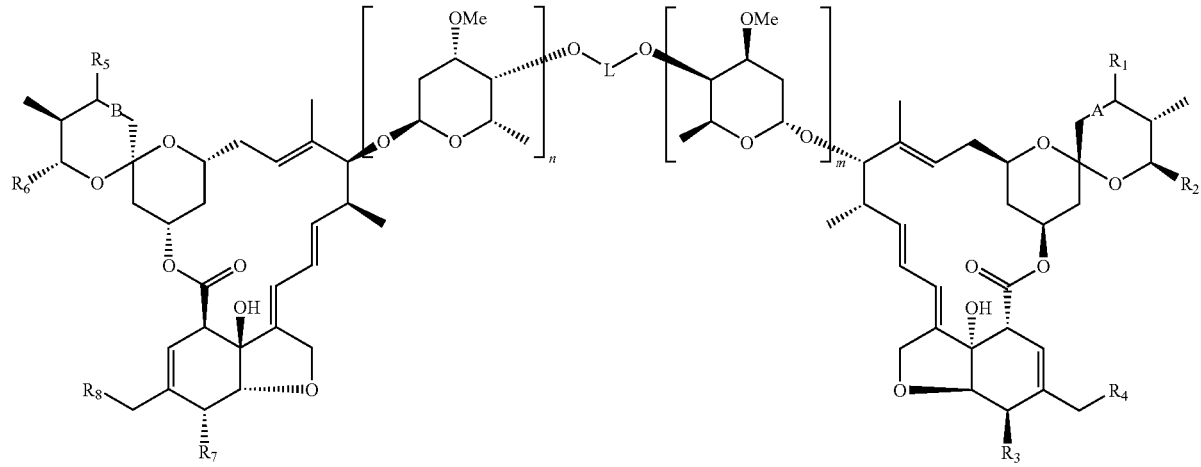

XVIII

Avermectin/milbemycin derivatives may be converted into their corresponding triflates (XV), for example, by treating the 13-, 4'- or 4"-hydroxy avermectin compound (II) with an agent such as trifluoromethanesulfonic anhydride. The triflate intermediate (XV) may then be treated with an appropriate aryl linker molecule containing a phenol functionality in the presence of a base to generate an aryl ether (XVI).

Removal of the protecting group may generate a terminal phenol (XVII), which in turn may be coupled to a second 13-, 4'- or 4"-O-triflate-avermectin/milbemycin (XV) to provide the desired dimeric avermectin/milbemycin derivative (XVIII).

Scheme 5 shows another embodiment of the invention for the preparation of compounds of formula (I), where $R_9$ and $R_{10}$ are —NHC(O)— or —NHC(=O)O—, A, $R_1$, $R_2$, $R_3$ and $R_4$ are as defined above for formula (I), and L is a $C_1$-$C_{20}$ alkylene linker.

apparent to those of skill in the art that alternate solvents/reagents known in the art for the reaction of amine nucleophiles with chloroformate and acyl halide compounds may be

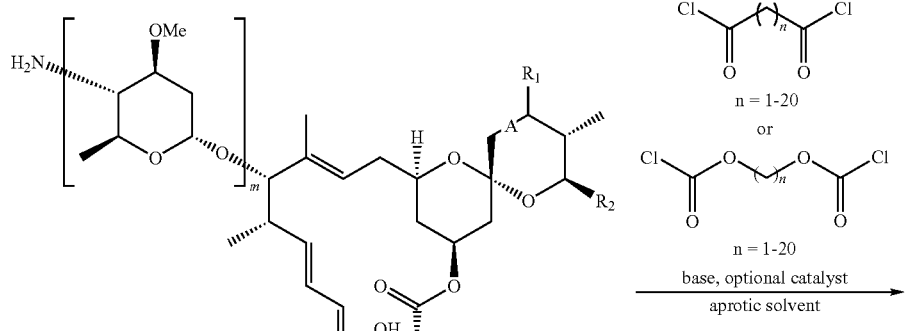

Scheme 5

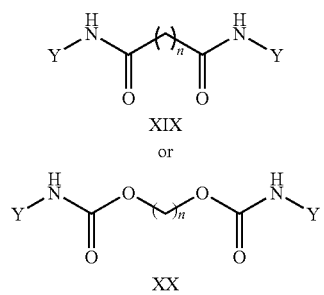

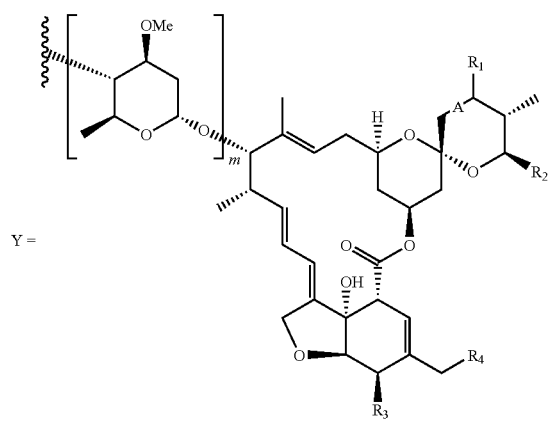

VIIa
4'-, 4"- or 13-amino avermectin or milbemycin derivative

4'-, 4"- or 13-amino avermectin or milbemycin derivative VIIa is reacted with a bis-acyl halide or bis-chloroformate in the presence of a base such as diisopropylethylamine and optionally with a catalyst (e.g. dimethylaminopyridine) in a suitable aprotic solvent, such as tetrahydrofuran, to provide the desired dimer compounds XIX and XX. In the embodiment where $R_3$ is a hydroxyl group, protection of the hydroxyl with a suitable protecting group may be required. It will be used. Furthermore, it will be apparent to those of skill in the art that a variety of hydroxyl protecting groups as taught in Greene, et al., *Protective Groups in Organic Synthesis*, John Wiley and Sons, Third Edition, 1999, may be used.

Scheme 6 below shows another embodiment of the invention for the preparation of dimer compounds of formula (I) where $R_9$ and $R_{10}$ are —$NR_{11}C(=O)NR_{11}$—, A, $R_1$, $R_2$, $R_3$ and $R_4$ are as defined for formula (I) above, and L is a $C_1$-$C_{20}$ alkylene linker.

Scheme 6

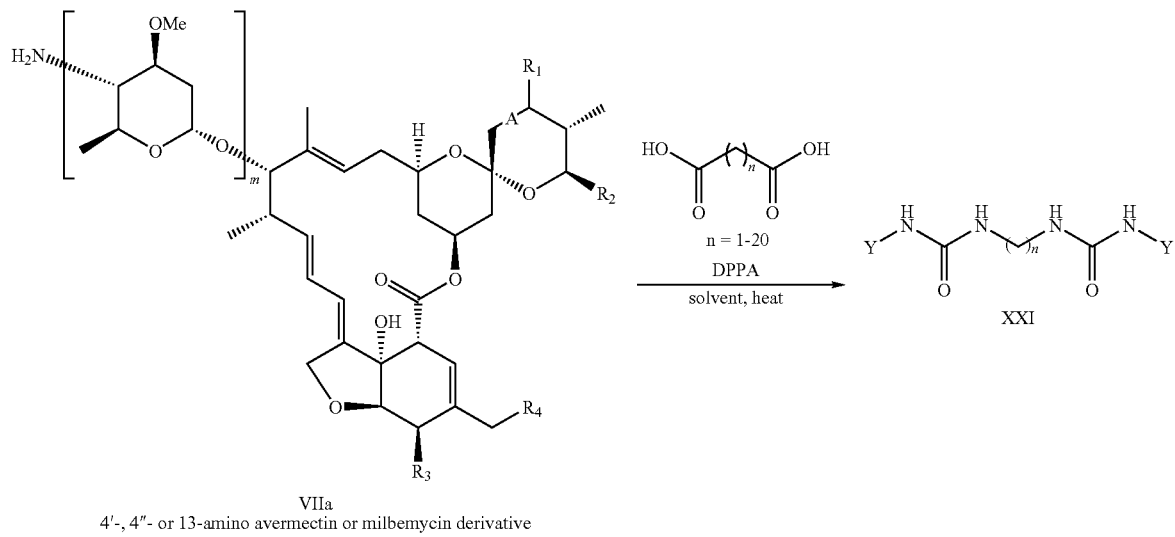

VIIa
4'-, 4"- or 13-amino avermectin or milbemycin derivative

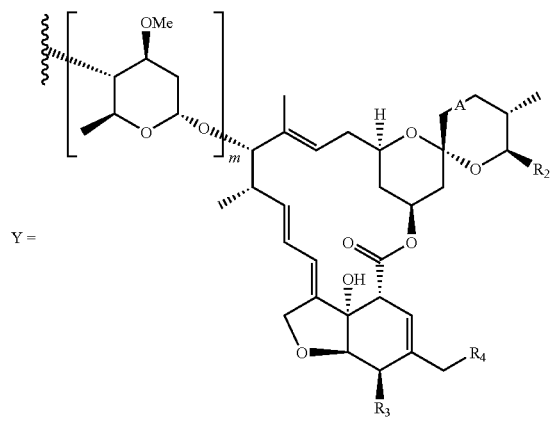

Reaction of avermectin or milbemycin derivative VIIa with a bis-carboxylic acid in the presence of diphenyl phosphoryl azide (DPPA) yields the protected urea-linked dimer XXI via a bis-isocyanate intermediate to provide the urea functionality. If required in embodiments where $R_3$ is a hydroxyl group, the hydroxyl group may be protected prior to the reaction. It will be apparent to those of skill in the art that a variety of suitable hydroxyl protecting groups as taught in Greene, et al., *Protective Groups in Organic Synthesis*, John Wiley and Sons, Third Edition, 1999, may be used. Furthermore, solvents and reaction conditions may be optimized to obtain the best yield and product purity.

Scheme 7 below depicts the formation of a 4"-hydroxylamine substituted avermectin derivative which may be utilized for the preparation of various dimer compounds of formula (I) where $R_9$ and $R_{10}$ are —ONHC(O)O— or —ONHC(O)NH—.

Scheme 7
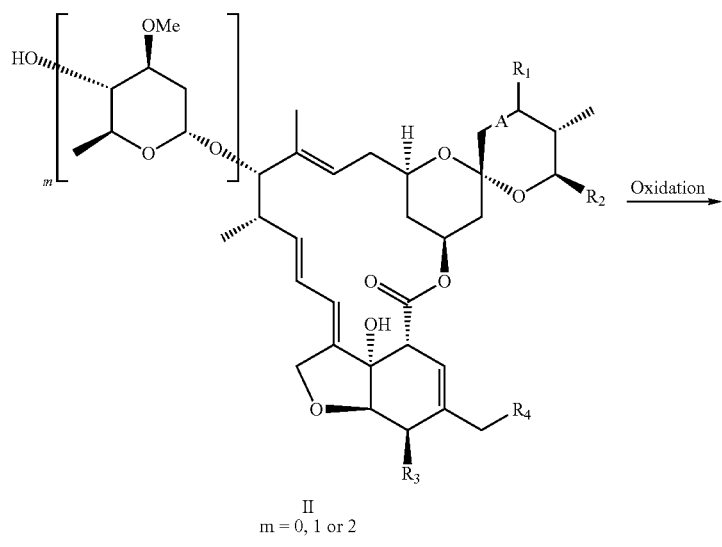
II
m = 0, 1 or 2
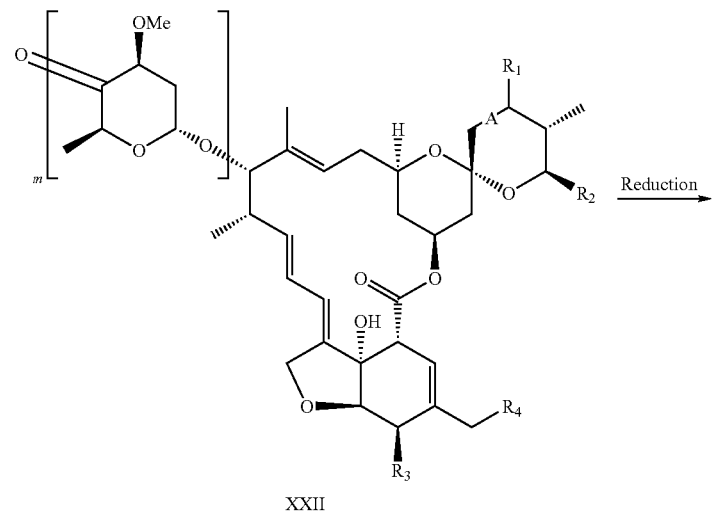
XXII
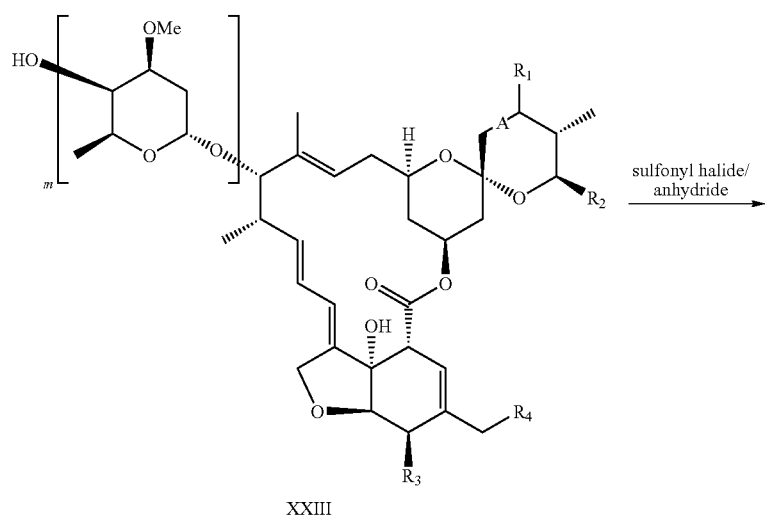
XXIII

-continued
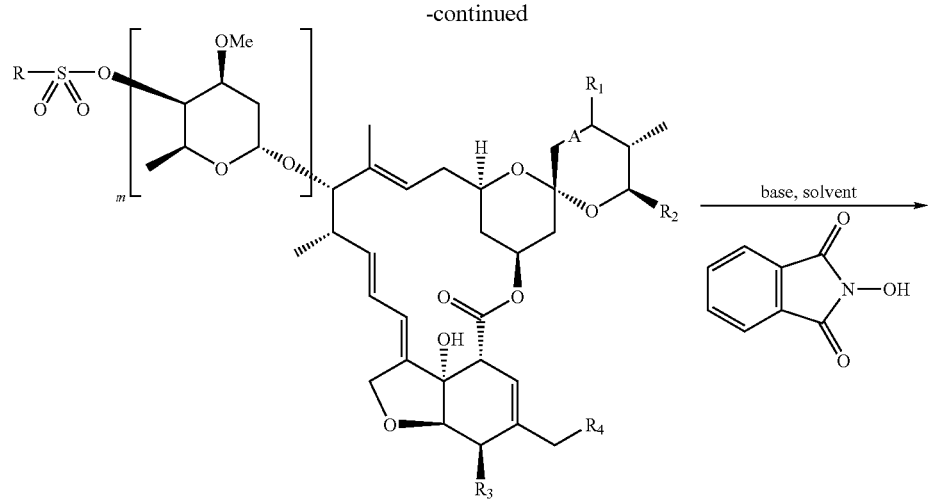
XXIV
R = alkyl, haloalkyl or aryl
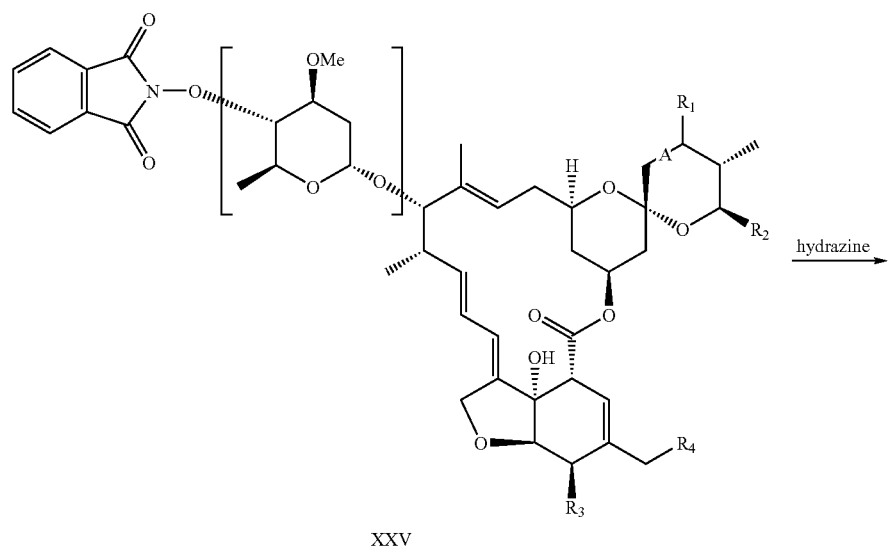
XXV
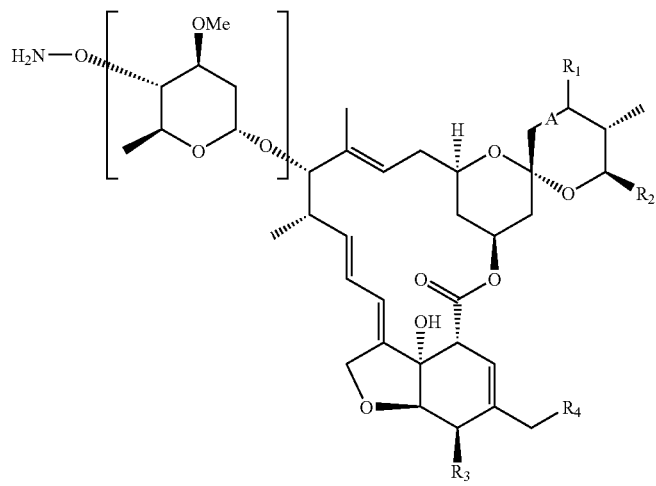
XXVI Compound II is converted to compound XXII by oxidation of the 4'-, 4"- or 13-hydroxy group using suitable oxidation conditions including, but not limited to, oxalyl chloride/ DMSO. The ketone intermediate XXII is reduced to the alcohol XXIII having the opposite stereochemical configuration using suitable reduction conditions, such as sodium borohydride in methanol, and the like. The alcohol is then converted to a suitable leaving group such as a sulfonic acid ester as in compound XXIV, where R is alkyl, haloalkyl or aryl. Compound XXIV is reacted with N-hydroxyphthalimide in the presence of a suitable base to provide the phthalimido ester XXV, which is subsequently reacted with hydrazine to provide the 4'-, 4"- or 13-aminooxy derivative XXVI. In embodiments where $R_3$ is a hydroxyl group, the 5-hydroxyl group may be protected with a suitable protecting group to avoid reaction at this position. Removal of the protecting group at the end of the sequence provides the desired dimer compound with a 5-OH substituent.

Scheme 8 below shows the formation of an avermectin or milbemycin dimer compound of formula (I) wherein $R_9$ and $R_{10}$ are —ONHC(O)O—, A, $R_1$, $R_2$, $R_3$ and $R_4$ are as defined for the compound of formula (I), and L is an phenylene linker.

Scheme 8

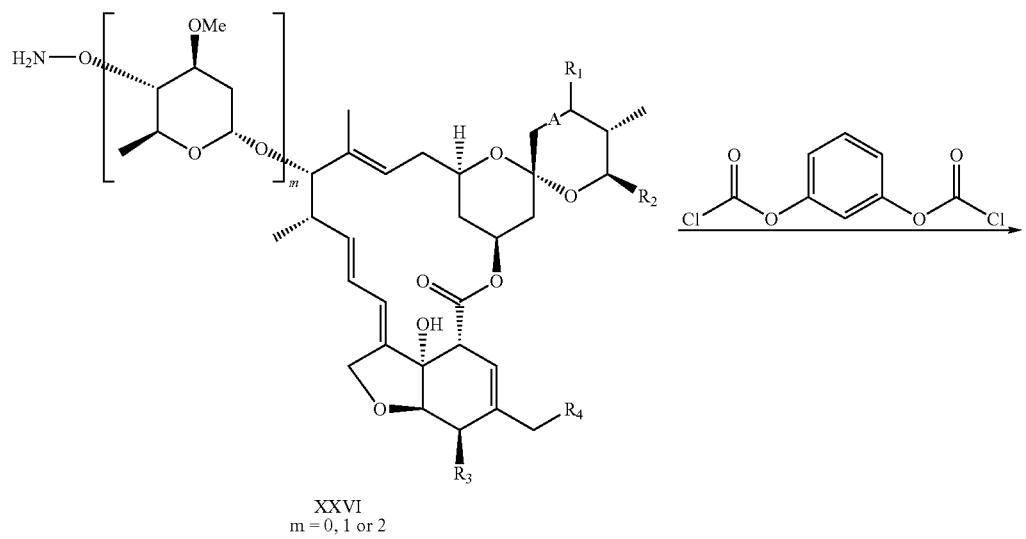

XXVI
m = 0, 1 or 2

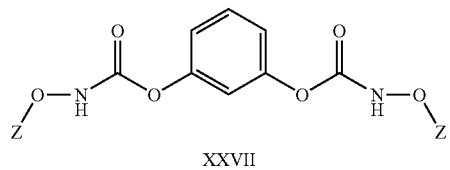

XXVII

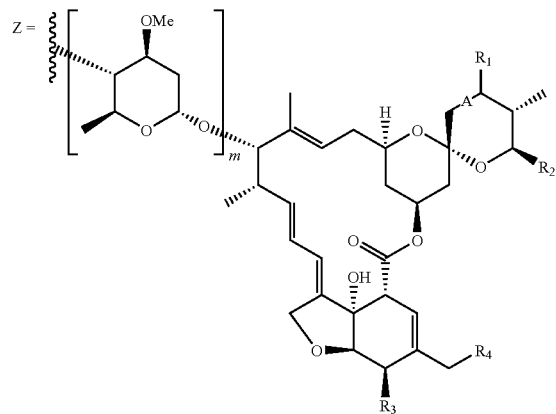

Reaction of 4'-, 4"- or 13-aminooxy derivative XXVI with a phenyl bis-chloroformate reagent provides the desired dimer compound XXVII. As discussed above for Scheme 7, in some embodiments where $R_3$ is a hydroxyl group, this hydroxyl group may be suitably protected to avoid reaction at this position. It will be apparent to those of skill in the art that substitution of the chloroformate reagent with a different reagent such as a phenyl bis-acylchloride or phenyl bis-isocyanate reagent will provide the corresponding dimer compounds where $R_9$ and $R_{10}$ are —ONHC(O)— or —ONHC(O)NH—.

Scheme 9 depicts the formation of an avermectin or milbemycin compound of formula (I), where $R_9$ and $R_{10}$ are —ONHC(O)NH— and L is an alkylene linker having the opposite stereochemistry at the 4'-, 4"- or 13 position. In this scheme, compound II is converted to the sulfonyl ester derivative XXVIII directly with a suitable sulfonyl halide or sulfonyl anhydride reagent. Reaction with phthalmide in the presence of a suitable base provides compound XXIX, which is converted to the hydroxylamine derivative upon reaction with hydrazine. Reaction of the 4'-, 4"- or 13-hydroxylamine derivative with a bis-isocyanate compound provides the desired dimer compound XXXI. It will be apparent to one of skill in the art that substitution of the bis-isocyanate compound with another reactive linker reagent will result in the corresponding dimer compounds having the desired stereochemistry at the 4'-, 4"- or 13-position. For example, use of a bis-chloroformate or bis-acylhalide reagent will provide dimer compounds where $R_9$ and $R_{10}$ are —ONHC(O)O— or —ONHC(O)NH—.

Scheme 9

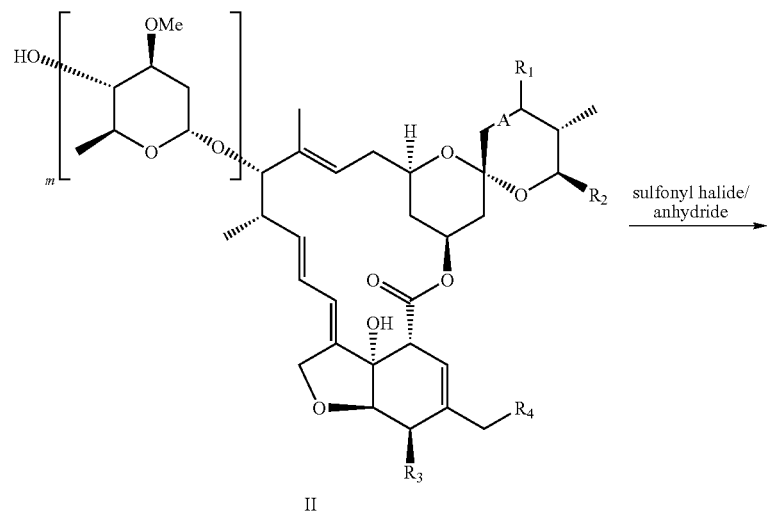

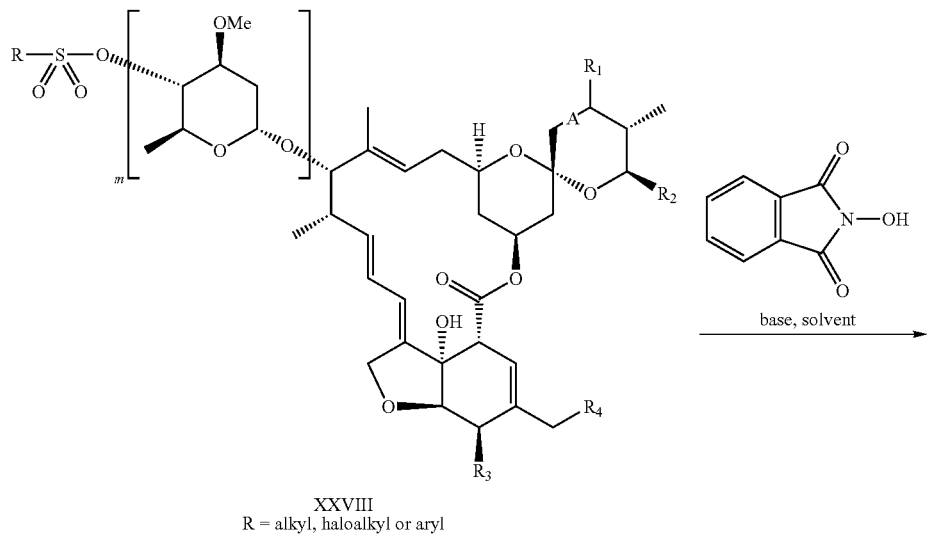

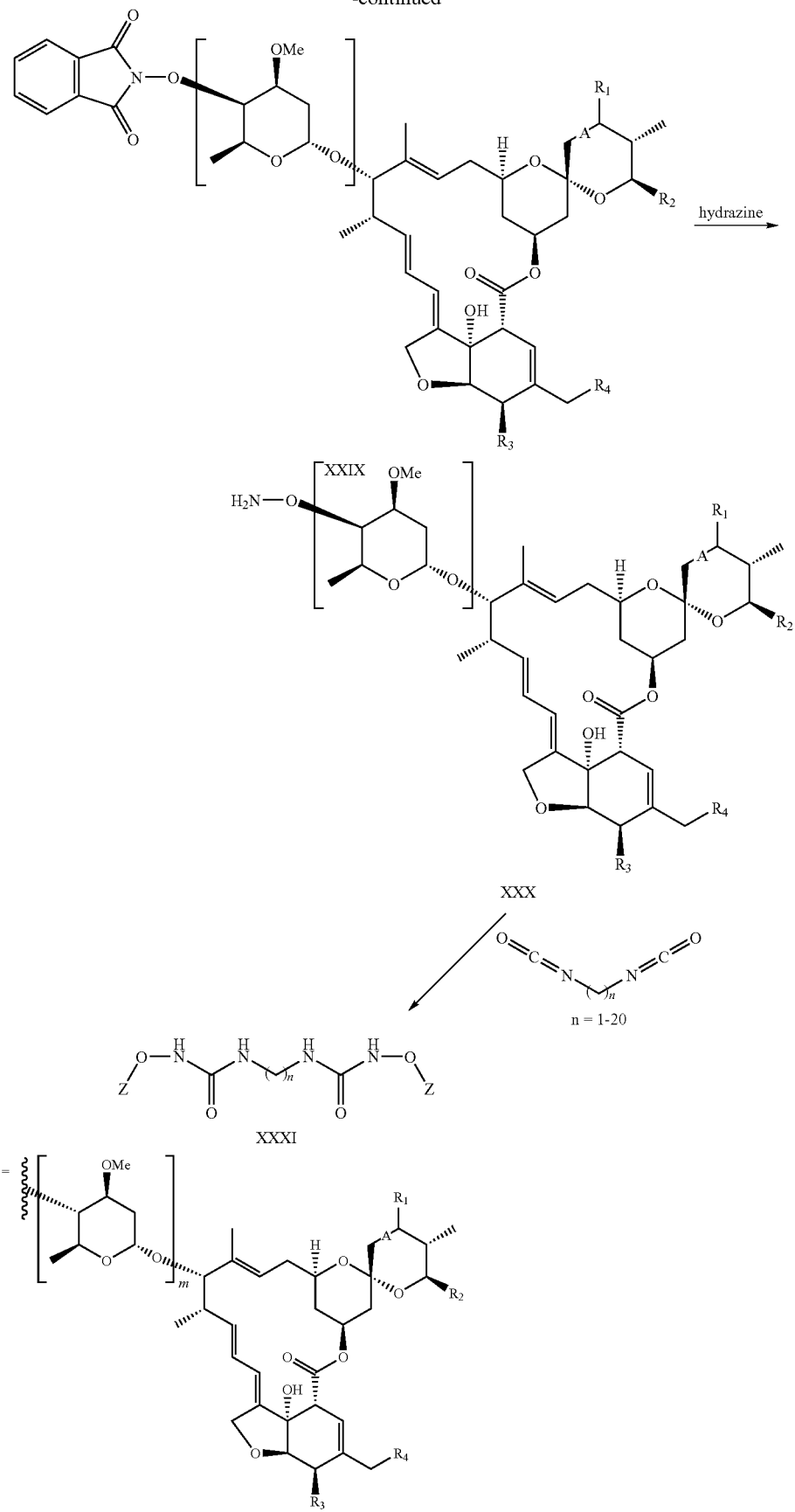

Terms used herein will have their customary meaning in the art unless specified otherwise. The organic moieties mentioned in the definitions of the variables of formula (I) are—like the term halogen—collective terms for individual listings of the individual group members. The prefix $C_n$-$C_m$ indicates in each case the possible number of carbon atoms in the group.

The term "animal" is used herein to include all mammals, birds and fish and also include all vertebrate animals, including humans. It also includes an individual animal in all stages of development, including embryonic and fetal stages.

The term "plant propagation material" refers to any parts of a plant which are propagable. In general, a plant propagation material includes the product of the ripened ovule of gymnosperm and angiosperm plants which occurs after fertilization and some growth within the mother plant and includes seed, fruits, spurious fruits, infructescences and also rhizomes (rootstocks), corms, tubers, bulbs and scions.

The term "plant propagation material" is to be understood to denote all the generative parts of the plant such as seeds and vegetative plant material such as cuttings and tubers (e.g. potatoes), which can be used for the multiplication of the plant. This includes seeds, roots, fruits, tubers, bulbs, rhizomes, shoots, sprouts and other parts of plants. Seedlings and young plants, which are to be transplanted after germination or after emergence from soil, may also be included. These plant propagation materials may be treated prophylactically with a plant protection compound either at or before planting or transplanting.

The term "alkyl" refers to saturated straight, branched, cyclic, primary, secondary or tertiary hydrocarbons, including those having 1 to 20 atoms. In some embodiments, alkyl groups will include $C_1$-$C_{12}$, $C_1$-$C_{10}$, $C_1$-$C_8$, $C_1$-$C_6$ or $C_1$-$C_4$ alkyl groups. Examples of $C_1$-$C_{10}$ alkyl include, but are not limited to, methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, 2-ethylhexyl, nonyl and decyl and their isomers. $C_1$-$C_4$-alkyl means for example methyl, ethyl, propyl, 1-methylethyl, butyl, 1-methylpropyl, 2-methylpropyl or 1,1-dimethylethyl.

Cyclic alkyl groups, which are encompassed by alkyl, may be referred to as "cycloalkyl" and include those with 3 to 10 carbon atoms having single or multiple condensed rings. In some embodiments, cycloalkyl groups include $C_4$-$C_7$ or $C_3$-$C_4$ cyclic alkyl groups. Non-limiting examples of cycloalkyl groups include adamantyl, cyclopropyl, cyclobutyl, cyclopentyl, cyclohexyl, cycloheptyl, cyclooctyl and the like.

The alkyl and cycloalkyl groups described herein can be unsubstituted or substituted with one or more moieties selected from the group consisting of alkyl, halo, haloalkyl, hydroxyl, carboxyl, acyl, acyloxy, amino, alkyl- or dialkylamino, amido, arylamino, alkoxy, aryloxy, nitro, cyano, azido, thiol, imino, sulfonic acid, sulfate, sulfonyl, sulfanyl, sulfinyl, sulfamonyl, ester, phosphonyl, phosphinyl, phosphoryl, phosphine, thioester, thioether, acid halide, anhydride, oxime, hydrozine, carbamate, phosphonic acid, phosphate, phosphonate, or any other viable functional group that does not inhibit the biological activity of the compounds of the invention, either unprotected, or protected as necessary, as known to those skilled in the art, for example, as taught in Greene, et al., *Protective Groups in Organic Synthesis*, John Wiley and Sons, Third Edition, 1999, hereby incorporated by reference The term "alkenyl" refers to both straight and branched carbon chains which have at least one carbon-carbon double bond. In some embodiments, alkenyl groups may include $C_2$-$C_{20}$ alkenyl groups. In other embodiments, alkenyl includes $C_2$-$C_{12}$, $C_2$-$C_{10}$, $C_2$-$C_8$, $C_2$-$C_6$ or $C_2$-$C_4$ alkenyl groups. In one embodiment of alkenyl, the number of double bonds is 1-3, in another embodiment of alkenyl, the number of double bonds is one or two. Other ranges of carbon-carbon double bonds and carbon numbers are also contemplated depending on the location of the alkenyl moiety on the molecule. "$C_2$-$C_{10}$-alkenyl" groups may include more than one double bond in the chain. Examples include, but are not limited to, ethenyl, 1-propenyl, 2-propenyl, 1-methyl-ethenyl, 1-butenyl, 2-butenyl, 3-butenyl, 1-methyl-1-propenyl, 2-methyl-1-propenyl, 1-methyl-2-propenyl, 2-methyl-2-propenyl; 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

"Alkynyl" refers to both straight and branched carbon chains which have at least one carbon-carbon triple bond. In one embodiment of alkynyl, the number of triple bonds is 1-3; in another embodiment of alkynyl, the number of triple bonds is one or two. In some embodiments, alkynyl groups include from $C_2$-$C_{20}$ alkynyl groups. In other embodiments, alkynyl groups may include $C_2$-$C_{12}$, $C_2$-$C_{10}$, $C_2$-$C_8$, $C_2$-$C_6$ or $C_2$-$C_4$ alkynyl groups. Other ranges of carbon-carbon triple bonds and carbon numbers are also contemplated depending on the location of the alkenyl moiety on the molecule. For example, the term "$C_2$-$C_{10}$-alkynyl" as used herein refers to a straight-chain or branched unsaturated hydrocarbon group having 2 to 10 carbon atoms and containing at least one triple bond, such as ethynyl, prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl or 4-methylpent-2-yn-5-yl and the like.

"Aryl" refers to a monovalent aromatic carbocyclic group of from 6 to 14 carbon atoms having a single ring or multiple condensed rings. In some embodiments, aryl groups include $C_6$-$C_{10}$ aryl groups. Aryl groups include, but are not limited to, phenyl, biphenyl, naphthyl, tetrahydronaphtyl, phenylcyclopropyl and indanyl. Aryl groups may be unsubstituted or substituted by one or more moieties selected from halogen, cyano, nitro, hydroxy, mercapto, amino, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy, haloalkenyloxy, haloalkynyloxy, cycloalkoxy, cycloalkenyloxy, halocycloalkoxy, halocycloalkenyloxy, alkylthio, haloalkylthio, cycloalkylthio, halocycloalkylthio, alkylsulfinyl, alkenylsulfinyl, alkynyl-sulfinyl, haloalkylsulfinyl, haloalkenylsulfinyl, haloalkynylsulfinyl, alkylsulfonyl, alkenylsulfonyl, alkynylsulfonyl, haloalkyl-sulfonyl, haloalkenylsulfonyl, haloalkynylsulfonyl, alkylamino, alkenylamino, alkynylamino, di(alkyl)amino, di(alkenyl)-amino, di(alkynyl)amino, or trialkylsilyl.

"Heteroaryl" refers to a monovalent aromatic group of from 1 to 15 carbon atoms, preferably from 1 to 10 carbon atoms, having one or more oxygen, nitrogen, and sulfur heteroatoms within the ring, preferably 1 to 4 heteroatoms, or 1 to 3 heteroatoms. The nitrogen and sulfur heteroatoms may optionally be oxidized and the nitrogen heteroatoms may optionally be quaternized. Such heteroaryl groups can have a single ring (e.g., pyridyl or furyl) or multiple fused rings provided that the point of attachment is through a heteroaryl ring atom. Heteroaryl rings may be unsubstituted or substituted by one or more moieties as described for aryl above. Exemplary monocyclic heterocyclic groups include, but are not limited to, pyrrolyl, pyrazolyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, thienyl, oxadiazolyl, pyridyl, pyrazinyl, pyrimidinyl, pyridazinyl, triazolyl, triazinyl, and the like.

Exemplary bicyclic heteroaryl groups include, but are not limited to, indolyl, benzothiazolyl, benzoxazolyl, benzodioxolyl, benzothienyl, benzimidazolyl, benzopyranyl, indolizinyl, benzofuryl, chromonyl, coumarinyl, benzopyranyl, indazolyl, pyrrolopyridyl, quinolinyl, isoquinolinyl, quinazolinyl, quinoxalinnyl, imidazolyl, oxazolyl, isoxazolyl, isothiazolyl, pyrazolyl benzofuranyl, and benzothiophenyl. furopyridinyl (such as furo[2,3-c]pyridinyl, furo[3,2-b]pyridinyll or furo[2,3-b]pyridinyl), dihydroisoindolyl, dihydroquinazolinyl (such as 3,4-dihydro-4-oxoquinazolinyl), and the like.

Exemplary tricyclic heterocyclic groups include, but are not limited to, carbazolyl, benzidolyl, phenanthrolinyl, acridinyl, phenanthridinyl, xanthenyl and the like.

Alkoxy refers to —O-alkyl, wherein alkyl is as defined above;

Alkanoyl refers to formyl (—C(=O)H) and —C(=O)-alkyl, wherein alkyl is as defined above;

Alkanoyloxy refers to —O-alkanoyl, where alkanoyl is defined above;

Cyclo as a prefix (e.g. cycloalkyl, cycloalkenyl, cycloalkynyl) refers to a saturated or unsaturated cyclic ring structure having from three to eight carbon atoms in the ring the scope of which is intended to be separate and distinct from the definition of aryl above. In one embodiment of cyclo, the range of ring sizes is 4-7 carbon atoms; in another embodiment of cyclo the range of ring sizes is 3-4. Other ranges of carbon numbers are also contemplated depending on the location of the cyclo-moiety on the molecule;

Halogen means the atoms fluorine, chlorine, bromine and iodine. The designation of "halo" (e.g. as illustrated in the term haloalkyl) refers to all degrees of substitutions from a single substitution to a perhalo substitution (e.g. as illustrated with methyl as chloromethyl (—CH$_2$Cl), dichloromethyl (—CHCl$_2$), trichloromethyl (—CCl$_3$);

Oxo refers to carbonyl groups such as C=O.

Imino refers to —C=NH, —C=N-alkyl, —C=N-alkenyl, —C=N-alkynyl, —C=N-cycloalkyl, —C=N-aryl, or —C=N-heteroaryl, wherein alkyl, alkenyl, alkynyl, cycloalkyl, aryl and heteroaryl are as defined above.

Alkoxyimino refers to imino groups containing an alkoxy group, as indicated in (5) above, wherein the oxygen atom of the alkoxy group is attached to the nitrogen atom of the imino group.

Hydroximino refers to imino groups containing a hydroxyl group (—OH), wherein the oxygen atom of the hydroxyl group is attached to the nitrogen atom of the imino group.

Stereoisomers and Polymorphic Forms

All stereoisomers (for example, geometric isomers, optical isomers and the like) of the present compounds (including those of the salts and solvates of the compounds), such as those which may exist due to asymmetric centers on various substituents, including enantiomeric forms, rotameric forms, atropisomers, and diastereomeric forms, as well as mixtures of different stereoisomeric forms that possess the useful properties described herein are contemplated within the scope of this invention. The optically active forms can be prepared by, for example, resolution of the racemic forms by selective crystallization techniques, by synthesis from optically active precursors, by chiral synthesis, by chromatographic separation using a chiral stationary phase or by enzymatic resolution.

The compounds within the compositions of present invention may also be present in different solid forms such as different crystalline forms or in the form of an amorphous solid. The present invention encompasses different crystalline forms as well as amorphous forms of the inventive compounds.

In addition, the compounds within the compositions of the invention may exist as hydrates or solvates, in which a certain stoichiometric amount of water or a solvent is associated with the molecule in the crystalline form. The hydrates and solvates of the compounds of the invention are also the subject of the invention.

When a functional group in a compound is deemed "protected", this indicates that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis*, 3$^{rd}$ ed, (1999), Wiley, New York, N.Y.

When any variable (e.g., aryl, heteroaryl, R$_1$, etc.) occurs more than once in any constituent or formula, the definition thereof on each occurrence is independent of its definition at every other occurrence.

This application contemplates all pharmaceutically or veterinarily acceptable salt forms of the anthelmintic compounds that may be formed by combination of the compounds of the invention with a suitable acid or base, where applicable. The term "acid" contemplates all pharmaceutically or veterinary acceptable inorganic or organic acids. Inorganic acids include mineral acids such as hydrohalic acids, such as hydrobromic and hydrochloric acids, sulfuric acids, phosphoric acids and nitric acids. Organic acids include all pharmaceutically or veterinarily acceptable aliphatic, alicyclic and aromatic carboxylic acids, dicarboxylic acids tricarboxylic acids and fatty acids. Preferred acids are straight chain or branched, saturated or unsaturated $C_1$-$C_{20}$ aliphatic carboxylic acids, which are optionally substituted by halogen or by hydroxyl groups, or $C_6$-$C_{12}$ aromatic carboxylic acids. Examples of such acids are carbonic acid, formic acid, fumaric acid, acetic acid, propionic acid, isopropionic acid, valeric acid, $\alpha$-hydroxy acids, such as glycolic acid and lactic acid, chloroacetic acid, benzoic acid, methane sulfonic acid, and salicylic acid. Examples of dicarboxylic acids include oxalic acid, malic acid, succinic acid, tataric acid and maleic acid. An example of a tricarboxylic acid is citric acid. Fatty acids include all pharmaceutically or veterinary acceptable saturated or unsaturated aliphatic or aromatic carboxylic acids having 4 to 24 carbon atoms. Examples include butyric acid, isobutyric acid, sec-butyric acid, lauric acid, palmitic acid, stearic acid, oleic acid, linoleic acid, linolenic acid, and phenylsteric acid. Other acids include gluconic acid, glycoheptonic acid and lactobionic acid.

The term "base" contemplates all pharmaceutically or veterinarily acceptable inorganic or organic bases. Such bases include, for example, the alkali metal and alkaline earth metal salts, such as the lithium, sodium, potassium, magnesium or calcium salts. Organic bases include the common hydrocarbyl and heterocyclic amine salts, which include, for example, the morpholine and piperidine salts.

A pharmaceutically acceptable carrier is selected on the basis of the form of the composition which includes baits, dietary supplements, powders, shampoos, pastes, concentrated solution, suspension, microemulsion and emulsion. Compositions intended for pharmaceutical use may be prepared according to any method known in the art for the manufacture of pharmaceutical compositions. *Remington— The Science and Practice of Pharmacy* (21$^{st}$ Edition) (2005), *Goodman & Gilman's The Pharmacological Basis of Therapeutics* (11$^{th}$ Edition) (2005) and *Ansel's Pharmaceutical Dosage Forms and Drug Delivery Systems* (8$^{th}$ Edition), edited by Allen et al., Lippincott Williams & Wilkins, (2005).

The composition of the invention can be in a variety of forms which include, but are not limited to, oral formulations, injectable formulations, and topical, dermal or subdermal formulations.

In some embodiments, the composition of the invention may be in a form suitable for oral use, for example, as baits (see, e.g., U.S. Pat. No. 4,564,631 incorporated herein by reference), dietary supplements, troches, lozenges, chewables, tablets, hard or soft capsules, emulsions, aqueous or oily suspensions, aqueous or oily solutions, oral drench formulations, dispersible powders or granules, syrups or elixirs, enteric formulations or pastes. Compositions intended for oral use may be prepared according to any method known in the art for the manufacture of pharmaceutical compositions and such compositions may contain one or more agents selected from the group consisting of sweetening agents, bittering agents, flavoring agents, coloring agents and preserving agents in order to provide pharmaceutically elegant and palatable preparations.

Tablets may contain the active ingredient in admixture with non-toxic, pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc, the tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in U.S. Pat. Nos. 4,256,108; 4,166,452; and 4,265,874, all of which are incorporated herein by reference, to form osmotic therapeutic tablets for controlled release.

Formulations for oral use may be hard gelatin capsules, wherein the active ingredient is mixed with an inert solid diluent, for example, calcium carbonate, calcium phosphate or kaolin. Capsules may also be soft gelatin capsules, wherein the active ingredient is mixed with water or miscible solvents such as propylene glycol, PEGs and ethanol, or an oil medium, for example peanut oil, liquid paraffin, or olive oil.

The compositions of the invention may also be in the form of oil-in-water or water-in-oil emulsions. The oily phase maybe a vegetable oil, for example, olive oil or arachis oil, or a mineral oil, for example, liquid paraffin or mixtures of these. Suitable emulsifying agents may be naturally-occurring phosphatides, for example, soy bean, lecithin, and esters or partial esters derived from fatty acids and hexitol anhydrides, for example, sorbitan monoleate, and condensation products of the said partial esters with ethylene oxide, for example, polyoxyethylene sorbitan monooleate. The emulsions may also contain sweetening agents, bittering agents, flavoring agents, and/or preservatives.

In one embodiment of the formulation, the composition of the invention is in the form of a microemulsion. Microemulsions are well suited as the liquid carrier vehicle. Microemulsions are quaternary systems comprising an aqueous phase, an oily phase, a surfactant and a cosurfactant. They are translucent and isotropic liquids. Microemulsions are composed of stable dispersions of microdroplets of the aqueous phase in the oily phase or conversely of microdroplets of the oily phase in the aqueous phase. The size of these microdroplets is typically less than 200 nm (1000 to 100,000 nm for emulsions). The interfacial film is composed of an alternation of surface-active (SA) and co-surface-active (Co-SA) molecules which, by lowering the interfacial tension, allows the microemulsion to be formed spontaneously.

In one embodiment of the oily phase, the oily phase can be formed from mineral or vegetable oils, from unsaturated polyglycosylated glycerides or from triglycerides, or alternatively from mixtures of such compounds. In one embodiment of the oily phase, the oily phase comprises of triglycerides. In another embodiment of the oily phase, the triglycerides are medium-chain triglycerides, for example $C_8$-$C_{10}$ caprylic/capric triglyceride. Another embodiment of the oily phase will represent a % v/v range selected from the group consisting of about 2 to about 15%; about 7 to about 10%; and about 8 to about 9% v/v of the microemulsion. The aqueous phase includes, for example water or glycol derivatives, such as propylene glycol, glycol ethers, polyethylene glycols or glycerol. In one embodiment of the glycol derivatives, the glycol is selected from the group consisting of propylene glycol, diethylene glycol monoethyl ether, dipropylene glycol monoethyl ether and mixtures thereof. Generally, the aqueous phase will represent a proportion from about 1 to about 4% v/v in the microemulsion.

Surfactants for the microemulsion include diethylene glycol monoethyl ether, dipropyelene glycol monomethyl ether, polyglycolyzed $C_8$-$C_{10}$ glycerides or polyglyceryl-6 dioleate. In addition to these surfactants, the cosurfactants include short-chain alcohols, such as ethanol and propanol.

Some compounds are common to the three components discussed above, i.e., aqueous phase, surfactant and cosurfactant. However, it is well within the skill level of the practitioner to use different compounds for each component of the same formulation. In one embodiment for the amount of surfactant/cosurfactant, the cosurfactant to surfactant ratio will be from about 1/7 to about 1/2. In another embodiment for the amount of cosurfactant, the ratio will be from about 25 to about 75% v/v of surfactant and from about 10 to about 55% v/v of cosurfactant in the microemulsion.

Oily suspensions may be formulated by suspending the active ingredient in a vegetable oil, for example, atachis oil, olive oil, sesame oil or coconut oil, or in mineral oil such as liquid paraffin. The oily suspensions may contain a thickening agent, for example, beeswax, hard paraffin or cetyl alcohol. Sweetening agents such as sucrose, saccharin or aspartame, bittering agents, and flavoring agents may be added to provide a palatable oral preparation. These compositions may be preserved by the addition of an anti-oxidant such as ascorbic acid, or other known preservatives.

Aqueous suspensions may contain the active material in admixture with excipients suitable for the manufacture of aqueous suspensions. Such excipients are suspending agents, for example, sodium carboxymethylcellulose, methylcellulose, hydroxy-propylmethylcellulose, sodium alginate, polyinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide, with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents and/or bittering agents, such as those set forth above.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, bittering, flavoring and coloring agents, may also be present. Syrups and elixirs may be formulated with sweetening agents, for example, glycerol, propylene glycol, sorbitol or sucrose. Such formulations may also contain a demulcent, a preservative, flavoring agent(s) and/or coloring agent(s).

In another embodiment of the invention, the composition can be in paste form. Examples of embodiments in a paste form include but are not limited to those described in U.S. Pat. Nos. 6,787,342 and 7,001,889, both of which are incorporated herein by reference. In addition to the active agent of the invention, the paste can also contain fumed silica; a viscosity modifier; a carrier; optionally, an absorbent; and optionally, a colorant, stabilizer, surfactant, or preservative.

The process for preparing a paste formulation typically comprises the steps of:
(a) dissolving or dispersing the active agent into the carrier by mixing;
(b) adding the fumed silica to the carrier containing the dissolved active agent compound and mixing until the silica is dispersed in the carrier;
(c) allowing the intermediate formed in (b) to settle for a time sufficient in order to allow the air entrapped during step (b) to escape; and
(d) adding the viscosity modifier to the intermediate with mixing to produce a uniform paste.

The above steps are illustrative, but not limiting. For example, step (a) can be the last step.

In one embodiment of the formulation, the formulation is a paste containing the active agent compound, fumed silica, a viscosity modifier, an absorbent, a colorant; and a hydrophilic carrier which is a triacetin, a monoglyceride, a diglyceride, or a triglyceride.

The paste may also include a viscosity modifier including, but not limited to, polyethylene glycols (PEG) such as PEG 200, PEG 300, PEG 400, PEG 600; monoethanolamine, triethanolamine, glycerol, propylene glycol, polyoxyethylene (20) sorbitan mono-oleate (polysorbate 80 or Tween 80), and polyoxamers (e.g., Pluronic L 81); an absorbent selected from the group consisting of magnesium carbonate, calcium carbonate, starch, and cellulose and its derivatives.

Colorants may be added to the inventive formulations. Colorants contemplated by the present invention are those commonly known in the art. Specific colorants include, for example, dyes, FD&C Blue #1 Aluminum Lake, caramel, colorant based upon iron oxide or a mixture of any of the foregoing. Especially preferred are organic dyes and titanium dioxide. Preferred ranges include from about 0.5% to about 25%.

In some embodiments, the compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-aceptable diluent or solvent, for example, as a solution in 1,3-butane diol. Among the acceptable vehicles and solvents that may be employed are water, Ringer's solution and isotonic sodium chloride solution. Cosolvents such as ethanol, propylene glycol or polyethylene glycols may also be used. Preservatives, such as phenol or benzyl alcohol, may be used.

In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Topical, dermal and subdermal formulations can include emulsions, creams, ointments, gels, pastes, powders, shampoos, pour-on formulations, ready-to-use formulations, spot-on solutions and suspensions. Topical application of an inventive compound or of a composition including at least one inventive compound among the active agent(s) therein, in the form of a spot-on composition, can allow for the inventive compound to be distributed through the glands (e.g. sebaceous glands) of the animal and/or allow active agent(s) to achieve a systemic effect (plasma concentration) or throughout the haircoat. When the compound is distributed throughout glands, the glands can act as a reservoir, whereby there can be a long-lasting, e.g. 1-2 months effect. Spot-on formulations are typically applied in a localized region which refers to an area other than the entire animal. In one embodiment of a localized region, the location is between the shoulders. In another embodiment, the localized region is a stripe, e.g. a stripe from head to tail of the animal.

Pour-on formulations are described, for example, in U.S. Pat. No. 6,010,710, which is incorporated herein by reference. Some pour-on formulations known in the art are advantageously oily, and generally comprise a diluent or vehicle and also a solvent (e.g. an organic solvent) for the active ingredient if the latter is not soluble in the diluent. Other pour-on formulations known in the art are not oily and comprise an alcohol base.

Organic solvents that can be used in the invention include those described above, and include but are not limited to: acetyltributyl citrate, oleic acid, fatty acid esters such as the dimethyl ester, diisobutyl adipate, diisopropyl adipate (also known as CERAPHYL 230), ketones including acetone, methylisobutyl ketone (MIK) and methyl ethyl ketone and the like, acetonitrile, benzyl alcohol, methanol, ethyl alcohol, isopropanol, butanol, aromatic ethers such as anisole, butyl diglycol, amides including dimethylacetamide and dimethylformamide, dimethyl sulfoxide, propylene glycol monomethyl ether, propylene glycol monoethyl ether, dipropylene glycol n-butyl ether, ethylene glycol monoethyl ether, ethylene glycol monomethyl ether, monomethylacetamide, dipropylene glycol monomethyl ether, liquid polyoxyethylene glycols, propylene glycol, 2-pyrrolidone including N-methylpyrrolidone, diethylene glycol monoethyl ether, ethylene glycol, triacetin, $C_1$-$C_{10}$ esters of carboxylic acids such as butyl or octyl acetate, benzyl acetate, aryl esters including benzyl benzoate, ethyl benzoate and the like, propylene carbonate, butylene carbonate, and diethyl phthalate, or a mixture of at least two of these solvents.

As vehicle or diluent, mention may be made of plant oils such as, but not limited to soybean oil, groundnut oil, castor oil, corn oil, cotton oil, olive oil, grape seed oil, sunflower oil, etc.; mineral oils such as, but not limited to, petrolatum, paraffin, silicone, etc.; aliphatic or cyclic hydrocarbons or alternatively, for example, medium-chain (such as C8 to C12) triglycerides.

In another embodiment of the invention, an emollient and/or spreading and/or film-forming agent will be added. One embodiment of the emollient and/or spreading and/or film-forming agents are those agents selected from the group consisting of:
(a) polyvinylpyrrolidone, polyvinyl alcohols, copolymers of vinyl acetate and vinylpyrrolidone, polyethylene glycols, benzyl alcohol, mannitol, glycerol, sorbitol, polyoxyethylenated sorbitan esters; lecithin, sodium carboxymethylcellulose, silicone oils, polydiorganosiloxane oils (such as polydimethylsiloxane (PDMS) oils), for example those containing silanol functionalities, or a 45V2 oil,
(b) anionic surfactants such as alkaline stearates, sodium, potassium or ammonium stearates; calcium stearate, triethanolamine stearate; sodium abietate; alkyl sulphates (e.g. sodium lauryl sulphate and sodium cetyl sulphate); sodium dodecylbenzenesulphonate, sodium dioctylsulphosuccinate; fatty acids (e.g. those derived from coconut oil),
(c) cationic surfactants such as water-soluble quaternary ammonium salts of formula $N^+R'R''R'''R''''Y^-$, in which the R radicals are optionally hydroxylated hydrocarbon radicals and $Y^-$ is an anion of a strong acid such as the halide, sulphate and sulphonate anions; cetyltrimethylammonium bromide is among the cationic surfactants which can be used,
(d) amine salts of formula $N^+R'R''R'''$ in which the R radicals are optionally hydroxylated hydrocarbon radicals; octadecylamine hydrochloride is among the cationic surfactants which can be used,
(e) nonionic surfactants such as sorbitan esters, which are optionally polyoxyethylenated (e.g. polysorbate 80), polyoxyethylenated alkyl ethers; polyoxypropylated fatty alcohols such as polyoxypropylene-styrol ether; polyethylene glycol stearate, polyoxyethylenated derivatives of castor oil, polyglycerol esters, polyoxyethylenated fatty alcohols, polyoxyethylenated fatty acids, copolymers of ethylene oxide and propylene oxide,
(f) amphoteric surfactants such as the substituted lauryl compounds of betaine, and
(g) a mixture of at least two of these agents.

The solvent will be used in proportion with the concentration of the active agent compound and its solubility in this solvent. Typically, it will be sought to have the lowest possible volume. The vehicle makes up the difference to 100%.

In one embodiment of the amount of emollient, the emollient may be used in a proportion of from about 0.1 to about 10%, and about 0.25 to about 5%, by volume.

In another embodiment of the invention, the composition can be in ready-to-use solution form as is described, for example, in U.S. Pat. No. 6,395,765, which is incorporated herein by reference. In addition to the active agent compound, the ready-to-use solution can contain a crystallization inhibitor, an organic solvent and an organic co-solvent.

In some embodiments, the crystallization inhibitor can be present in a proportion of about 1 to about 30% (w/v). Typically, the crystallization inhibitor may be present in a proportion of about 1% to about 20% (w/v) or about 5% to about 15% (w/v). Acceptable inhibitors are those whose addition to the formulation inhibits the formation of crystals when the formulation is applied. In some embodiments, formulations may include compounds that function as crystallization inhibitors other than those listed herein. In these embodiments, the suitability of a crystallization inhibitor may be determined by testing if it will sufficiently inhibit the formation of crystals so that a sample containing 10% (w/v) of the active agent in a solvent as described above with 10% (w/v) of the crystallization inhibitor will result in less 20, preferably less than 10 crystals when placed on a glass slide at 20° C. for 24 hours.

Crystallization inhibitors which are useful for the invention include but are not limited to:
(a) polyvinylpyrrolidone, polyvinyl alcohols, copolymers of vinyl acetate and of vinylpyrrolidone, 2-pyrrolidone including N-methylpyrrolidone, dimethylsufoxide, polyethylene glycols, benzyl alcohol, mannitol, glycerol, sorbitol or polyoxyethylenated esters of sorbitan; lecithin or sodium carboxymethylcellulose; or acrylic derivatives, such as methacrylates and polymers derived from acrylic monomers, a solvent as described herein that inhibits the crystallization of the active agent, and others;
(b) anionic surfactants, such as alkaline stearates (e.g. sodium, potassium or ammonium stearate); calcium stearate or triethanolamine stearate; sodium abietate; alkyl sulphates, which include but are not limited to sodium lauryl sulphate and sodium cetyl sulphate; sodium dodecylbenzenesulphonate or sodium dioctyl sulphosuccinate; or fatty acids (e.g. coconut oil);
(c) cationic surfactants, such as water-soluble quaternary ammonium salts of formula $N^+R'R''R'''R''''Y^-$, in which the R radicals are identical or different optionally hydroxylated hydrocarbon radicals and $Y^-$ is an anion of a strong acid, such as halide, sulphate and sulphonate anions; cetyltrimethylammonium bromide is one of the cationic surfactants which can be used;
(d) amine salts of formula $N^+R'R''R'''$, in which the R radicals are identical or different optionally hydroxylated hydrocarbon radicals; octadecylamine hydrochloride is one of the cationic surfactants which can be used;
(e) non-ionic surfactants, such as optionally polyoxyethylenated esters of sorbitan, e.g. Polysorbate 80, or polyoxyethylenated alkyl ethers; polyethylene glycol stearate, polyoxyethylenated derivatives of castor oil, polyglycerol esters, polyoxyethylenated fatty alcohols, polyoxyethylenated fatty acids or copolymers of ethylene oxide and of propylene oxide;
(f) amphoteric surfactants, such as substituted lauryl compounds of betaine; or
(g) a mixture of at least two of the compounds listed in (a)-(f) above.

In one embodiment of the crystallization inhibitor, a crystallization inhibitor pair will be used. Such pairs include, for example, the combination of a film-forming agent of polymeric type and of a surface-active agent. These agents can be selected from the compounds mentioned above as crystallization inhibitor.

In one embodiment of the film-forming agent, the agents are of the polymeric type which include but are not limited to the various grades of polyvinylpyrrolidone, polyvinyl alcohols, and copolymers of vinyl acetate and of vinylpyrrolidone.

In one embodiment of the surface-active agents, the agents include but are not limited to those made of non-ionic surfactants. In another embodiment of the surface active agents, the agent is a polyoxyethylenated ester of sorbitan. In yet another embodiment of the surface-active agent, the agents include the various grades of polysorbate, for example Polysorbate 80.

In another embodiment of the invention, the film-forming agent and the surface-active agent can be incorporated in similar or identical amounts within the limit of the total amounts of crystallization inhibitor mentioned above.

The pair thus constituted secures, in a noteworthy way, the objectives of absence of crystallization on the coat and of maintenance of the cosmetic appearance of the skin or fur, that is to say without a tendency towards sticking or towards a sticky appearance, despite the high concentration of active material.

The formulation adjuvants are well known to the practitioner in this art and may be obtained commercially or through known techniques. These concentrated compositions are generally prepared by simple mixing of the constituents as defined above. Advantageously, the starting point is to mix the active material in the main solvent and then the other ingredients or adjuvants are added.

The volume applied is not restricted as long as the amount of substance administered is shown to be safe and efficacious. Typically, the volume applied depends on the size and weight of the animal as well as the concentration of active, the extent of infestation by parasites and the type of administration. The volume applied is typically of the order of about 0.3 to about 1 ml, or about 0.3 ml to about 5 ml, or about 0.3 ml to about 10 ml. In other embodiments, the volume may be about 4 ml to about 7 ml. For larger animals, the volume may be higher including, but not limited to, up to 10 ml, up to 20 ml or up to 30 ml, or higher. In one embodiment of the volume, the volume is on the order of about 0.5 ml to about 1 ml for cats, and on the order of about 0.3 to about 3 ml or 4 ml for dogs, depending on the weight of the animal.

In another embodiment of the invention, application of a spot-on formulation according to the present invention can also provide long-lasting and broad-spectrum efficacy when the solution is applied to the mammal or bird. The spot-on formulations provide for topical administration of a concentrated solution, suspension, microemulsion or emulsion for intermittent application to a spot on the animal, generally between the two shoulders (solution of spot-on type).

Liquid carriers for spot-on formulations include the organic solvents, and mixtures thereof, described above, among other solvents known in the art. The liquid carrier vehicle can optionally contain a crystallization inhibitor such as the crystallization inhibitors described above, or mixtures thereof.

Spot-on formulations may be prepared by dissolving the active ingredients into the pharmaceutically or veterinary acceptable vehicle. Alternatively, the spot-on formulation can be prepared by encapsulation of the active ingredient to leave a residue of the therapeutic agent on the surface of the animal. These formulations will vary with regard to the weight of the therapeutic agent in the combination depending on the species of host animal to be treated, the severity and type of infection and the body weight of the host.

Additionally, the inventive formulations may contain other inert ingredients such as antioxidants, preservatives, or pH stabilizers. These compounds are well known in the formulation art. Antioxidant such as an alpha tocopherol, ascorbic acid, ascrobyl palmitate, fumeric acid, malic acid, sodium ascorbate, sodium metabisulfate, sodium thiosulfate, n-propyl gallate, BHA (butylated hydroxy anisole), BHT (butylated hydroxy toluene) monothioglycerol and the like, or a combination thereof, may be added to the formulations. The antioxidants are generally added to the formulation in amounts of from about 0.01 to about 2.0%, based upon total weight of the formulation, with about 0.05 to about 1.0% being especially preferred. Preservatives, such as the parabens (methylparaben and/or propylparaben), are suitably used in the formulation in amounts ranging from about 0.01 to about 2.0%, with about 0.05 to about 1.0% being especially preferred. Other preservatives include benzalkonium chloride, benzethonium chloride, benzoic acid, benzyl alcohol, bronopol, butylparaben, cetrimide, chlorhexidine, chlorobutanol, chlorocresol, cresol, ethylparaben, imidurea, methylparaben, phenol, phenoxyethanol, phenylethyl alcohol, phenylmercuric acetate, phenylmercuric borate, phenylmercuric nitrate, potassium sorbate, sodium benzoate, sodium propionate, sorbic acid, thimerosal, and the like. Preferred ranges for these compounds include from about 0.01 to about 5%.

Compounds which stabilize the pH of the formulation are also contemplated. Again, such compounds are well known to a practitioner in the art as well as how to use these compounds. Buffering systems include, for example, systems selected from the group consisting of acetic acid/acetate, malic acid/malate, citric acid/citrate, tataric acid/tartrate, lactic acid/lactate, phosphoric acid/phosphate, glycine/glycimate, tris, glutamic acid/glutamates and sodium carbonate. Preferred ranges for pH include from about 4 to about 6.5.

In one embodiment of the invention, the active agent is present in the formulation at a concentration of about 0.05 to about 40% (w/v). In another embodiment of the invention, the active agent is present in the formulation as a concentration from about 1 to about 30% or about 1 to about 20% (w/v). In yet another embodiment of the invention, the active agent is present in the formulation as a concentration from about 5 to about 15% (w/v). In still another embodiment of the invention, the active agent is present in the formulation as a concentration about 10% (w/v), about 20% (w/v) or about 30% (w/v).

In another embodiment of the invention, the active agent is present in the formulation at a concentration of about 0.05 to 10% weight/volume. In another embodiment of the invention, the active agent is present in the formulation as a concentration from about 0.1 to 2% weight/volume. In yet another embodiment of the invention, the active agent is present in the formulation as a concentration from about 0.25 to about 1.5% weight/volume. In still another embodiment of the invention, the active agent is present in the formulation as a concentration about 1% weight/volume.

The composition containing the active agent of the invention may be administered continuously, for treatment or prophylaxis, by known methods. Generally, a dose of from about 0.001 to about 100 mg per kg of body weight given as a single dose or in divided doses for a period of from 1 to 5 days will be satisfactory but, of course, there can be instances where higher or lower dosage ranges are indicated, and such are within the scope of this invention. It is well within the routine skill of the practitioner to determine a particular dosing regimen for a specific host and parasite.

In one embodiment, the treatment is carried out so as to administer to the animal, on a single occasion, a dose containing between about 0.001 and about 100 mg/kg of the active agent.

In another embodiment, the treatment is via a direct topical administration such as a paste, pour-on, ready-to-use, spot-on, etc. type formulation. Higher amounts may be provided for very prolonged release in or on the body of the animal. In another embodiment, the amount of the active ingredient for birds and animals which are small in size is greater than about 0.001 mg/kg. In other embodiments, the amount of active ingredient is 0.001 mg/kg to about 1 mg/kg, or about 0.001 mg/kg to about 0.1 mg/kg of weight of the animal. In still other embodiments, the dose of active ingredient is about 0.001 mg/kg to about 0.01 mg/kg of weight of the animal. In other embodiments for larger animals, the dose of the active compounds may be from about 1 mg/kg to about 50 mg/kg, about 1 mg/kg to about 30 mg/kg or about 1 mg/kg to about 20 mg/kg of weight of the animal.

In one embodiment, a direct pour-on skin formulation according to the present invention can provide long-lasting and broad-spectrum efficacy when the solution is applied to the animal's back, e.g. along the line of the back at one or more points. According to a first embodiment for administering direct pour-on formulations, the process comprises applying the solution to the animals, the application being repeated every month or every two months. According to a second embodiment for administering direct pour-on formulation, the process comprises applying the solution to livestock animals before they arrive in the Feed Lot, it being possible for this application to be the final one before the animals are slaughtered. Obviously, the process may also consist in combining these two embodiments, namely the first followed by the second. The solutions according to the invention may be applied using any means known per se, e.g. using an applicator gun or a metering flask.

In another embodiment, the compounds of the invention are administered in spot-on formulations. The application of spot-on formulations according to the present invention can also obtain long-lasting and broad-spectrum efficacy when the solution is applied to the mammal or bird. Administration of the spot-on formulation may be intermittent in time and may be administered daily, weekly, biweekly, monthly, bimonthly, quarterly, every six months or even for longer durations of time. The time period between treatments depends upon factors such as the parasite(s) being treated, the degree of infestation, the type of mammal or bird and the environment where it resides. It is well within the skill level of the practitioner to determine a specific administration period for a particular situation. This invention contemplates a method for permanently combating a parasite in an environment in which the animal is subjected to strong parasitic pressure where the administration is at a frequency far below a daily administration in this case. For example, it is preferable for the treatment according to the invention to be carried out monthly on dogs and on cats.

While not wishing to be bound by theory, it is believed that these formulations work by dissolution of the dose in the natural oils of the host's skin, fur or feathers. From there, the active agent(s) distribute around the host's body through the sebaceous glands of the skin. The therapeutic agent also remains in the sebaceous glands. Thus, the glands provide a natural reservoir for the active agent that allows for the agent to be drained back out to the follicles to reapply itself to the skin and hair. This, in turn, provides for longer time periods between applications as well as eliminating the need to re-administer the dose after the host becomes wet because of rain, bathes, etc. The inventive formulation has the further advantage of not being directly deposited on the skin or fur, where self-grooming animals could orally ingest the therapeutic agent, thereby becoming sick or possibly interacting with other therapeutic agent being orally administered.

In one embodiment of the location of administration, a single formulation containing the active agent in a substantially liquid carrier and in a form which makes possible a single application, or an application repeated a small number of times, will be administered to the animal over a localized region of the animal, e.g. between the two shoulders. In one embodiment of the invention, the localized region has a surface area of about 10 cm$^2$ or larger. In another embodiment of the invention, the localized region has a surface area of between about 5 and about 10 cm$^2$.

Other routes of administration include paste formulation, oral drench formulation, chewable formulation, transdermal or transmucosal patch or liquid, gel or paste, solution for inhalation and injectable formulation.

In one aspect of the invention, the compounds and formulations of the invention may be used for the treatment or prevention of parasitic infestations or infections in crops, plants, plant propagation material or material derived from wood. The compounds of the invention or their salts can be employed as such or in the form of their preparations (formulations) as combinations with other pesticidally active substances, such as, for example, insecticides, attractants, sterilants, acaricides, nematicides, herbicides, fungicides, and with safeners, fertilizers and/or growth regulators, for example as a premix/readymix.

Classifications of fungicides are well-known in the art and include classifications by FRAC (Fungicide Resistance Action Committee). Fungicides which may optionally be admixed include, but are not limited to, methyl benzimidazole carbamates, such as benzimidazoles and thiophanates; dicarboximides; demethylation inhibitors, such as imidazoles, piperazines, pyridines, pyrimidines, and triazoles; phenylamides, such as acylalanines, oxazolidinones, and butyrolactones; amines, such as morpholines, piperidines, and spiroketalamines; phosphorothiolates; dithiolanes; carboxamides; hydroxy-(2-amino-)pyrimidines; anilino-pyrimidines; N-phenyl carbamates; quinone outside inhibitors; phenylpyrroles; quinolines; aromatic hydrocarbons; heteroaromatics; melanin biosynthesis inhibitors-reductase; melanin biosynthesis inhibitors-dehydratase; hydroxyanilides (SBI class III), such as fenhexamid; SBI class IV, such as thiocarbamates and allylamines; polyoxins; phenylureas; quinone inside inhibitors; benzamides; enopyranuronic acid antibiotic; hexopyranosyl antibiotic; glucopyranosyl antibiotic; glucopyranosyl antibiotic; cyanoacetamideoximes; carbamates; uncoupler of oxidative phosphorylation; organo tin compounds; carboxylic acids; heteroaromatics; phosphonates; phthalamic acids; benzotriazines; benzenesulfonamides; pyridazinones; carboxylic acid amides; tetracycline antibiotic; thiocarbamate; benzo-thiadiazole BTH; benzisothiazole; thiadiazolecarboxamide; thiazolecarboxamides; benzamidoxime; quinazolinone; benzophenone; acylpicolide; inorganic compounds, such as copper salts and sulphur; dithiocarbamates and relatives; phthalimides; chloronitriles; sulphamides; guanidines; triazines; quinones. Other fungicides that may optionally be admixed may also be from the classes of compounds described in U.S. Pat. Nos. 7,001,903 and 7,420,062, both of which are incorporated herein by reference.

Herbicides that are known from the literature and classified by HRAC (Herbicide Resistance Action Committee) and may be combined with the compounds of the invention are, for example: aryloxyphenoxy-propionate; cyclohexanedione; phenylpyrazoline; sulfonylurea; imidazolinone, such as imazapic and imazethapyr; triazolopyrimidine; pyrimidinyl (thio)benzoate; sulfonylaminocarbonyl-triazolinone; triazine, such as atrazine; triazinone; triazolinone; uracil; pyridazinone; phenyl-carbamate; urea; amide; nitrile; benzothiadiazinone; phenyl-pyridazine; bipyridylium, such as paraquat; diphenylether; phenylpyrazole; N-phenylphthalimide; thiadiazole; thiadiazole; triazolinone; oxazolidinedione; pyrimidindione; pyridazinone; pyridinecarboxamide; triketone; isoxazole; pyrazole; triazole; isoxazolidinone; urea, such as linuron; diphenylether; glycine, such as glyphosate; phosphinic acid, such as glufosinate-ammonium; carbamate; dinitroaniline, such as pendimethalin; phosphoroamidate; pyridine; benzamide; benzoic acid; chloroacetamide; metolachlor; acetamide; oxyacetamide; tetrazolinone; nitrile; benzamide; triazolocarboxamide; quinoline carboxylic acid; dinitrophenol; thiocarbamate; phosphorodithioate; benzofuran; chloro-carbonic-acid; phenoxy-carboxylic-acid, such as 2,4-D; benzoic acid, such as dicamba; pyridine carboxylic acid, such as clopyralid, triclopyr, fluoroxypyr and picloram; quinoline carboxylic acid; phthalamate semicarbazone; qrylaminopropionic acid; qrylaminopropionic acid; organoarsenical. Other herbicides that may optionally be admixed are compounds described in U.S. Pat. Nos. 7,432,226, 7,012, 041, and 7,365,082, all of which are incorporated herein by reference.

Appropriate herbicide safeners include but are not limited to benoxacor, cloquintocet, cyometrinil, cyprosulfamide, dichlormid, dicyclonon, dietholate, fenchlorazole, fenclorim, flurazole, fluxofenim, furilazole, isoxadifen, mefenpyr, mephenate, naphthalic anyhydride and oxabetrinil.

Bactericides include, but are not limited to, bronopol, dichlorophen, nitrapyrin, nickel dimethyldithiocarbamate, kasugamycin, octhilinone, furancarboxylic acid, oxytetracycline, probenazole, streptomycin, tecloftalam, copper sulphate and other copper preparations.

Insecticides/acaricides/nematicides include those compounds mentioned in U.S. Pat. Nos. 7,420,062 and 7,001,903, U.S. Patent publication 2008/0234331, all of which are incorporated herein by reference, the literature known to the person skilled in the art, and the compounds classified by IRAC (Insecticide Resistance Action Committee). Examples of insecticides/acaricides/nematicides include, but are limited to, carbamates; triazemate; organophosphates; cyclodiene organo chlorines; phenylpyrazoles; DDT; methoxychlor; pyrethroids; pyrethrins; neonicotinoids; nicotine; bensultap; cartap hydrochloride; nereistoxin analogues; spinosyns; avermectins and milbemycins; juvenile hormone analogues; fenoxycarb; fenoxycarb; alkyl halides; chloropicrin; sulfuryl fluoride; cryolite; pymetrozine; flonicamid; clofentezine; hexythiazox; etoxazole; *Bacillus sphaericus*; diafenthiuron; organotin miticides; prop argite; tetradifon; chlorfenapyr; DNOC; benzoylureas; buprofezin; cyromazine; diacylhydrazines; azadirachtin; amitraz; hydramethylnon; acequinocyl; fluacrypyrim; METI acaricides; rotenone; indoxacarb; metaflumizone; tetronic acid derivatives; aluminium phosphide; cyanide; phosphine; bifenazate; fluoroacetate; P450-dependent monooxygenase inhibitors; esterase inhibitors; diamides; benzoximate; chinomethionat; dicofol; pyridalyl; borax; tartar emetic; fumigants, such as methyl bromide; ditera; clandosan; sincocin.

The compounds of the invention can be formulated in various ways, depending on the prevailing biological and/or chemico-physical parameters. Examples of possible formulations are: wettable powders (WP), water-soluble powders (SP), water-soluble concentrates, emulsifiable concentrates (EC), emulsions (EW) such as oil-in-water and water-in-oil emulsions, sprayable solutions, suspension concentrates (SC), dispersions on an oil or water basis, solutions which are miscible with oil, capsule suspensions (CS), dusts (DP), seed-dressing products, granules for broadcasting and soil application, granules (GR) in the form of microgranules, spray granules, coated granules and adsorption granules, water-dispersible granules (WG), water-soluble granules (SG), ULV formulations, microcapsules and waxes.

The formulations aforementioned can be prepared in a manner known, for example by mixing the active compounds with at least one solvent or diluent, emulsifier, dispersant and/or binder or fixative, water repellent and optionally one or more of a desiccant, UV stabilizer, a colorant, a pigment and other processing auxiliaries.

These individual formulation types are known in principle and described, for example, in: Winnacker-Küchler, "*Chemische Technologie*" [Chemical Technology], Volume 7, C. Hauser Verlag, Munich, 4th Edition 1986; Wade van Valkenburg, "*Pesticide Formulations*", Marcel Dekker, N.Y., 1973; K. Martens, "Spray Drying Handbook", 3rd Ed. 1979, G. Goodwin Ltd. London.

The necessary formulation auxiliaries such as inert materials, surfactants, solvents and other additives are also known and described, for example, in: Watkins, "*Handbook of Insecticide Dust Diluents and Carriers*", 2nd Ed., Darland Books, Caldwell N.J.; H. v. Olphen, "*Introduction to Clay Colloid Chemistry*", 2nd Ed., J. Wiley & Sons, N.Y.; C. Marsden, "Solvents Guide", 2nd Ed., Interscience, N.Y. 1963; McCutcheon's "*Detergents and Emulsifiers Annual*", MC Publ. Corp., Ridgewood N.J.; Sisley and Wood, "*Encyclopedia of Surface Active Agents*", Chem. Publ. Co. Inc., N.Y. 1964; Schönfeldt, "*Grenzflächenaktive Äthylenoxidaddukte*" [Surface-active ethylene oxide adducts], Wiss. Verlagsgesell., Stuttgart 1976; Winnacker-Küchler, "*Chemische Technologie*" [Chemical Technology], Volume 7, C. Hauser Verlag, Munich, 4th Ed. 1986.

Wettable powders are preparations which are uniformly dispersible in water and which, in addition to the compounds of the invention, also comprise ionic and/or nonionic surfactants (wetters, dispersants), for example, polyoxyethylated alkylphenols, polyoxyethylated fatty alcohols, polyoxyethylated fatty amines, fatty alcohol polyglycol ether sulfates, alkanesulfonates or alkylbenzenesulfonates, sodium lignosulfonate, sodium 2,2'-dinaphthylmethane-6,6'-disulfonate, sodium dibutylnaphthalenesulfonate or else sodium oleoyl-methyltaurinate, in addition to a diluent or inert substance. To prepare the wettable powders, the compounds of the invention are, for example, ground finely in conventional apparatuses such as hammer mills, blower mills and air-jet mills and mixed with the formulation auxiliaries, either concomitantly or thereafter.

Emulsifiable concentrates are prepared, for example, by dissolving the compounds of the invention in an organic solvent, for example, butanol, cyclohexanone, dimethylformamide, xylene or else higher-boiling aromatics or hydrocarbons or mixture of these, with addition of one or more ionic and/or nonionic surfactants (emulsifiers). Emulsifiers which can be used are, for example, calcium salts of alkylarylsulfonic acids such as calcium dodecylbenzenesulfonate, or nonionic emulsifiers such as fatty acid polyglycol esters, alkylaryl polyglycol ethers, fatty alcohol polyglycol ethers, propylene oxide/ethylene oxide condensates, alkyl polyethers, sorbitan esters such as sorbitan fatty acid esters, or polyoxyethylene sorbitan esters such as polyoxyethylene sorbitan fatty acid esters.

Dusts are obtained by grinding the active substance with finely divided solid substances, for example, talc or natural clays, such as kaolin, bentonite or pyrophyllite, or diatomaceous earth.

Suspension concentrates may be water- or oil-based. They can be prepared, for example, by wet grinding by means of commercially available bead mills, if appropriate with addition of surfactants, as they have already been mentioned above, for example, in the case of the other formulation types.

Emulsions, for example oil-in-water emulsions (EW), can be prepared by means of stirrers, colloid mills and/or static mixtures using aqueous organic solvents and, if appropriate, surfactants as they have already been mentioned above for example in the case of the other formulation types.

Granules can be prepared either by spraying the compounds of the invention onto adsorptive, granulated inert material or by applying active substance concentrates onto the surface of carriers such as sand, kaolinites or of granulated inert material, by means of binders, for example polyvinyl alcohol, sodium polyacrylate or alternatively mineral oils. Suitable active substances can also be granulated in the manner which is conventional for the production of fertilizer granules, if desired, in a mixture with fertilizers.

Water-dispersible granules are prepared, as a rule, by the customary processes such as spray-drying, fluidized-bed granulation, disk granulation, mixing in high-speed mixers and extrusion without solid inert material. To prepare disk, fluidized-bed, extruder and spray granules, see, for example, processes in "*Spray-Drying Handbook*" 3rd ed. 1979, G. Goodwin Ltd., London; J. E. Browning, "Agglomeration", Chemical and Engineering 1967, pages 147 et seq.; "*Perry's Chemical Engineer's Handbook*", 5th Ed., McGraw-Hill, New York 1973, p. 8-57.

In general, the agrochemical preparations comprise a range selected from the group consisting of about 0.1 to about 99% by weight and about 0.1 to about 95% by weight, of compounds of the invention.

The concentration of compounds of the invention in wettable powder is, for example, about 10 to about 90% by weight, the remainder to 100% by weight being composed of customary formulation components. In the case of emulsifiable concentrates, the concentration of compounds of the invention can amount to a range selected from the group consisting of about 1% to about 90%, and about 5% to about 80% by weight. Formulations in the form of dusts usually comprise a range selected from the group consisting of about 1% to about 30%, and about 5% to about 20% by weight of compounds of the invention. Sprayable solutions comprise a range selected from the group consisting of about 0.05% to about 80%, and about 2% to about 50% by weight of compounds of the invention. In the case of water-dispersible granules, the content of compounds of the invention depends partly on whether the compounds of the invention are in liquid or solid form and on which granulation auxiliaries, fillers and the like are being used. The water-dispersible granules, for example, comprise a range selected from the group consisting of between about 1 and about 95%, and between about 10% and about 80% by weight.

In addition, the formulations of compounds of the invention mentioned comprise, if appropriate, the adhesives, wetters, dispersants, emulsifiers, penetrants, preservatives, antifreeze agents, solvents, fillers, carriers, colorants, antifoams, evaporation inhibitors, pH regulators and viscosity regulators which are conventional in each case.

The mixtures according to the invention can be applied via the soil either pre-emergently or post-emergently. The mixtures according to the invention can also be applied via the leaf. The mixtures according to the invention can be employed for seed dressing. It is also possible to apply the mixtures according to the invention via an irrigation system, for example, via the water for irrigation.

When used as insecticides, the active compounds according to the invention can furthermore be present in their commercially available formulations and in the use forms, prepared from these formulations, as a mixture with synergists. Synergists are compounds which increase the action of the active compounds, without it being necessary for the synergistic agent added to be active itself.

When used as insecticides, the active compounds according to the invention can furthermore be present in their commercially available formulations and in the use forms, prepared from these formulations, as a mixture with inhibitors which reduce degradation of the active compound after use in the environment of the plant, on the surface of parts of plants or in plant tissues.

The active compound content of the use forms prepared from the commercially available formulations can vary within wide limits. The active compound concentration of the use forms can be from 0.00000001 to 95% by weight of active compound, preferably between 0.00001 and 1% by weight.

All plants and plant parts can be treated in accordance with the invention. Plants are to be understood as meaning, in the present context, all plants and plant populations such as wild plants or crop plants (including naturally occurring crop plants). Crop plants are plants obtained by conventional plant breeding and optimization methods, or by biotechnological and genetic engineering methods, or by combinations of these methods, which include transgenic plants and plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offshoots and seeds.

Treatment according to the invention of the plants and plant parts with the active compounds is carried out directly or by allowing the compounds to act on the surroundings, habitat or storage space by the customary treatment methods, for example, by immersion, spraying, evaporation, fogging, scattering, painting on, injection and, in the case of propagation material, in particular in the case of seeds, also by applying one or more coats.

The active compounds according to the invention are particularly suitable for treating seed. A large part of the damage to crop plants which is caused by pests occurs as early as when the seed is attacked during storage and after the seed is introduced into the soil, during and immediately after germination of the plants. This phase is particularly critical since the roots and shoots of the growing plant are particularly sensitive and even minor damage can lead to the death of the whole plant. Protecting the seed and the germinating plant by the use of suitable active compounds is therefore of particularly great interest.

The control of pests by treating the seeds of plants has been known for a long time and is the subject of continuous improvements. However, the treatment of seed entails a series of problems which cannot always be solved in a satisfactory manner. Thus, it is desirable to develop methods for protecting the seed and the germinating plant which dispense with the additional application of crop protection agents after sowing or after the emergence of the plants. It is furthermore desirable to optimize the amount of active compound employed in such a way as to provide maximum protection for the seed and the germinating plant from attack by pests, but without damaging the plant itself by the active compound employed. In particular, methods for the treatment of seed should also take into consideration the intrinsic insecticidal properties of transgenic plants in order to achieve optimum protection of the seed and the germinating plant with a minimum of crop protection agents being employed.

The present invention therefore also relates to a method for the protection of seed and germinating plants from attack by pests, by treating the seed with an active compound according to the invention. The invention likewise relates to the use of the active compounds according to the invention for the treatment of seed for protecting the seed and the resultant plant from pests. Furthermore, the invention relates to seed which has been treated with an active compound according to the invention so as to afford protection from pests.

One of the advantages of the present invention is that the particular systemic properties of the active compounds according to the invention mean that treatment of the seed with these active compounds not only protects the seed itself, but also the resulting plants after emergence, from pests. In this manner, the immediate treatment of the crop at the time of sowing or shortly thereafter can be dispensed with.

Furthermore, it must be considered as advantageous that the active compounds according to the invention can also be employed in particular in transgenic seed, the plants arising from the seed being capable of expressing a protein directed against pests. By treating such seed with the active compounds according to the invention, certain pests can be controlled merely by the expression of, for example, insecticidal protein, and additionally be protected by the active compounds according to the invention against damage.

The active compounds according to the invention are suitable for protecting seed of any plant variety as already mentioned above which is employed in agriculture, in greenhouse, in forests, or in horticulture. In particular, this takes the form of seed of maize, peanut, canola, oilseed rape, poppy, soybean, cotton, beet (for example sugar beet and fodder beet), rice, sorghum and millet, wheat, barley, oats, rye, sunflower, tobacco, potatoes or vegetables (for example tomatoes, cabbage plants). The active compounds according to the invention are likewise suitable for treating the seed of fruit plants and vegetables as already mentioned above. The treatment of the seed of maize, soybean, cotton, wheat and canola or oilseed rape is of particular importance.

As already mentioned above, the treatment of transgenic seed with an active compound according to the invention is also of particular importance. This takes the form of seed of plants which, as a rule, comprise at least one heterologous gene which governs the expression of a polypeptide with particular insecticidal properties. In this context, the heterologous genes in transgenic seed may be derived from microorganisms such as *Bacillus, Rhizobium, Pseudomonas, Serratia, Trichoderma, Clavibacter, Glomus* or *Gliocladium*. The present invention is suitable for the treatment of transgenic seed which comprises at least one heterologous gene originating from *Bacillus* sp. and whose gene product shows activity against the European corn borer and/or the corn root worm.

In the context of the present invention, the active compound according to the invention is applied to the seed either alone or in a suitable formulation. Preferably, the seed is treated in a state which is stable enough to avoid damage during treatment. In general, the seed may be treated at any point in time between harvest and sowing. The seed used has usually been separated from the plant and is free from cobs, shells, stalks, coats, hairs or the flesh of the fruits.

When treating the seed, care must generally be taken that the amount of the active compound according to the invention applied to the seed and/or the amount of further additives is chosen in such a way that the germination of the seed is not adversely affected, or that the resulting plant is not damaged. This must be borne in mind in particular in the case of active compounds which may have phytotoxic effects at certain application rates.

As already mentioned above, it is possible to treat all plants and their parts according to the invention. In one embodiment, wild plant species and plant cultivars, or those obtained by conventional biological breeding methods, such as crossing or protoplast fusion, and parts thereof, are treated. In another embodiment, transgenic plants and plant cultivars obtained by genetic engineering methods, if appropriate in combination with conventional methods, and parts thereof are treated. In yet another embodiment, plants of the plant cultivars which are in each case commercially available or in use are treated according to the invention. Plant cultivars are to be understood as meaning plants having novel properties ("traits") which have been obtained by conventional breeding, by mutagenesis or by recombinant DNA techniques. These can be cultivars, bio- or genotypes.

Depending on the plant species or plant cultivars, their location and growth conditions (soils, climate, vegetation period, diet), the treatment according to the invention may also result in synergistic effects. Thus, it is possible, for example, to achieve the effects of reduced application rates, widening of the activity spectrum, an increase in the activity of the active compounds and compositions which can be used according to the invention, better plant growth, increased tolerance to high or low temperatures, increased tolerance to drought or high soil salt content, increased flowering performance, easier harvesting, accelerated maturation, higher harvest yields, higher quality and/or a higher nutritional value of the harvested products, better storage stability and/or processability of the harvested products.

The transgenic plants or plant cultivars (obtained by genetic engineering) which are preferably to be treated according to the invention include all plants which, by virtue of the genetic modification, received genetic material that imparted particularly advantageous, useful traits to these plants. Examples of such traits are better plant growth, increased tolerance to high or low temperatures, increased tolerance to drought or high soil salt content, increased flowering performance, accelerated maturation, higher harvest yields, higher quality and/or a higher nutritional value of the harvested products, better storage stability and/or processability of harvested products. Further and particularly emphasized examples of such traits are a better defense of the plants against animal and microbial pests, such as insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soybean, potatoes, sugar beet, tomatoes, peas and other vegetable varieties, cotton, tobacco, oilseed rape and also fruit plants (with the fruits apples, pears, citrus fruits and grapes), and particular emphasis is given to maize, soybean, potatoes, cotton, tobacco and oilseed rape. Traits include, but are not limited to, increased defense of the plants against insects, arachnids, nematodes and slugs and snails by virtue of toxins formed in the plants, and those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof) (referred to hereinbelow as "Bt plants"). Traits also include, but are not limited to, increased defense of the plants against fungi, bacteria and viruses by systemic acquired resistance (SAR), systemin, phytoalexins, elicitors and resistance genes and correspondingly expressed proteins and toxins. Traits further include, but are not limited to, increased tolerance of the plants to certain herbicidally active compounds, for example, imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soybean varieties, and potato varieties which are sold under the trade names YIELD GARD® (such as maize, cotton, soybean), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soybean varieties which are sold under the trade names Roundup Ready® (tolerance to glyphosate, for example maize, cotton, soybean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) include the varieties sold under the name Clearfield® (for example maize).

In the field of household insecticides, the active compounds according to the invention are used alone or in combination with other suitable active compounds, such as phosphoric esters, carbamates, pyrethroids, neonicotinoids, growth regulators or active compounds from other known classes of insecticides.

It has furthermore been found that the active compounds according to the invention also have a strong insecticidal action against insects which destroy industrial materials.

The following insects may be mentioned as examples, but without any limitation: beetles, hymenopterons, termites, and bristletails.

Industrial materials in the present content are to be understood as meaning non-living materials, such as, plastics, adhesives, sizes, papers and cardboards, leather, wood and processed wood products and coating compositions.

The active compounds according to the invention are used in aerosols, pressure-free spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free, or passive, evaporation systems, moth papers, moth bags and moth gels, as granules or dusts, in baits for spreading or in bait stations.

Additional pharmaceutical active agents may be used in the compositions of the invention. Active agents include pesticidally or veterinarily active ingredients, which include, but are not limited to, acaricides, anthelmintics, anti-parasitics and insecticides, may also be added to the compositions of the invention. Anti-parasitic agents can include both ectoparasiticisal and endoparasiticidal agents.

Other active agents that are well-known in the art may be used in the compositions of the invention (see e.g. *Plumb' Veterinary Drug Handbook*, $5^{th}$ Edition, ed. Donald C. Plumb, Blackwell Publishing, (2005) or *The Merck Veterinary Manual*, $9^{th}$ Edition, (January 2005)) including, but are not limited to, acarbose, acepromazine maleate, acetaminophen, acetazolamide, acetazolamide sodium, acetic acid, acetohydroxamic acid, acetylcysteine, acitretin, acyclovir, albendazole, albuterol, alfentanil, allopurinol, alprazolam, altrenogest, amantadine, amikacin, aminocaproic acid, aminopentamide hydrogen sulfate, aminophylline/theophylline, amiodarone, amitraz, amitriptyline, amlodipine besylate, ammonium chloride, ammonium molybdenate, amoxicillin, amoxicillin, clavulanate potassium, amphotericin B desoxycholate, amphotericin B lipid-based, ampicillin, amprolium, antacids (oral), antivenin, apomorphione, apramycin sulfate, ascorbic acid, asparaginase, aspiring, atenolol, atipamezole, atracurium besylate, atropine sulfate, aurnofin, aurothioglucose, azaperone, azathioprine, azithromycin, baclofen, barbituates, benazepril, betamethasone, bethanechol chloride, bisacodyl, bismuth subsalicylate, bleomycin, boldenone undecylenate, bromides, bromocriptine mesylate, budenoside, buprenorphine, buspirone, busulfan, butorphanol tartrate, cabergoline, calcitonin salmon, calcitrol, calcium salts, captopril, carbenicillin indanyl sodium, carbimazole, carboplatin, carnitine, carprofen, carvedilol, cefadroxil, cefazolin sodium, cefixime, cefoperazone sodium, cefotaxime sodium, cefotetan disodium, cefoxitin sodium, cefpodoxime proxetil, ceftazidime, ceftiofur sodium, ceftiofur, ceftriaxone sodium, cephalexin, cephalosporins, cephapirin, charcoal (activated), chlorambucil, chloramphenicol, chlordiazepoxide, chlordiazepoxide+/−clidinium bromide, chlorothiazide, chlorpheniramine maleate, chlorpromazine, chlorpropamide, chlortetracycline, chorionic gonadotropin (HCG), chromium, cimetidine, ciprofloxacin, cisapride, cisplatin, citrate salts, clarithromycin, clemastine fumarate, clenbuterol, clindamycin, clofazimine, clomipramine, claonazepam, clonidine, cloprostenol sodium, clorazepate dipotassium, clorsulon, cloxacillin, codeine phosphate, colchicine, corticotropin (ACTH), cosyntropin, cyclophosphamide, cyclosporine, cyproheptadine, cytarabine, dacarbazine, dactinomycin/actinomycin D, dalteparin sodium, danazol, dantrolene sodium, dapsone, decoquinate, deferoxamine mesylate, deracoxib, deslorelin acetate, desmopressin acetate, desoxycorticosterone pivalate, detomidine, dexamethasone, dexpanthenol, dexraazoxane, dextran, diazepam, diazoxide (oral), dichlorphenamide, dichlorvos, diclofenac sodium, dicloxacillin, diethylcarbamazine citrate, diethylstilbestrol (DES), difloxacin, digoxin, dihydrotachysterol (DHT), diltiazem, dimenhydrinate, dimercaprol/BAL, dimethyl sulfoxide, dinoprost tromethamine, diphenylhydramine, disopyramide phosphate, dobutamine, docusate/DSS, dolasetron mesylate, domperidone, dopamine, doramectin, doxapram, doxepin, doxorubicin, doxycycline, edetate calcium disodium.calcium EDTA, edrophonium chloride, enalapril/enalaprilat, enoxaparin sodium, enrofloxacin, ephedrine sulfate, epinephrine, epoetin/erythropoietin, eprinomectin, epsiprantel, erythromycin, esmolol, estradiol cypionate, ethacrynic acid/ethacrynate sodium, ethanol (alcohol), etidronate sodium, etodolac, etomidate, euthanasia agents w/pentobarbital, famotidine, fatty acids (essential/omega), felbamate, fenbendazole, fentanyl, ferrous sulfate, filgrastim, finasteride, fipronil, florfenicol, fluconazole, flucytosine, fludrocortisone acetate, flumazenil, flumethasone, flunixin meglumine, fluorouracil (5-FU), fluoxetine, fluticasone propionate, fluvoxamine maleate, fomepizole (4-MP), furazolidone, furosemide, gabapentin, gemcitabine, gentamicin sulfate, glimepiride, glipizide, glucagon, glucocorticoid agents, glucosamine/chondroitin sulfate, glutamine, glyburide, glycerine (oral), glycopyrrolate, gonadorelin, grisseofulvin, guaifenesin, halothane, hemoglobin glutamer-200 (oxyglobin®), heparin, hetastarch, hyaluronate sodium, hydrazaline, hydrochlorothiazide, hydrocodone bitartrate, hydrocortisone, hydromorphone, hydroxyurea, hydroxyzine, ifosfamide, imidacloprid, imidocarb dipropinate, impenem-cilastatin sodium, imipramine, inaminone lactate, insulin, interferon alfa-2a (human recombinant), iodide (sodium/potassium), ipecac (syrup), ipodate sodium, iron dextran, isoflurane, isoproterenol, isotretinoin, isoxsuprine HCl, itraconazole, ivermectin, kaolin/pectin, ketamine, ketoconazole, ketoprofen, ketorolac tromethamine, lactulose, leuprolide, levamisole, levetiracetam, levothyroxine sodium, lidocaine, lincomycin, liothyronine sodium, lisinopril, lomustine (CCNU), lufenuron, lysine, magnesium, mannitol, marbofloxacin, mechlorethamine, meclizine, meclofenamic acid, medetomidine, medium chain triglycerides, medroxyprogesterone acetate, megestrol acetate, melarsomine, melatonin, meloxican, melphalan, meperidine, mercaptopurine, meropenem, metformin, methadone, methazolamide, methenamine mandelate/hippurate, methimazole, methionine, methocarbamol, methohexital sodium, methotrexate, methoxyflurane, methylene blue, methylphenidate, methylprednisolone, metoclopramide, metoprolol, metronidaxole, mexiletine, mibolerlone, midazolam milbemycin oxime, mineral oil, minocycline, misoprostol, mitotane, mitoxantrone, morantel tartrate, morphine sulfate, moxidectin, naloxone, mandrolone decanoate, naproxen, narcotic (opiate) agonist analgesics, neomycin sulfate, neostigmine, niacinamide, nitazoxanide, nitenpyram, nitrofurantoin, nitroglycerin, nitroprusside sodium, nizatidine, novobiocin sodium, nystatin, octreotide acetate, olsalazine sodium, omeprozole, ondansetron, opiate antidiarrheals, orbifloxacin, oxacillin sodium, oxazepam, oxfendazole, oxibutynin chloride, oxymorphone, oxytretracycline, oxytocin, pamidronate disodium, pancreplipase, pancuronium bromide, paromomycin sulfate, parozetine, pencillamine, general information penicillins, penicillin G, penicillin V potassium, pentazocine, pentobarbital sodium, pentosan polysulfate sodium, pentoxifylline, pergolide mesylate, phenobarbital, phenoxybenzamine, pheylbutazone, phenylephrine, phenypropanolamine, phenyloin sodium, pheromones, parenteral phosphate, phytonadione/vitamin K-1, pimobendan, piperazine, pirlimycin, piroxicam, polysulfated glycosaminoglycan, ponazuril, potassium chloride, pralidoxime chloride, praziquantel, prazosin, prednisolone/prednisone, primidone, procainamide, procarbazine, prochlorperazine, propantheline bromide, *propionibacterium acnes* injection, propofol, propranolol, protamine sulfate, pseudoephedrine, psyllium hydrophilic mucilloid, pyrantel pamoate, pyridostigmine bromide, pyrilamine maleate, pyrimethamine, quinacrine, quinidine, ranitidine, rifampin, s-adenosyl-methionine (SAMe), saline/hyperosmotic laxative, selamectin, selegiline/l-deprenyl, sertraline, sevelamer, sevoflurane, silymarin/milk thistle, sodium bicarbonate, sodium polystyrene sulfonate, sodium stibogluconate, sodium sulfate, sodum thiosulfate, somatotropin, sotalol, spectinomycin, spironolactone, stanozolol, streptokinase, streptozocin, succimer, succinylcholine chloride, sucralfate, sufentanil citrate, sulfachlorpyridazine sodium, sulfadiazine/trimethroprim, sulfamethoxazole/trimethoprim, sulfadimentoxine, sulfadimethoxine/ormetoprim, sulfasalazine, taurine, tepoxaline, terbinafline, terbutaline sulfate, testosterone, tetracycline, thiabendazole, thiacetarsamide sodium, thiamine, thioguanine, thiopental sodium, thiotepa, thyrotropin, tiamulin, ticarcilin disodium, tiletamine/zolazepam, tilmocsin, tiopronin, tobramycin sulfate, tocamide, tolazoline, telfenamic acid, topiramate, tramadol, trimcinolone acetonide, trientine, trilostane, trimepraxine tartrate w/prednisolone, tripelennamine, tylosin, urdosiol, valproic acid, vanadium, vancomycin, vasopressin, vecuronium bromide, verapamil, vinblastine sulfate, vincristine sulfate, vitamin E/selenium, warfarin sodium, xylazine, yohimbine, zafirlukast, zidovudine (AZT), zinc acetate/zinc sulfate, zonisamide and mixtures thereof.

In one embodiment of the invention, arylpyrazole compounds such as phenylpyrazoles, e.g. fipronil, are known in the art and are suitable for combination with the compounds of the invention. Examples of such arylpyrazole compounds include but are not limited to those described in U.S. Pat. Nos. 6,001,384; 6,010,710; 6,083,519; 6,096,329; 6,174,540; 6,685,954 and 6,998,131 (all incorporated herein by reference, each assigned to Merial, Ltd., Duluth, Ga.).

In another embodiment of the invention, one or more macrocyclic lactones as monomer compounds that are described above, which act as an acaricide, anthelmintic agent and insecticide, can be added to the compositions of the invention. The macrocyclic lactones include, but are not limited to, avermectins, such as abamectin, dimadectin, doramectin, emamectin, eprinomectin, ivermectin, latidectin, lepimectin, selamectin, ML-1,694,554 and milbemycins, such as milbemectin, milbemycin D, moxidectin and nemadectin. Also included are the 5-oxo and 5-oxime derivatives of said avermectins and milbemycins.

In another embodiment of the invention, the class of acaricides or insecticides known as insect growth regulators (IGRs) can also be added to the compositions of the invention. Compounds belonging to this group are well known to the practitioner and represent a wide range of different chemical classes. These compounds all act by interfering with the development or growth of the insect pests. Insect growth regulators are described, for example, in U.S. Pat. Nos. 3,748,356, 3,818,047, 4,225,598, 4,798,837, 4,751,225, EP 0 179 022 or U.K. 2 140 010 as well as U.S. Pat. Nos. 6,096,329 and 6,685,954 (all incorporated herein by reference, both assigned to Merial Ltd., Duluth, Ga.). Examples of IGRs suitable for use include but are not limited to methoprene, pyriproxyfen, hydroprene, cyromazine, fluazuron, lufenuron, novaluron, pyrethroids, formamidines and 1-(2,6-difluorobenzoyl)-3-(2-fluoro-4-(trifluoromethyl)phenylurea.

In yet another embodiment of the invention, adulticide insecticides and acaricides can also be added to the composition of the invention. These include pyrethrins (which include cinerin I, cinerin II, jasmolin I, jasmolin II, pyrethrin I, pyrethrin II and mixtures thereof) and pyrethroids including, but not limited to, deltamethrin, cypermethrin, flumethrin cyfluthrin, and the like; and carbamates which include, but are not limited to, benomyl, carbanolate, carbaryl, carbofuran, meththiocarb, metolcarb, promacyl, propoxur, aldicarb, butocarboxim, oxamyl, thiocarboxime, thiofanox, and the like.

In some embodiments, the compositions of the invention may include one or more anthelmintic agents including, but not limited to, active agents in the benzimidazole, imidazothiazole, tetrahydropyrimidine, or organophosphate classes of compounds. In some embodiments, benzimidazoles including, but not limited to, thiabendazole, cambendazole, parbendazole, oxibendazole, mebendazole, flubendazole, fenbendazole, oxfendazole, albendazole, cyclobendazole, febantel, thiophanate and its o,o-dimethyl analogue may be included in the compositions.

In other embodiments, the compositions may include an imidazothiazole compounds including, but not limited to, tetramisole, levamisole and butamisole. In still other embodiments, the compositions of the invention may include tetrahydropyrimidine active agents including, but not limited to, pyrantel, oxantel, and morantel. Suitable organophosphate active agents include, but are not limited to, coumaphos, trichlorfon, haloxon, naftalofos and dichlorvos, heptenophos, mevinphos, monocrotophos, TEPP, and tetrachlorvinphos.

In other embodiments, the compositions may include the antinematodal compounds phenothiazine, piperazine as the neutral compound and in various salt forms, diethylcarbamazine, phenols such as disophenol, arsenicals such as arsenamide, ethanolamines such as bephenium, thenium closylate, and methyridine; cyanine dyes including pyrvinium chloride, pyrvinium pamoate and dithiazanine iodide; isothiocyanates including bitoscanate, suramin sodium, phthalofyne, and various natural products including, but not limited to, hygromycin B, α-santonin and kainic acid.

In other embodiments, the compositions of the invention may include antitrematodal agents. Suitable antitrematodal agents include, but are not limited to, the miracils such as miracil D and mirasan; praziquantel, clonazepam and its 3-methyl derivative, oltipraz, lucanthone, hycanthone, oxamniquine, amoscanate, niridazole, nitroxynil, various bisphenol compounds known in the art including hexachlorophene, bithionol, bithionol sulfoxide and menichlopholan; various salicylanilide compounds including tribromsalan, oxyclozanide, clioxanide, rafoxanide, brotianide, bromoxanide and closantel; triclabendazole, diamfenetide, clorsulon, hetolin and emetine.

Anticestodal compounds may also be advantageously used in the compositions of the invention including, but not limited to, arecoline in various salt forms, bunamidine, niclosamide, nitroscanate, paromomycin, paromomycin II, and praziquantel.

In yet other embodiments, the compositions of the invention may include other active agents that are effective against artropod parasites. Suitable active agents include, but are not limited to, bromocyclen, chlordane, DDT, endosulfan, lindane, methoxychlor, toxaphene, bromophos, bromophos-ethyl, carbophenothion, chlorfenvinphos, chlorpyrifos, crotoxyphos, cythioate, diazinon, dichlorenthion diemthoate, dioxathion, ethion, famphur, fenitrothion, fenthion, fospirate, iodofenphos, malathion, naled, phosalone, phosmet, phoxim, propetamphos, ronnel, stirofos, allethrin, cyhalothrin, cypermethrin, deltamethrin, fenvalerate, flucythrinate, permethrin, phenothrin, pyrethrins, resmethrin, benzyl benzoate, carbon disulfide, crotamiton, diflubenzuron, diphenylamine, disulfuram, isobornyl thiocyanato acetate, methroprene, monosulfuram, pirenonylbutoxide, rotenone, triphenyltin acetate, triphenyltin hydroxide, deet, dimethyl phthalate, and the compounds 1,5a,6,9,9a,9b-hexahydro-4a(4H)-dibenzofurancarboxaldehyde (MGK-11), 2-(2-ethylhexyl)-3a,4,7,7a-tetrahydro-4,7-methano-1H-isoindole-1,3(2H)dione (MGK-264), dipropyl-2,5-pyridinedicarboxylate (MGK-326) and 2-(octylthio)ethanol (MGK-874).

An antiparasitic agent that can be combined with the compound of the invention to form a composition can be a biologically active peptide or protein including, but not limited to, depsipeptides, which act at the neuromuscular junction by stimulating presynaptic receptors belonging to the secretin receptor family resulting in the paralysis and death of parasites. In one embodiment of the depsipeptide, the depsipeptide is emodepside (see Willson et al., *Parasitology*, January 2003, 126(Pt 1):79-86).

An insecticidal agent that can be combined with the compound of the invention to form a composition can be a spinosyn (e.g. spinosad) or a substituted pyridylmethyl derivative compound such as imidacloprid. Agents of this class are described above, and for example, in U.S. Pat. No. 4,742,060 or in EP 0 892 060, both of which are incorporated herein by reference. It would be well within the skill level of the practitioner to decide which individual compound can be used in the inventive formulation to treat a particular infection of an insect.

In certain embodiments, an insecticidal agent that can be combined with the compositions of the invention is a semicarbazone, such as metaflumizone.

In another embodiment, the compositions of the invention may advantageously include one or more compounds of the isoxazoline class of compounds. These active agents are described in WO 2007/079162, WO 2007/075459 and US 2009/0133319, WO 2007/070606 and US 2009/0143410, WO 2009/003075, WO 2009/002809, WO 2009/024541, WO 2005/085216 and US 2007/0066617 and WO 2008/122375, all of which are incorporated herein by reference in their entirety.

In another embodiment of the invention, nodulisporic acid and its derivatives (a class of known acaricidal, anthelminitic, anti-parasitic and insecticidal agents) may be added to the compositions of the invention. These compounds are used to treat or prevent infections in humans and animals and are described, for example, in U.S. Pat. Nos. 5,399,582, 5,962,499, 6,221,894 and 6,399,786, all of which are hereby incorporated by reference in their entirety. The compositions may include one or more of the known nodulisporic acid derivatives in the art, including all stereoisomers, such as those described in the literature cited above.

In another embodiment, anthelmintic compounds of the amino acetonitrile class (AAD) of compounds such as monepantel (ZOLVIX) and the like may be added to the compositions of the invention. These compounds are described, for example, in WO 2004/024704; Sager et al., *Veterinary Parasitology*, 2009, 159, 49-54; Kaminsky et al., *Nature vol. 452*, 13 Mar. 2008, 176-181. The compositions of the invention may also include aryloazol-2-yl cyanoethylamino compounds such as those described in US 2008/0312272 to Soll et al., which is incorporated herein in its entirety, and thioamide derivatives of these compounds, as described in U.S. patent application Ser. No. 12/582,486, filed Oct. 20, 2009, which is incorporated herein by reference. In other embodiments, the compositions may include one or more aryloazol-2-yl cyanoethylamino compounds as described in U.S. patent application Ser. No. 12/618,308, filed Nov. 13, 2009, which is incorporated herein by reference in its entirety.

The compositions of the invention may also be combined with paraherquamide compounds and derivatives of these compounds, including derquantel (see Ostlind et al., *Research in Veterinary Science*, 1990, 48, 260-61; and Ostlind et al., *Medical and Veterinary Entomology*, 1997, 11, 407-408). The paraherquamide family of compounds are known class of compounds that include a spirodioxepino indole core with activity against certain parasites (see *Tet. Lett.* 1981, 22, 135; *J. Antibiotics* 1990, 43, 1380, and *J. Antibiotics* 1991, 44, 492). In addition, the structurally related marcfortine family of compounds, such as marcfortines A-C, are also known and may be combined with the formulations of the invention (see *J. Chem. Soc.—Chem. Comm.* 1980, 601 and *Tet. Lett.* 1981, 22, 1977). Further references to the paraherquamide derivatives can be found, for example, in WO 91/09961, WO 92/22555, WO 97/03988, WO 01/076370, WO 09/004,432, U.S. Pat. Nos. 5,703,078 and 5,750,695, all of which are hereby incorporated by reference in their entirety.

In a further aspect, the invention relates to a method preventing or treating a parasitic infection or infestation in livestock comprising administering to the livestock an anti-parasitic formulation as described herein.

The invention is also directed toward a method of treating an animal, advantageously a livestock animal, against ectoparasitic infection by administering an ectoparasiticidally effective amount of the composition of the invention. Mammals which can be treated include but are not limited to humans, cats, dogs, cattle, chickens, cows, deer, goats, horses, llamas, pigs, sheep and yaks. In one embodiment of the invention, the mammals treated are humans, cats or dogs.

In one embodiment for treatment against ectoparasites such as ticks and fleas, the ectoparasite is one or more insect or arachnid including, but not limited to, those of the genera *Ctenocephalides, Rhipicephalus, Dermacentor, Ixodes, Boophilus, Ambylomma, Haemaphysalis, Hyalomma, Sarcoptes, Psoroptes, Otodectes, Chorioptes, Hypoderma, Damalinia, Linognathus, Haematopinus, Solenoptes, Trichodectes,* and *Felicola.*

In another embodiment for the treatment against ectoparasites, the ectoparasite includes those from the genera *Ctenocephalides, Rhipicephalus, Dermacentor, Ixodes* and/or *Boophilus*. The ectoparasites treated include but are not limited to fleas, ticks, mites, mosquitoes, flies, lice, blowfly and combinations thereof. Specific examples include but are not limited to cat and dog fleas (*Ctenocephalides felts, Ctenocephalides* sp. and the like), ticks (*Rhipicephalus* sp., *Ixodes* sp., *Dermacentor* sp., *Amblyoma* sp. and the like), and mites (*Demodex* sp., *Sarcoptes* sp., *Otodectes* sp. and the like), lice (*Trichodectes* sp., *Cheyletiella* sp., *Lignonathus* sp., and the like), mosquitoes (*Aedes* sp., *Culex* sp., *Anopheles* sp., and the like) and flies (*Hematobia* sp., *Musca* sp., *Stomoxys* sp., *Dematobia* sp., *Cochliomyia* sp., and the like).

Additional examples of ectoparasites include but are not limited to the tick genus *Boophilus*, especially those of the species *microplus* (cattle tick), *decoloratus* and *annulatus*; myiases such as *Dermatobia hominis* (known as Berne in Brazil) and *Cochliomyia hominivorax* (greenbottle); sheep myiases such as *Lucilia sericata, Lucilia cuprina* (known as blowfly strike in Australia, New Zealand and South Africa). Flies proper, namely those whose adult constitutes the parasite, such as *Haematobia irritans* (horn fly); lice such as *Linognathus vitulorum, Damalinia, Solenoptes*, etc.; and mites such as *Sarcoptes scabiei* and *Psoroptes ovis*. The above list is not exhaustive and other ectoparasites are well known in the art to be harmful to animals and humans. These include, for example migrating dipterous larvae.

The compositions of the invention can also be used to treat against endoparasites including, but not limited to, *Anaplocephala, Ancylostoma, Anecator, Ascaris, Capillaria, Cooperia, Dipylidium, Dirofilaria, Echinococcus, Enterobius, Fasciola, Haemonchus, Oesophagostumum, Ostertagia, Toxocara, Strongyloides, Toxascaris, Trichinella, Trichuris,* and *Trichostrongylus.*

In another embodiment of the invention, the compounds and compositions of the invention are suitable for controlling pests including *Blatella germanica, Heliothis virescens, Leptinotarsa decemlineata, Tetramorium caespitum* and combinations thereof.

The phytoparasitic nematodes include, for example, *Anguina* spp., *Aphelenchoides* spp., *Belonoaimus* spp., *Bursaphelenchus* spp., *Ditylenchus dipsaci, Globodera* spp., *Heliocotylenchus* spp., *Heterodera* spp., *Longidorus* spp., *Meloidogyne* spp., *Pratylenchus* spp., *Radopholus similis, Rotylenchus* spp., *Trichodorus* spp., *Tylenchorhynchus* spp., *Tylenchulus* spp., *Tylenchulus semipenetrans, Xiphinema* spp.

In addition, with or without the other pesticidal agents added to the composition, the invention can also be used to treat other pests which include but are not limited to pests:

(1) from the order of Isopoda, for example *Oniscus asellus, Armadillidium vulgare* and *Porcellio scaber;*

(2) from the order of Diplopoda, for example *Blaniulus guttulatus;*

(3) from the order of Chilopoda, for example *Geophilus carpophagus* and *Scutigera* spp.;

(4) from the order of Symphyla, for example *Scutigerella immaculata;*

(5) from the order of Thysanura, for example *Lepisma saccharina;*

(6) from the order of Collembola, for example *Onychiurus armatus;*

(7) from the order of Blattaria, for example *Blatta orientalis, Periplaneta americana, Leucophaea maderae* and *Blattella germanica;*

(8) from the order of *Hymenoptera*, for example *Diprion* spp., *Hoplocampa* spp., *Lasius* spp., *Monomorium pharaonis* and *Vespa* spp.;

(9) from the order of *Siphonaptera*, for example *Xenopsylla cheopis, Ceratophyllus* spp., and *Ctenocephalides* spp.;

(10) from the order of Anoplura (Phthiraptera), for example, *Damalinia* spp., *Haematopinus* spp., *Linognathus* spp., *Pediculus* spp., *Trichodectes* spp.;

(11) from the class of Arachnida, for example, *Acarus siro, Aceria sheldoni, Aculops* spp., *Aculus* spp., *Amblyomma* spp., *Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp.,

*Eriophyes* spp., *Hemitarsonemus* spp., *Hyalomma* spp., *Ixodes* spp., *Latrodectus mactans*, *Metatetranychus* spp., *Oligonychus* spp., *Ornithodoros* spp., *Panonychus* spp., *Phyllocoptruta oleivora*, *Polyphagotarsonemus latus*, *Psoroptes* spp., *Rhipicephalus* spp., *Rhizoglyphus* spp., *Sarcoptes* spp., *Scorpio maurus*, *Stenotarsonemus* spp., *Tarsonemus* spp., *Tetranychus* spp., *Vasates lycopersici.*;

(12) from the class of Bivalva, for example, *Dreissena* spp.;

(13) from the order of Coleoptera, for example, *Acanthoscelides obtectus*, *Adoretus* spp., *Agelastica alni*, *Agriotes* spp., *Amphimallon solstitialis*, *Anobium punctatum*, *Anoplophora* spp., *Anthonomus* spp., *Anthrenus* spp., *Apogonia* spp., *Atomaria* spp., *Attagenus* spp., *Bruchidius obtectus*, *Bruchus* spp., *Ceuthorhynchus* spp., *Cleonus mendicus*, *Conoderus* spp., *Cosmopolites* spp., *Costelytra zealandica*, *Curculio* spp., *Cryptorhynchus lapathi*, *Dermestes* spp., *Diabrotica* spp., *Epilachna* spp., *Faustinus cubae*, *Gibbium psylloides*, *Heteronychus arator*, *Hylamorpha elegans*, *Hylotrupes bajulus*, *Hypera postica*, *Hypothenemus* spp., *Lachnosterna consanguinea*, *Leptinotarsa decemlineata*, *Lissorhoptrus oryzophilus*, *Lixus* spp., *Lyctus* spp., *Meligethes aeneus*, *Melolontha melolontha*, *Migdolus* spp., *Monochamus* spp., *Naupactus xanthographus*, *Niptus hololeucus*, *Oryctes rhinoceros*, *Oryzaephilus surinamensis*, *Otiorrhynchus sulcatus*, *Oxycetonia jucunda*, *Phaedon cochleariae*, *Phyllophaga* spp., *Popillia japonica*, *Premnotrypes* spp., *Psylliodes chrysocephala*, *Ptinus* spp., *Rhizobius ventralis*, *Rhizopertha dominica*, *Sitophilus* spp., *Sphenophorus* spp., *Sternechus* spp., *Symphyletes* spp., *Tenebrio molitor*, *Tribolium* spp., *Trogoderma* spp., *Tychius* spp., *Xylotrechus* spp., *Zabrus* spp.;

(14) from the order of Diptera, for example, *Aedes* spp., *Anopheles* spp., *Bibio hortulanus*, *Calliphora erythrocephala*, *Ceratitis capitata*, *Chrysomyia* spp., *Cochliomyia* spp., *Cordylobia anthropophaga*, *Culex* spp., *Cuterebra* spp., *Dacus oleae*, *Dermatobia hominis*, *Drosophila* spp., *Fannia* spp., *Gastrophilus* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit*, *Pegomyia hyoscyami*, *Phorbia* spp., *Stomoxys* spp., *Tabanus* spp., *Taenia* spp., *Tipula paludosa*, *Wohlfahrtia* spp.;

(15) from the class of Gastropoda, for example, *Anion* spp., *Biomphalaria* spp., *Bulinus* spp., *Deroceras* spp., *Galba* spp., *Lymnaea* spp., *Oncomelania* spp., *Succinea* spp.;

(16) from the class of helminths, for example, *Ancylostoma duodenale*, *Ancylostoma ceylanicum*, *Acylostoma braziliensis*, *Ancylostoma* spp., *Ascaris lubricoides*, *Ascaris* spp., *Brugia malayi*, *Brugia timori*, *Bunostomum* spp., *Chabertia* spp., *Clonorchis* spp., *Cooperia* spp., *Dicrocoelium* spp, *Dictyocaulus filaria*, *Diphyllobothrium latum*, *Dracunculus medinensis*, *Echinococcus granulosus*, *Echinococcus multilocularis*, *Enterobius vermicularis*, *Faciola* spp., *Haemonchus* spp., *Heterakis* spp., *Hymenolepis nana*, *Hyostrongulus* spp., *Loa Loa*, *Nematodirus* spp., *Oesophagostomum* spp., *Opisthorchis* spp., *Onchocerca volvulus*, *Ostertagia* spp., *Paragonimus* spp., *Schistosomen* spp., *Strongyloides fuelleborni*, *Strongyloides stercoralis*, *Stronyloides* spp., *Taenia saginata*, *Taenia solium*, *Trichinella spiralis*, *Trichinella nativa*, *Trichinella britovi*, *Trichinella nelsoni*, *Trichinella pseudopsiralis*, *Trichostrongulus* spp., *Trichuris trichuria*, *Wuchereria bancrofti*.;

(17) from the order of Heteroptera, for example, *Anasa tristis*, *Antestiopsis* spp., *Blissus* spp., *Calocoris* spp., *Campylomma livida*, *Cavelerius* spp., *Cimex* spp., *Creontiades dilutus*, *Dasynus piperis*, *Dichelops furcatus*, *Diconocoris hewetti*, *Dysdercus* spp., *Euschistus* spp., *Eurygaster* spp., *Heliopeltis* spp., *Horcias nobilellus*, *Leptocorisa* spp., *Leptoglossus phyllopus*, *Lygus* spp., *Macropes excavatus*, Miridae, *Nezara* spp., *Oebalus* spp., Pentomidae, *Piesma quadrata*, *Piezodorus* spp., *Psallus seriatus*, *Pseudacysta persea*, *Rhodnius* spp., *Sahlbergella singularis*, *Scotinophora* spp., *Stephanitis nashi*, *Tibraca* spp., *Triatoma* spp.;

(18) from the order of Homoptera, for example, *Acyrthosipon* spp., *Aeneolamia* spp., *Agonoscena* spp., *Aleurodes* spp., *Aleurolobus barodensis*, *Aleurothrixus* spp., *Amrasca* spp., *Anuraphis cardui*, *Aonidiella* spp., *Aphanostigma pini*, *Aphis* spp., *Arboridia apicalis*, *Aspidiella* spp., *Aspidiotus* spp., *Atanus* spp., *Aulacorthum solani*, *Bemisia* spp., *Brachycaudus helichrysii*, *Brachycolus* spp., *Brevicoryne brassicae*, *Calligypona marginata*, *Carneocephala fulgida*, *Ceratovacuna lanigera*, Cercopidae, *Ceroplastes* spp., *Chaetosiphon fragaefolii*, *Chionaspis tegalensis*, *Chlorita onukii*, *Chromaphis juglandicola*, *Chrysomphalus ficus*, *Cicadulina mbila*, *Coccomytilus halli*, *Coccus* spp., *Cryptomyzus ribis*, *Dalbulus* spp., *Dialeurodes* spp., *Diaphorina* spp., *Diaspis* spp., *Doralis* spp., *Drosicha* spp., *Dysaphis* spp., *Dysmicoccus* spp., *Empoasca* spp., *Eriosoma* spp., *Erythroneura* spp., *Euscelis bilobatus*, *Geococcus coffeae*, *Homalodisca coagulata*, *Hyalopterus arundinis*, *Icerya* spp., *Idiocerus* spp., *Idioscopus* spp., *Laodelphax striatellus*, *Lecanium* spp., *Lepidosaphes* spp., *Lipaphis erysimi*, *Macrosiphum* spp., *Mahanarva fimbriolata*, *Melanaphis sacchari*, *Metcalfiella* spp., *Metopolophium dirhodum*, *Monellia costalis*, *Monelliopsis pecanis*, *Myzus* spp., *Nasonovia ribisnigri*, *Nephotettix* spp., *Nilaparvata lugens*, *Oncometopia* spp., *Orthezia praelonga*, *Parabemisia myricae*, *Paratrioza* spp., *Parlatoria* spp., *Pemphigus* spp., *Peregrinus maidis*, *Phenacoccus* spp., *Phloeomyzus passerinii*, *Phorodon humuli*, *Phylloxera* spp., *Pinnaspis aspidistrae*, *Planococcus* spp., *Protopulvinaria pyriformis*, *Pseudaulacaspis pentagona*, *Pseudococcus* spp., *Psylla* spp., *Pteromalus* spp., *Pyrilla* spp., *Quadraspidiotus* spp., *Quesada gigas*, *Rastrococcus* spp., *Rhopalosiphum* spp., *Saissetia* spp., *Scaphoides titanus*, *Schizaphis graminum*, *Selenaspidus articulatus*, *Sogata* spp., *Sogatella furcifera*, *Sogatodes* spp., *Stictocephala festina*, *Tenalaphara malayensis*, *Tinocallis caryaefoliae*, *Tomaspis* spp., *Toxoptera* spp., *Trialeurodes vaporariorum*, *Trioza* spp., *Typhlocyba* spp., *Unaspis* spp., *Viteus vitifolii.*;

(19) from the order of Isoptera, for example, *Reticulitermes* spp., *Odontotermes* spp.;

(20) from the order of Lepidoptera, for example, *Acronicta major*, *Aedia leucomelas*, *Agrotis* spp., *Alabama argillacea*, *Anticarsia* spp., *Barathra brassicae*, *Bucculatrix thurberiella*, *Bupalus piniarius*, *Cacoecia podana*, *Capua reticulana*, *Carpocapsa pomonella*, *Chematobia brumata*, *Chilo* spp., *Choristoneura fumiferana*, *Clysia ambiguella*, *Cnaphalocerus* spp., *Earias insulana*, *Ephestia kuehniella*, *Euproctis chrysorrhoea*, *Euxoa* spp., *Feltia* spp.,

*Galleria mellonella, Helicoverpa* spp., *Heliothis* spp., *Hofmannophila pseudospretella, Homona magnanima, Hyponomeuta padella, Laphygma* spp., *Lithocolletis blancardella, Lithophane antennata, Loxagrotis albicosta, Lymantria* spp., *Malacosoma neustria, Mamestra brassicae, Mocis repanda, Mythimna separata, Oria* spp., *Oulema oryzae, Panolis flammea, Pectinophora gossypiella, Phyllocnistis citrella, Pieris* spp., *Plutella xylostella, Prodenia* spp., *Pseudaletia* spp., *Pseudoplusia includens, Pyrausta nubilalis, Spodoptera* spp., *Thermesia gemmatalis, Tinea pellionella, Tineola bisselliella, Tortrix viridana, Trichoplusia* spp.;

(21) from the order of Orthoptera, for example, *Acheta domesticus, Blatta orientalis, Blattella germanica, Gryllotalpa* spp., *Leucophaea maderae, Locusta* spp., *Melanoplus* spp., *Periplaneta americana, Schistocerca gregaria.*;

(22) from the order of Thysanoptera, for example, *Baliothrips biformis, Enneothrips flavens, Frankliniella* spp., *Heliothrips* spp., *Hercinothrips femoralis, Kakothrips* spp., *Rhipiphorothrips cruentatus, Scirtothrips* spp., *Taeniothrips cardamoni, Thrips* spp.;

(23) from the class of Protozoa, for example, *Eimeria* spp.

If appropriate, the compounds according to the invention can, at certain concentrations or application rates, also be used as herbicides, safeners, growth regulators or agents to improve plant properties, or as microbicides, for example as fungicides, antimycotics, bactericides, viricides (including agents against viroids) or as agents against MLO (mycoplasma-like organisms) and RLO (rickettsia-like organisms). If appropriate, they can also be employed as intermediates or precursors for the synthesis of other active compounds.

In each aspect of the invention, the compounds and compositions of the invention can be applied against a single pest or combinations thereof.

The active compounds according to the invention, in combination with good plant tolerance and favourable toxicity to warm-blooded animals and being tolerated well by the environment, are suitable for protecting plants and plant organs, for increasing the harvest yields, for improving the quality of the harvested material and for controlling animal pests, in particular insects, arachnids, helminths, nematodes and molluscs, which are encountered in agriculture, in horticulture, in animal husbandry, in forests, in gardens and leisure facilities, in the protection of stored products and of materials, and in the hygiene sector. They may be preferably employed as plant protection agents. They are active against normally sensitive and resistant species and against all or some stages of development.

The above description of the invention is intended to be illustrative and not limiting. Various changes or modifications in the embodiments described may occur to those skilled in the art. These can be made without departing from the scope or spirit of the invention.

The invention is further described, for example, in the following non-limiting examples. Better understanding of the present invention and of its many advantages will be had from the following non-limiting examples, given by way of illustration. It will be apparent to those skilled in the art that these examples are non-limiting, and that similar methods to achieve the following transformations are possible.

The following examples describe the preparation of various macrocyclic lactone dimers of formula (I) derived from avermectin B1 monomers using various groups $R_9$ and $R_{10}$ and linkers L. The term "avermectin B1 residue" in the following examples refers to the following structure bonded at the 4'-position to the oxygen atom of the saccharide group, where R is iso-propyl or sec-butyl. For simplicity, the examples below depict the preparation of compounds having only a sec-butyl group at the 25-position of the molecule. However, all of the compounds described in the examples comprise avermectin or milbemycin monomers substituted with a mixture of iso-propyl and sec-butyl substitutents at this position. Further, the spectral data in the examples only reflects the major component having a sec-butyl substituent.

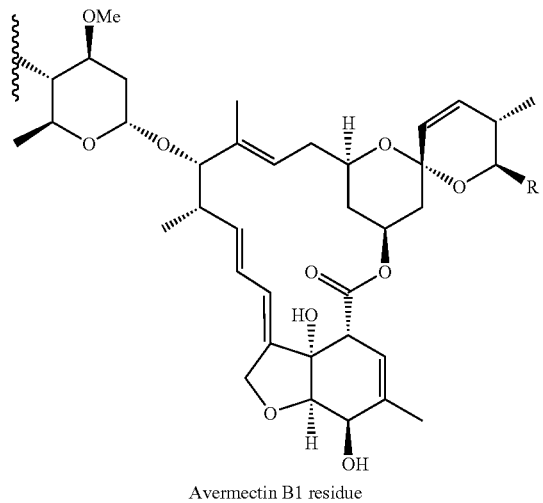

Avermectin B1 residue

R = iso-propyl or sec-butyl

Similarly, the term "5-O-TBS avermectin B1 residue" refers to the avermectin B1 residue where the 5-hydroxyl group has been protected as the tert-butyldimethylsilyl ether, having the structure shown below:

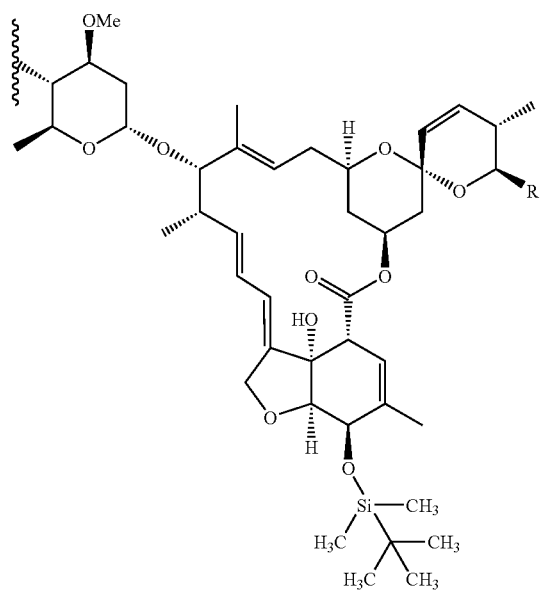

R = iso-propyl or sec-butyl

EXAMPLE 1
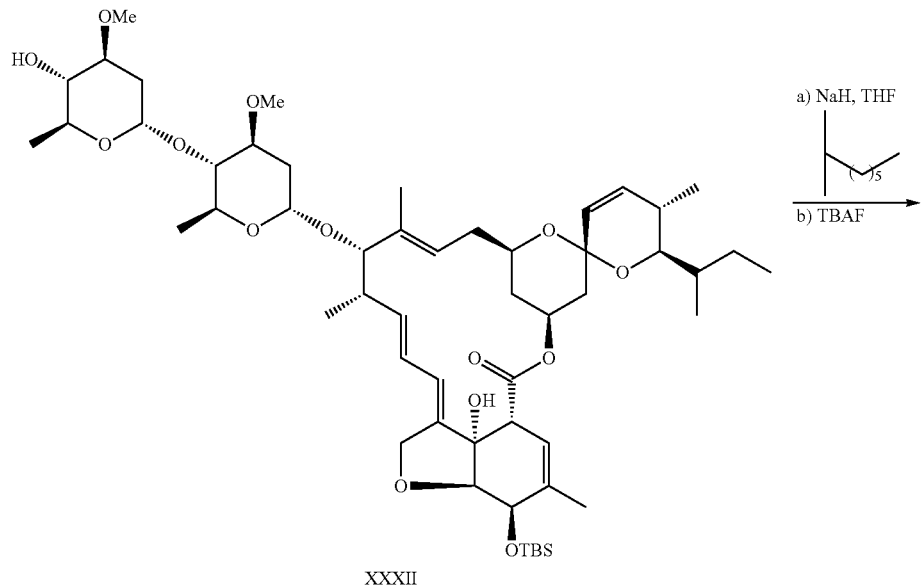
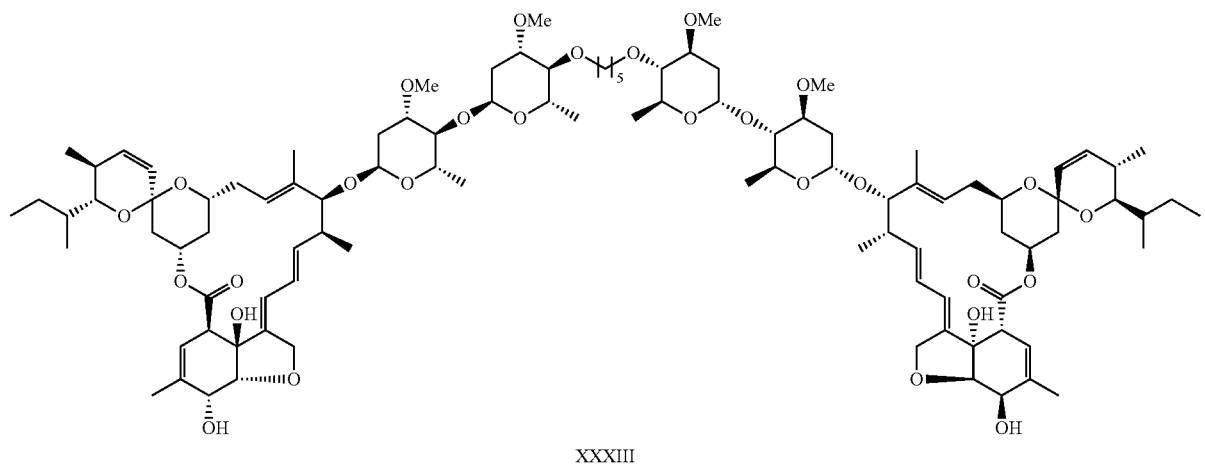
An avermectin compound (XXXII) with the 5-hydroxyl protected and the 4"-hydroxy free may react with a diiodide under basic conditions to form a dimeric compound. Deprotection of the 5-hydroxyl group in the presence of a reagent such as tetrabutylammonium fluoride may then lead to a desired final product (XXXIII).

EXAMPLE 2
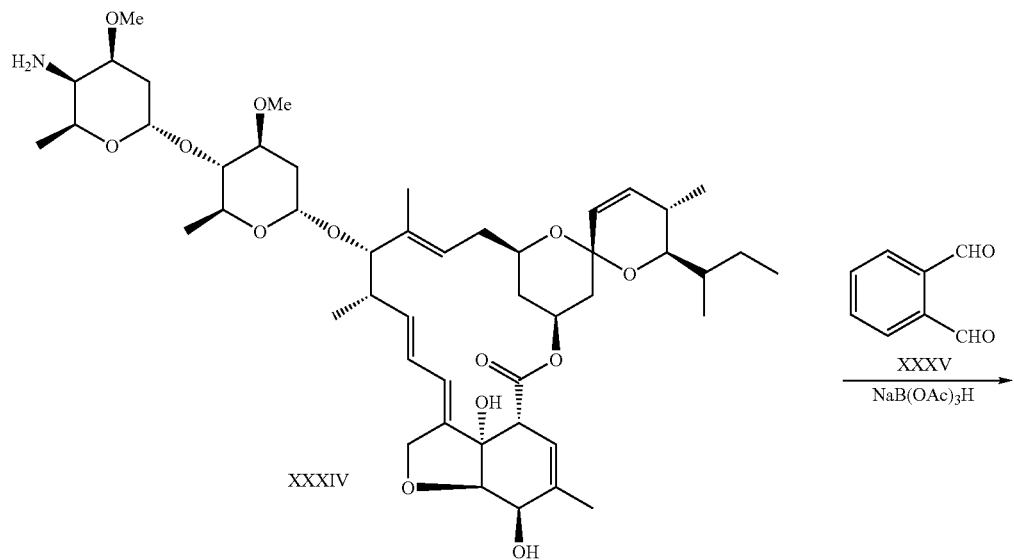
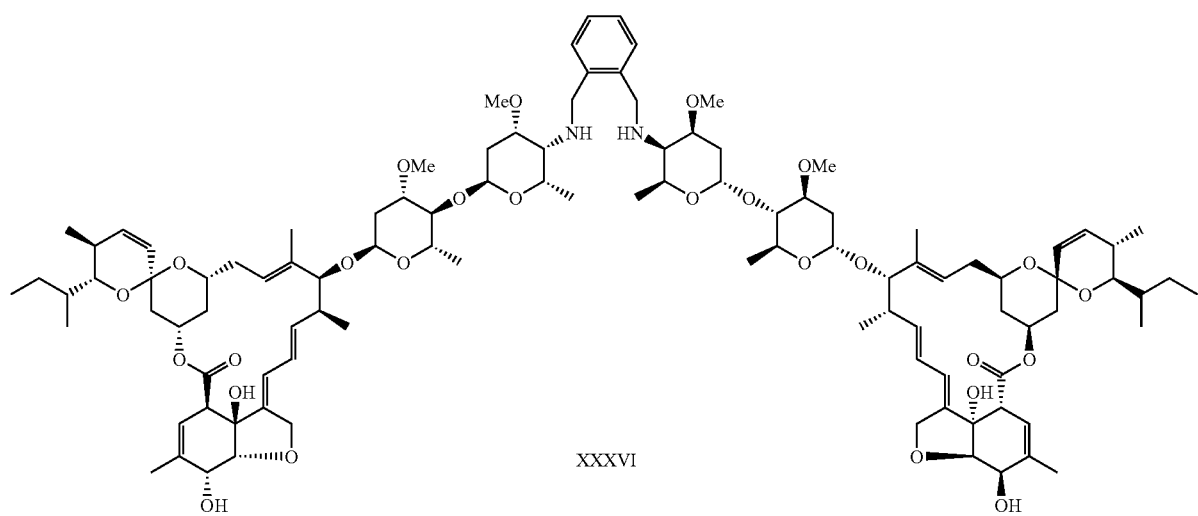
Two molecules of a 4"-epiamino avermectin derivative (XXXIV) may be converted to a dimeric product (XXXVI) with a bis-aldehyde compound (XXXV) under reductive amination conditions.
EXAMPLE 3

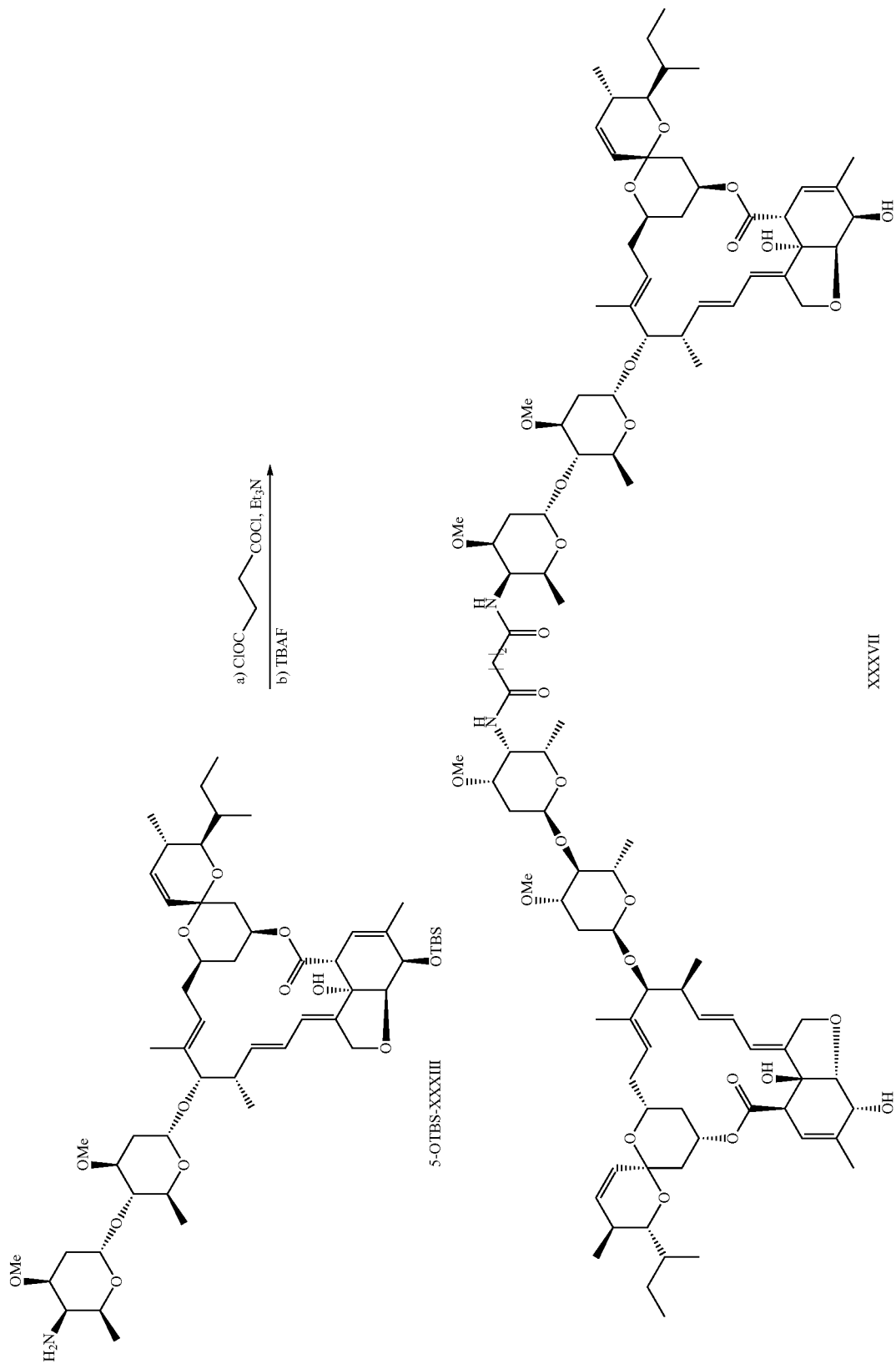

Two molecules of a 5-O-TBS-4"-epiamino avermectin derivative (5-O-TBS-XXXIII) may be converted to a dimeric product (XXXVII) with a bis-acyl chloride under basic conditions. Protection of the 5-hydroxy group with a protecting group such as t-butyldimethylsilyl may or may not be necessary prior to formation of the dimeric product

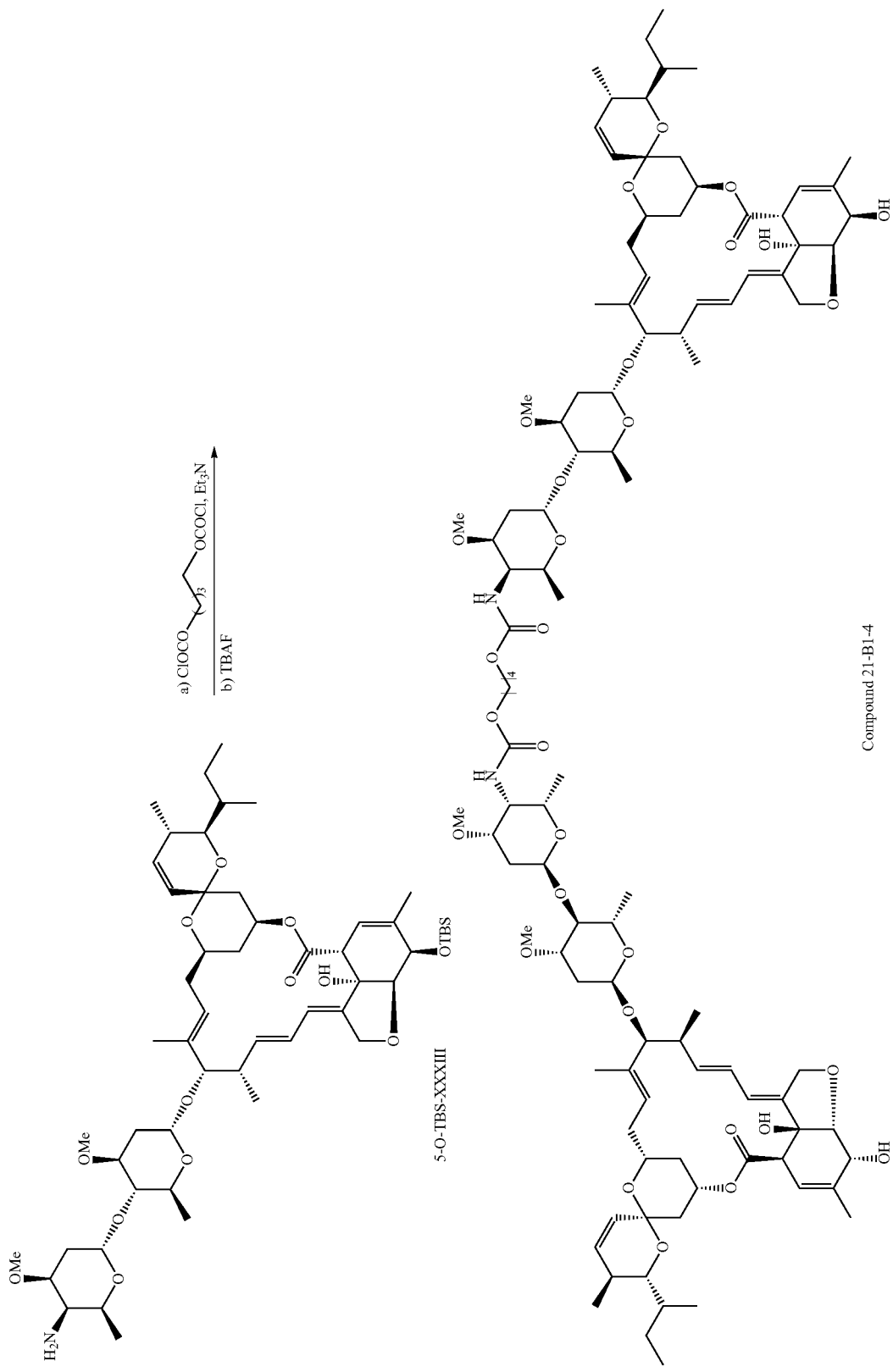

Two molecules of a 5-O-TBS-4"-epi amino avermectin XXXIII may be converted to a dimeric product 21-B1-4 (see Table 3) with a bis-chloroformate such under basic conditions. Protection of the 5-hydroxy group with a protecting group such as t-butyldimethylsilyl may or may not be necessary prior to formation of the dimeric product.

EXAMPLE 5

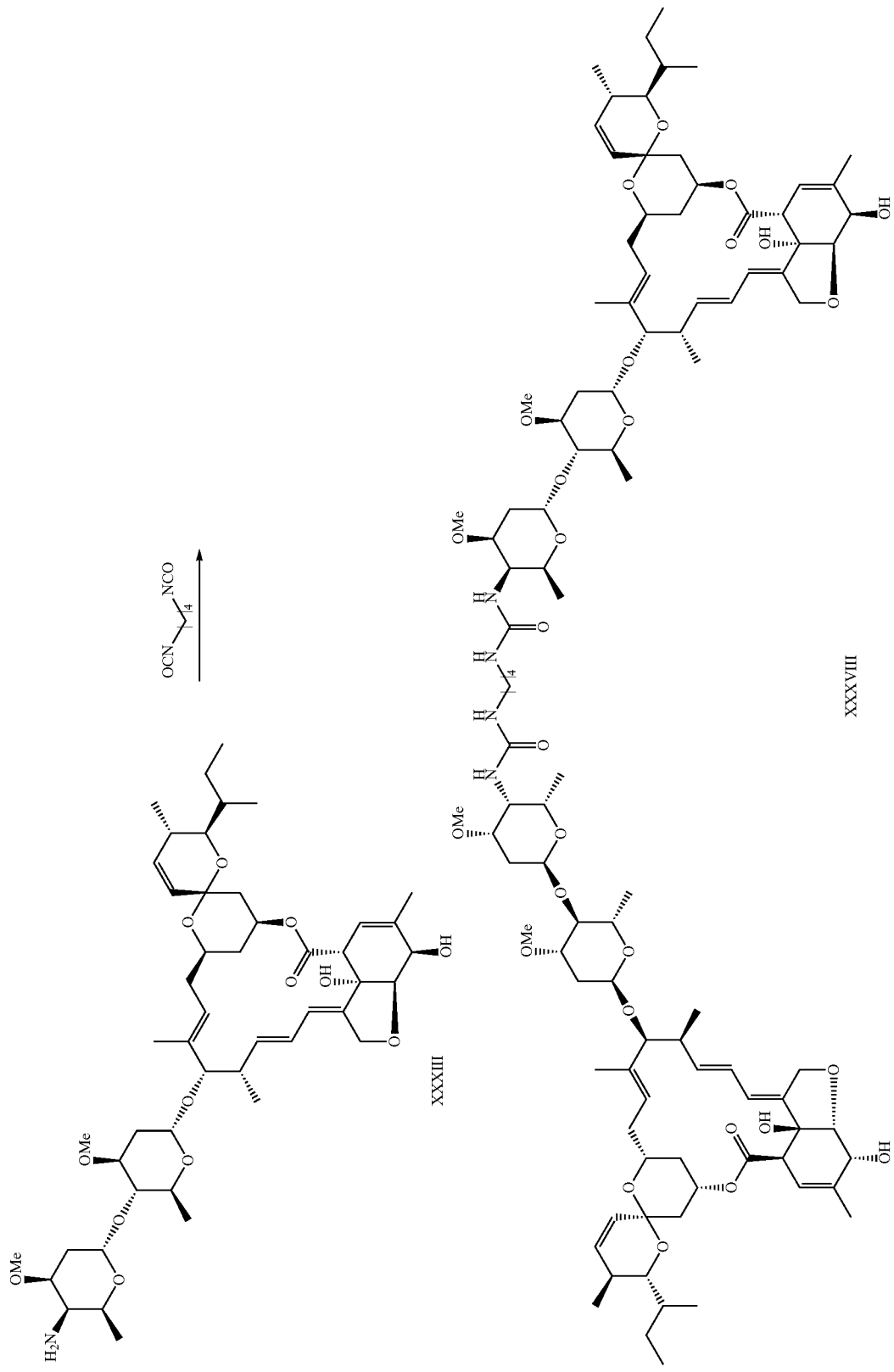

Two molecules of a 4"-epiamino avermectin derivative XXXIII convert to a dimeric product (XXXVIII) with a bis-is

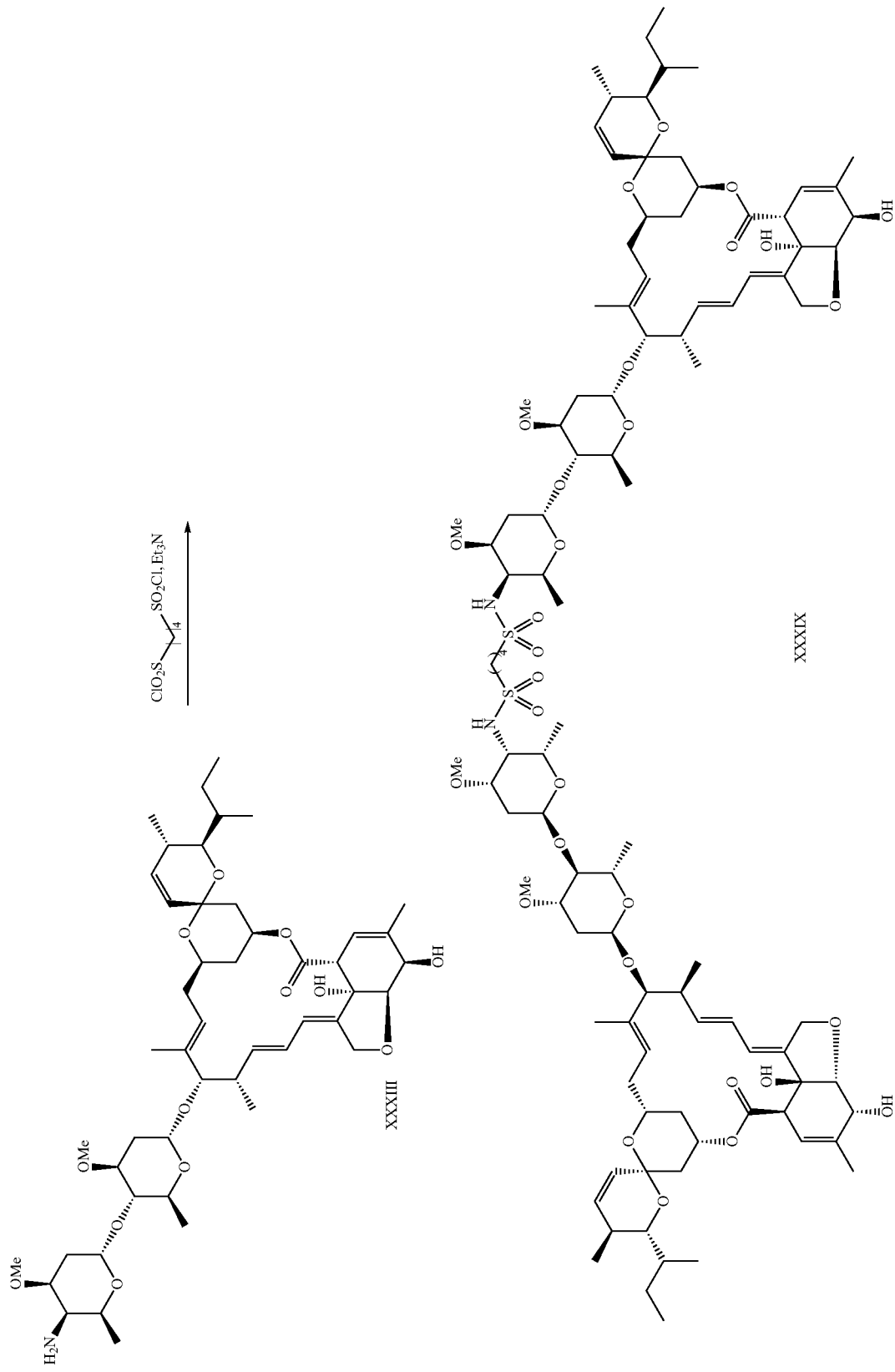

Two molecules of a 4"-epiamino avermectin derivative convert to a dimeric product (XXXIX) with a bis-sulfonyl chloride under basic conditions.

EXAMPLE 7

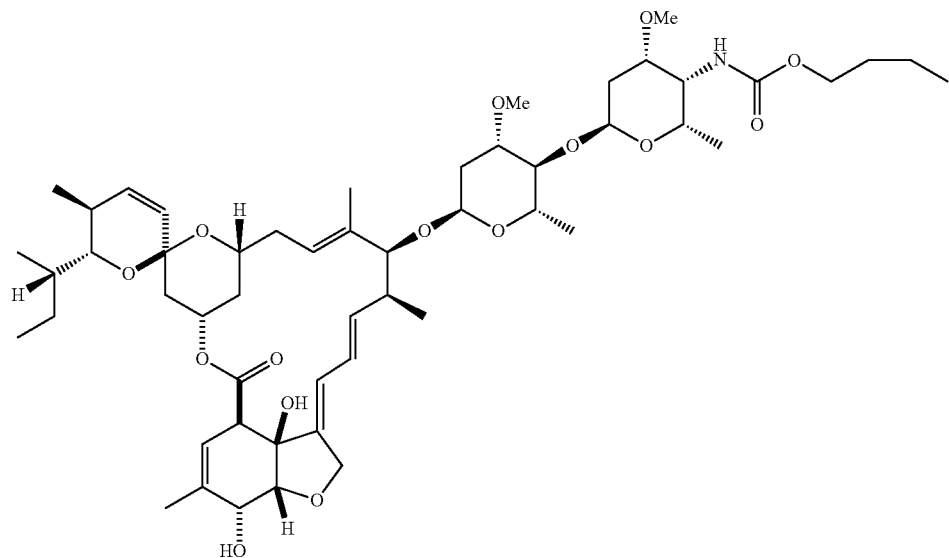

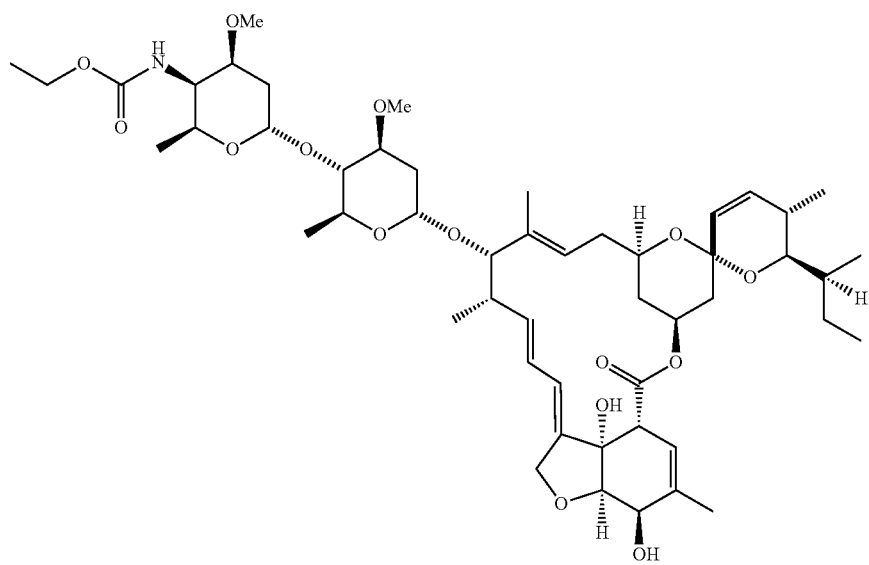

Compound 21-B1-4 (L = $C_4$alkylene)

Compound 21-B1-4 was prepared by reacting a 5-O-tert-butyldimethylsilyl-protected 4"-epi amino avermectin compound with a bis-chloroformate reagent in the presence of the bulky base diisopropylethylamine (DIEA) and dimethylaminopyridine (DMAP). The desired product was formed after removing the silyl protecting group.

Step 1:

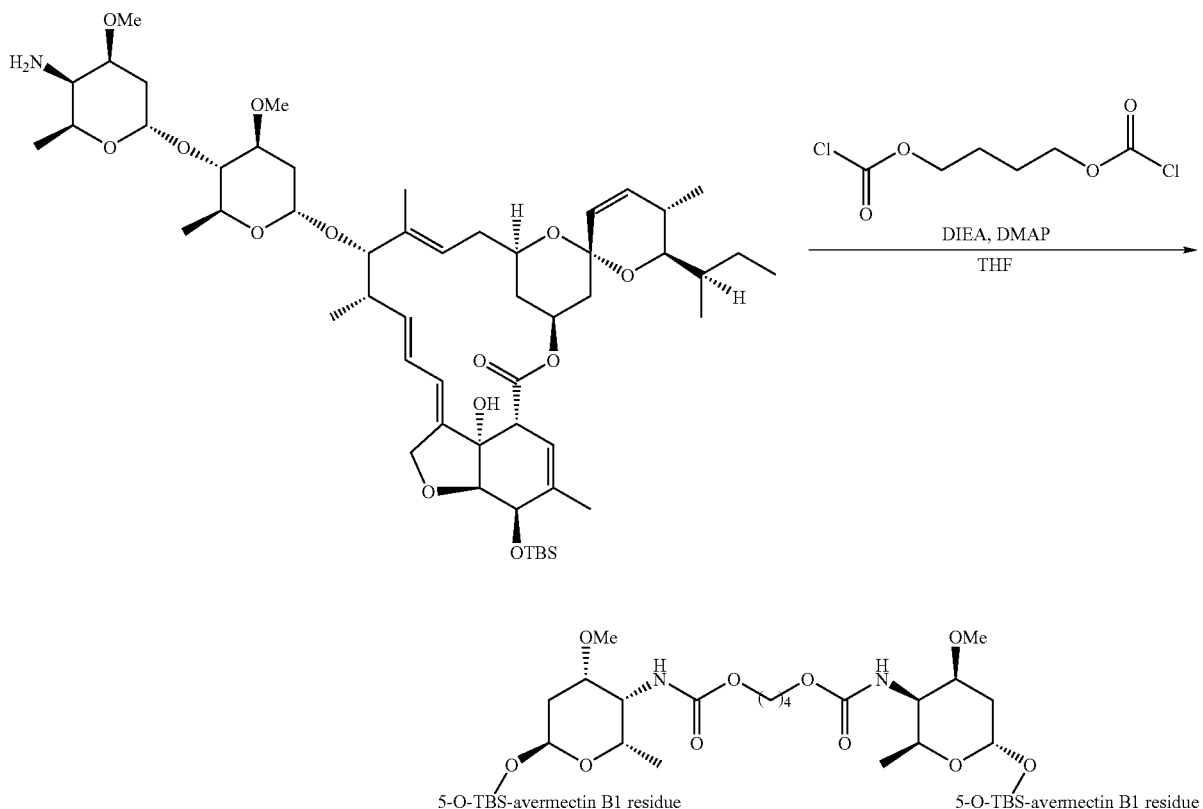

1,4-Butanediol bis(chloroformate) (29 mg, 0.135 mmol, 1.0 equiv) was added to a solution of 4"-epi-amino-5-O-TBS-4"-desoxy-avermectin $B_1$ (400 mg, 0.406 mmol, 3.0 equiv), N-ethyl-N-isopropylpropan-2-amine (70 mg, 0.54 mmol, 4.0 equiv) and N,N-dimethylpyridin-4-amine (4 mg, 0.033 mmol, 0.24 equiv) in tetrahydrofuran (10 mL) at 0° C., then left at room temperature overnight. Water (10 mL) was added to the mixture and extracted with ethyl acetate (10 mL×3). The combined organic phases were dried over anhydrous sodium sulfate. After filtration and concentration, the residue was purified by column chromatography on silica gel with ethyl acetate/petroleum ether (1:2) as eluent to give 150 mg (53%) of the 5-O-TBS protected dimer compound as a yellow powder.

Step 2:

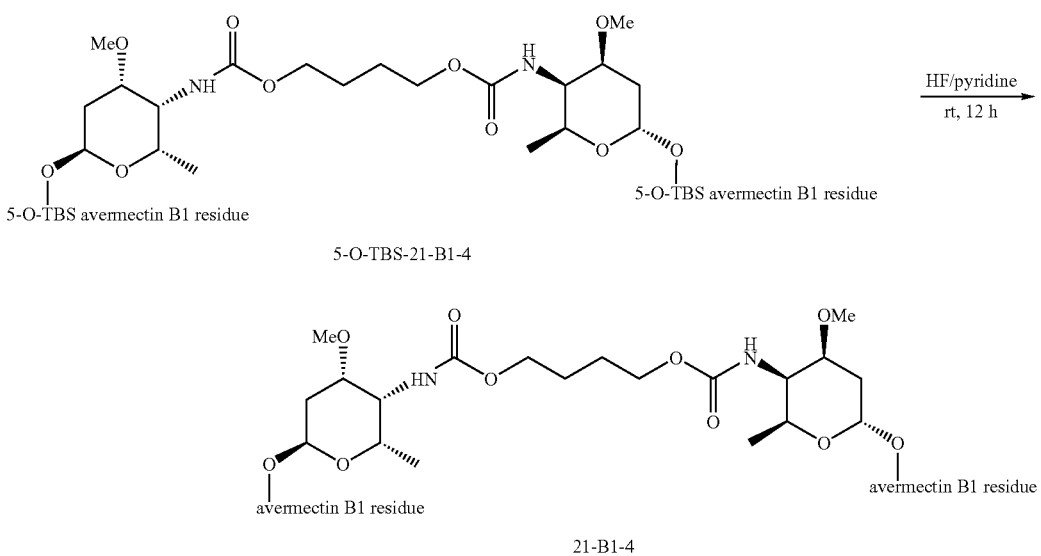

A solution of the 5-O-TBS protected dimer from Step 1 (150 mg, 0.071 mmol, 1.00 equiv) in 4 mL of HF-pyridine solution (prepared by diluting 25 g of 70% HF-pyridine solution with 27.5 mL of dry tetrahydrofuran, then adding 12.5 mL of pyridine at 0° C. and stirring the suspension for 5 min.) was stirred overnight at room temperature. The pH value of the reaction solution was adjusted to 6 with saturated aqueous sodium bicarbonate. The resulting solution was extracted with ethyl acetate (10 mL×3) and the organic layers combined dried over anhydrous sodium sulfate, filtered and concentrated under vacuum to give 95 mg (71%) of the macrocyclic lactone dimer compound 21-B1-4 as a yellowish solid. $^1$H NMR (400 MHz, CDCl$_3$) δ 5.87 (br d, J=10.0 Hz, 2H), 5.78 (d, J=1.5 Hz, 2H), 5.76-5.70 (m, 4H), 5.57 (dd, J=10.0, 2.4 Hz, 2H), 5.44 (br s, 2H), 5.40 (d, J=4.0 Hz, 2H), 5.37 (m, 2H), 4.99 (br d, J=7.0 Hz, 2H), 4.78 (d, J=2.8 Hz, 2H), 4.70 (s, 4H), 4.30 (d, J=6.0 Hz, 2H), 4.15-4.02 (m, 4H), 3.98 (d, J=6.5 Hz, 2H), 3.93 (s, 2H), 3.90-3.78 (m, 6H), 3.70-3.56 (m, 4H), 3.48 (d, J=10.0 Hz, 2H), 3.44 (s, 6H), 3.43 (s, 6H), 3.30 (d, J=2.0 Hz, 2H), 3.22 (t, J=9.0 Hz, 2H), 2.53 (m, 2H), 2.32-2.20 (m, 10H), 2.02 (dd, J=12.0, 3.0 Hz, 2H), 1.89 (s, 6H), 1.78 (dd, J=10.5, 2.5 Hz, 2H), 1.68-1.43 (m, 16H), 1.49 (s, 6H), 1.25 (d, J=6.5 Hz, 6H), 1.18 (d, J=6.5 Hz, 6H), 1.17 (d, J=7.0 Hz, 6H), 0.95 (t, J=7.6 Hz, 6H), 0.94 (d, J=7.0 Hz, 6H), 0.92 (d, J=7.5 Hz, 6H), 0.90 (dd, J=12.5, 6.5 Hz, 2H). LC-MS (electrospray) m/z 1908 (M+Na$^+$).

EXAMPLE 8

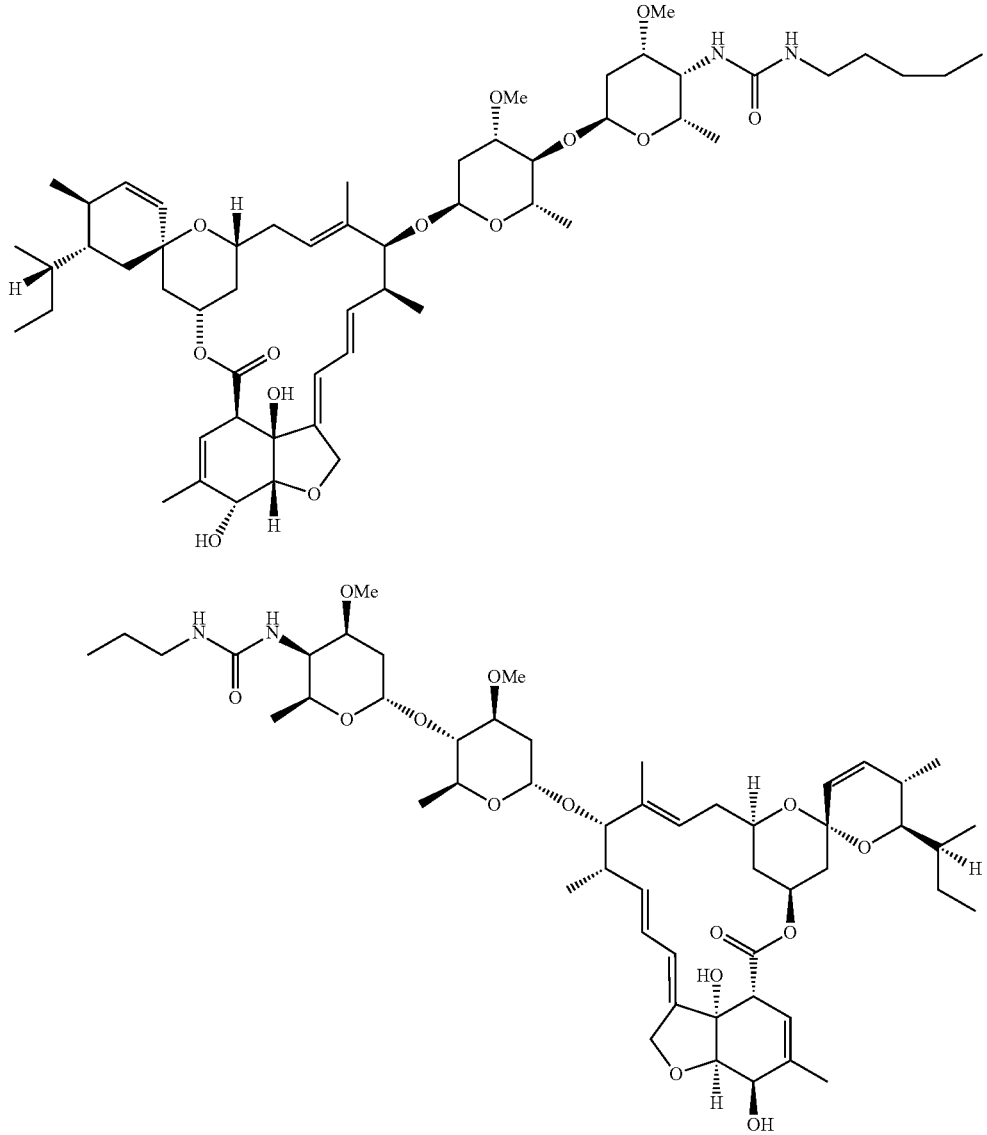

Compound 22-B1-6 (L = C$_6$ alkylene)

A bis-urea-linked compound was prepared by reacting 4"-epi-amino-5-O-TBS-4"-desoxy-avermectin B$_1$ with a bis-carboxylic acid in the presence of the peptide coupling agent diphenylphosphoryl azide (DPPA). Removal of the silyl protecting group provided the desired compound.

Step 1:

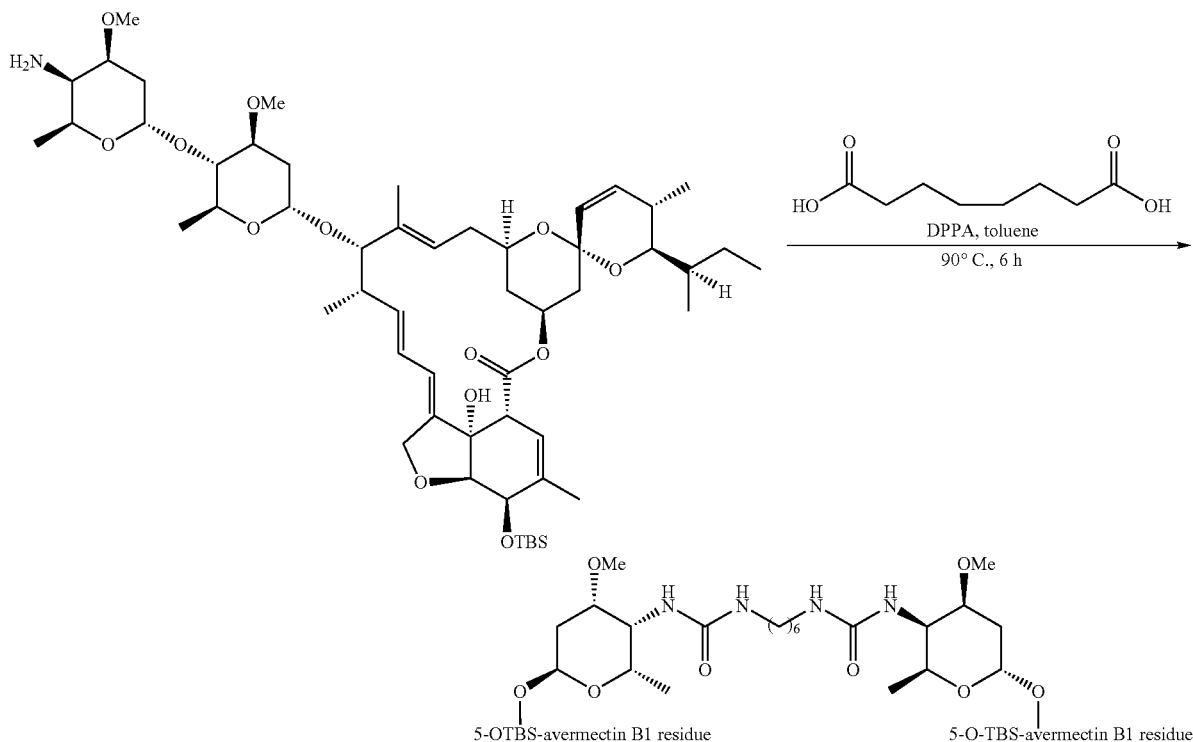

DPPA (380 mg, 1.38 mmol, 3.0 equiv) was added to a solution of 4"-epi-amino-5-O-TBS-4"-desoxy-avermectin B$_1$ (1.0 g, 1.01 mmol, 2.2 equiv), octanedioic acid (80 mg, 0.46 mmol, 1.0 equiv) and triethylamine (140 mg, 1.38 mmol, 3.0 equiv) in toluene (50 mL) under an atmosphere of nitrogen. The resulting solution was stirred for 6 h at 90° C., washed with diluted aqueous HCl (1.0 M, 20 mL). The aqueous layer was extracted with ethyl acetate (20 mL×2) and the organic layers combined and washed with brine (20 mL), dried over anhydrous sodium sulfate, filtered and evaporated to afford 400 mg (41%) of the 5-O-TBS protected dimer compound as a yellow solid, which was used for the next step without further purification.

Step 2

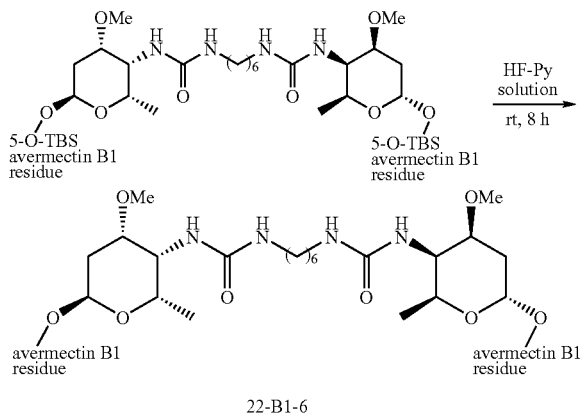

A solution of the 5-O-TBS protected dimer compound from Step 1 (400 mg, 0.19 mmol, 1.0 equiv) in 15 mL of HF-pyridine solution (prepared by diluting 25 g of 70% HF-pyridine solution with 27.5 mL of dry THF, then adding 12.5 mL of pyridine at 0° C. and stirring the suspension for 5 min.) was stirred for 8 h at room temperature. The pH value of the reaction solution was adjusted to 6 with saturated aqueous sodium bicarbonate. The resulting solution was extracted with ethyl acetate (40 mL×3) and the organic layers combined, washed with brine (100 mL), dried over anhydrous sodium sulfate, filtered and evaporated. The residue was purified by column chromatography on silica gel with dichloromethane/methanol (20:1) as eluent to give 70 mg (19%) of 22-B1-6 dimer compound as a light yellow powder. $^1$H NMR (300 MHz, CDCl$_3$) δ 5.87 (br d, J=10.0 Hz, 2H), 5.81 (d, J=1.5 Hz, 2H), 5.80-5.74 (m, 4H), 5.57 (dd, J=10.2, 2.4 Hz, 2H), 5.45 (br s, 2H), 5.43 (d, J=4.0 Hz, 2H), 5.41 (m, 2H), 5.02 (br d, J=7.0 Hz, 2H), 4.79 (d, J=2.8 Hz, 2H), 4.71 (s, 4H), 4.32 (d, J=6.9 Hz, 2H), 3.98 (d, J=6.5 Hz, 2H), 3.95 (s, 2H), 3.93-3.78 (m, 6H), 3.76-3.55 (m, 4H), 3.48 (d, J=10.0 Hz, 2H), 3.45 (s, 6H), 3.43 (s, 6H), 3.31 (d, J=2.0 Hz, 2H), 3.30-3.10 (m, 4H), 3.24 (t, J=9.0 Hz, 2H), 2.53 (m, 2H), 2.34-2.20 (m, 10H), 2.05 (dd, J=12.0, 3.0 Hz, 2H), 1.90 (s, 6H), 1.78 (dd, J=10.5, 2.5 Hz, 2H), 1.70-1.35 (m, 16H), 1.47 (s, 6H), 1.30-1.20 (m, 4H), 1.25 (d, J=6.3 Hz, 6H), 1.19 (d, J=6.5 Hz, 6H), 1.17 (d, J=7.0 Hz, 6H), 0.97 (t, J=7.0 Hz, 6H), 0.95 (d, J=7.0 Hz, 6H), 0.93 (d, J=7.5 Hz, 6H), 0.88 (dd, J=12.5, 6.5 Hz, 2H). LC-MS (electrospray) m/z 1934 (M+Na$^+$).

EXAMPLE 9
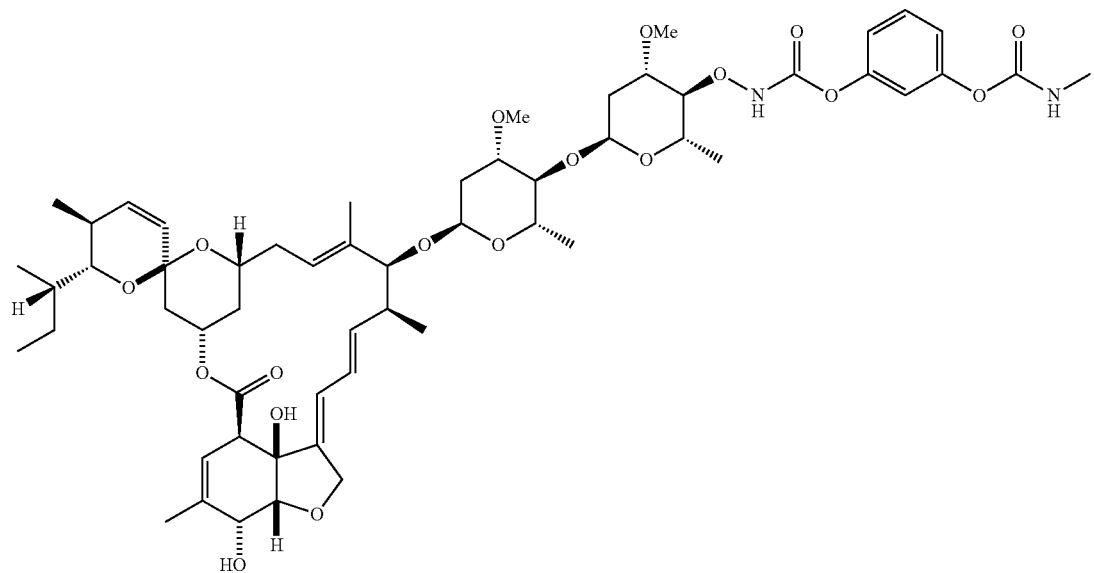
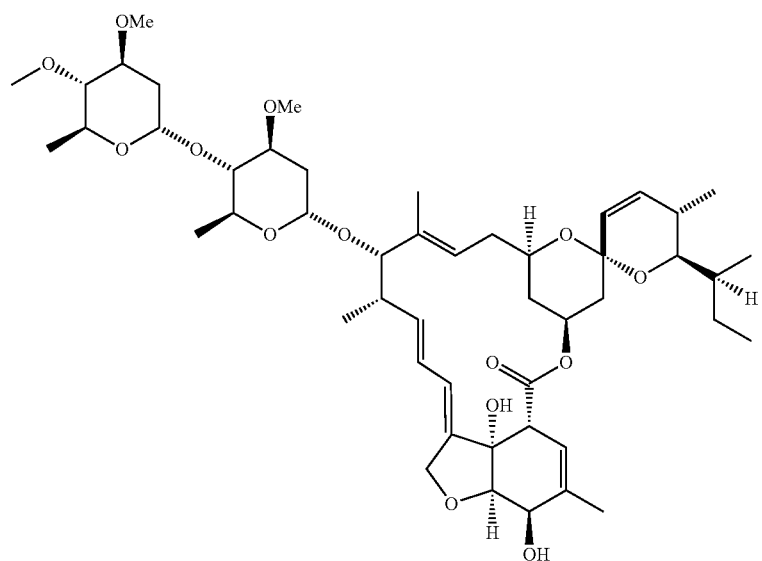
26-B1 (L = phenylene)
Compound 26-B1 shown above with an arylene linker was prepared by reacting a 4"-desozy-4"-aminooxy avermectin B1 with benzene-1,3-dichloroformate.

Step 1: 5-O-TBS-avermectin $B_1$

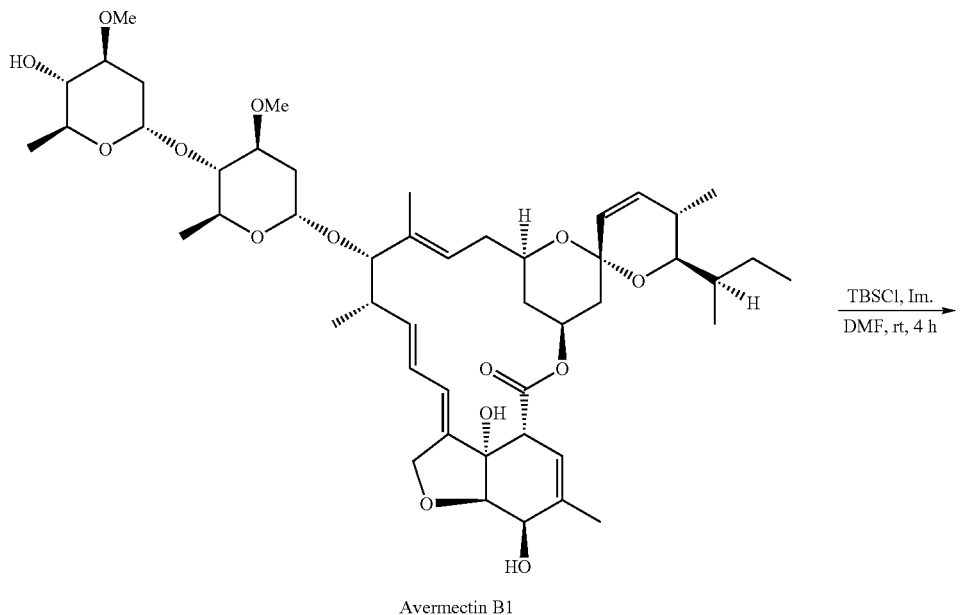

Avermectin B1

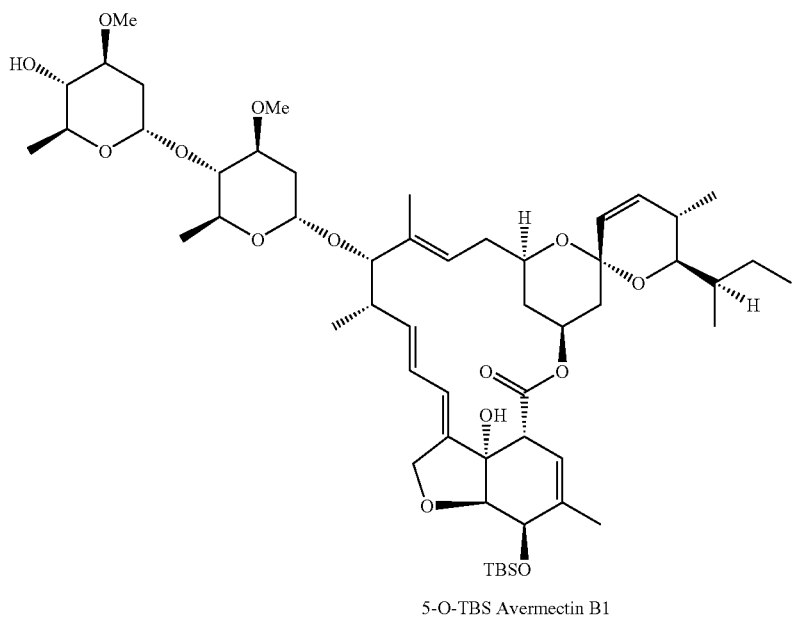

5-O-TBS Avermectin B1

To a solution of avermectin $B_1$ (43.7 g, 50.0 mmol, 1.0 equiv) and imidazole (18.7 g, 275 mmol, 5.5 equiv) in N,N-dimethylformamide (300 mL) was added a solution of tert-butylchlorodimethylsilane (18.9 g, 125 mmol, 2.5 equiv) in N,N-dimethylformamide (50 mL) dropwise at room temperature. The resulting solution was stirred for 4 h at room temperature and then concentrated under vacuum. The residue was chromatographed on a silica gel column with ethyl acetate/petroleum ether (1:10 to 1:2) as eluent to give 33.0 g (67%) of 5-O-TBS-avermectin $B_1$ as a white solid. LC-MS (electrospray) m/z 1009 (M+Na$^+$).

Step 2: 5-O-TBS-4''-oxoavermectin $B_1$

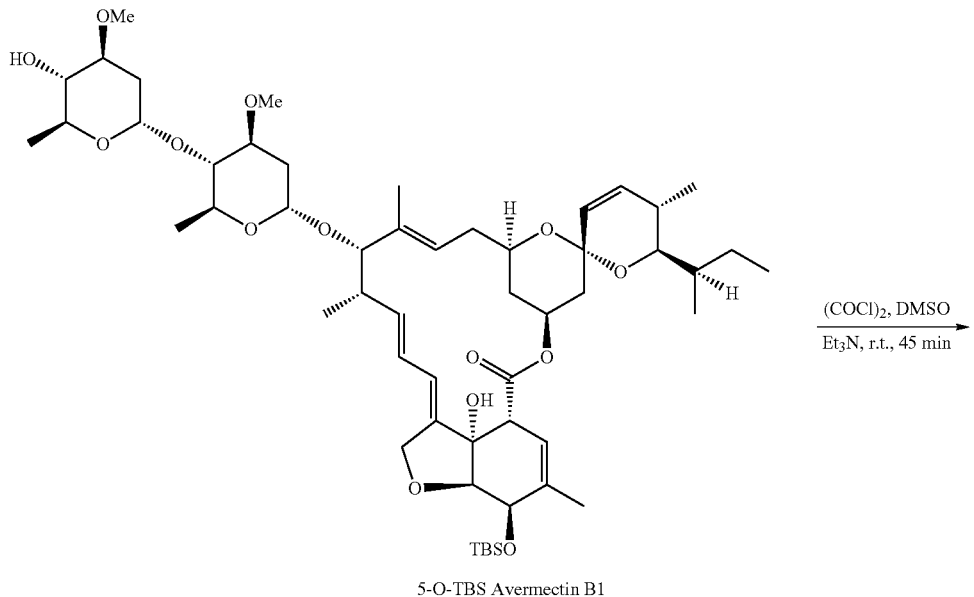

5-O-TBS Avermectin B1

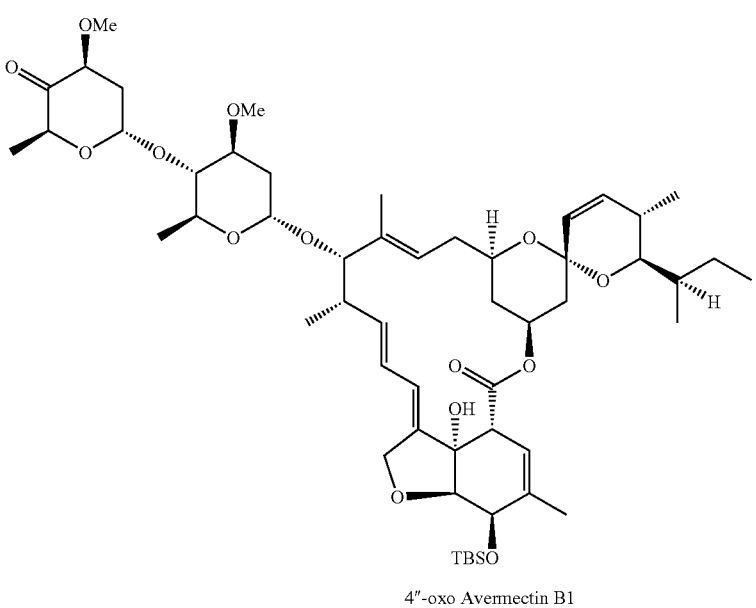

4''-oxo Avermectin B1

Dimethylsulfoxide (2.37 g, 30.36 mmol, 6.0 equiv) was added dropwise to a solution of oxalyl chloride (1.41 g, 11.13 mmol, 2.2 equiv) in dichloromethane (25 mL) at −78° C. under an atmosphere of nitrogen. The reaction mixture was stirred for about 10 min and added a solution of 5-O-TBS-avermectin $B_1$ (5.0 g, 5.06 mmol, 1.0 equiv) in dichloromethane (25 mL) dropwise with stiffing at −78° C. for 30 min, then triethylamine (5.12 g, 50.6 mmol, 10.0 equiv). The resulting solution was stirred for 30 min at −60° C. and allowed to warm to room temperature and stirred for about 45 min. The reaction solution was quenched by the addition of water (50 mL) and separated. The aqueous layer was extracted with dichloromethane (50 mL×2) and the organic layers combined and dried over anhydrous sodium sulfate. Filtration and removal of solvent afforded 4.9 g (98%) of 5-O-TBS-4''-oxoavermectin $B_1$ as a yellow solid. LC-MS (electrospray) m/z 1007 (M+Na+).

Step 3: 5-O-TBS-4''-epi-avermectin B$_1$

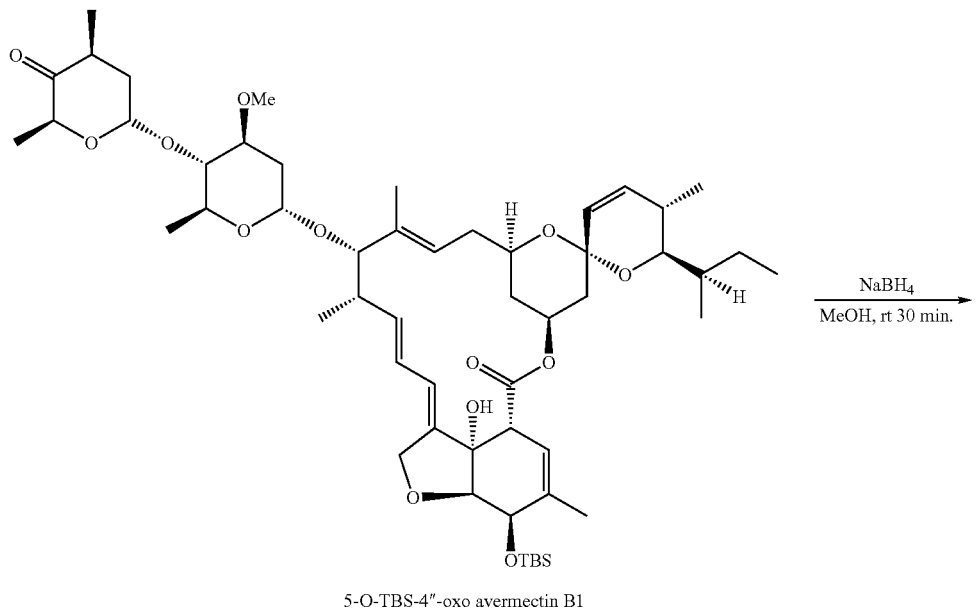

5-O-TBS-4''-oxo avermectin B1

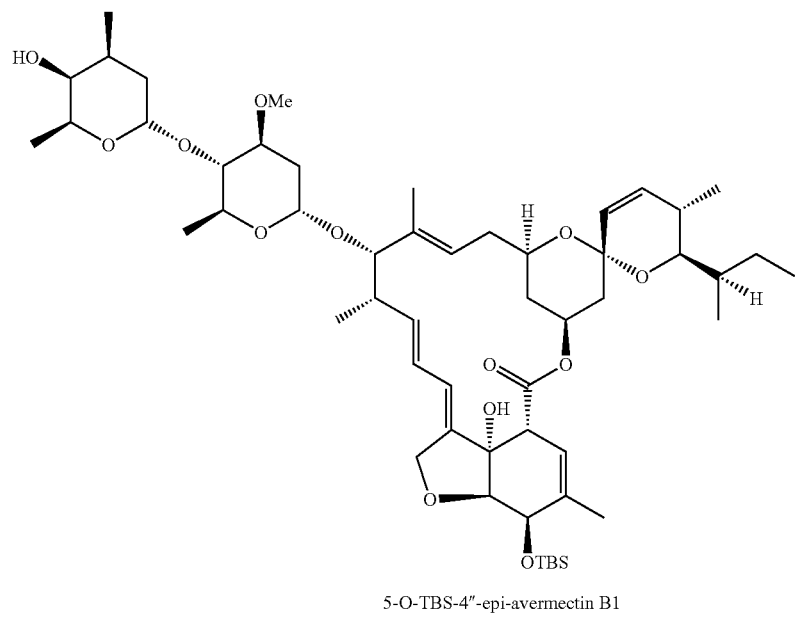

5-O-TBS-4''-epi-avermectin B1

Sodium borohydride (15 mg, 0.40 mmol, 2.0 equiv) was added portionwise to a solution of 5-O-TBS-4''-oxoavermectin B$_1$ (200 mg, 0.20 mmol, 1.0 equiv) in methanol (10 mL). The resulting solution was stirred for 30 min at room temperature, quenched by the addition of water (5 mL), extracted with dichloromethane (30 mL×2) and the organic layers combined and dried over anhydrous sodium sulfate. After filtration and concentration under vacuum, the residue was purified by column chromatography on silica gel with ethyl acetate/petroleum ether (1:10 to 1:3) as eluent to give 120 mg (60%) of 5-O-TBS-4''-epi-avermectin B$_1$ as a yellow solid (the minor by-product 5-O-TBS-4''-avermectin B1 was removed during this stage); LC-MS (electrospray) m/z 1009 (M+Na$^+$).

Step 4: 5-O-TBS-4"-desoxy-avermectin B$_1$-4"-(R)-trifluoromethanesulfonate

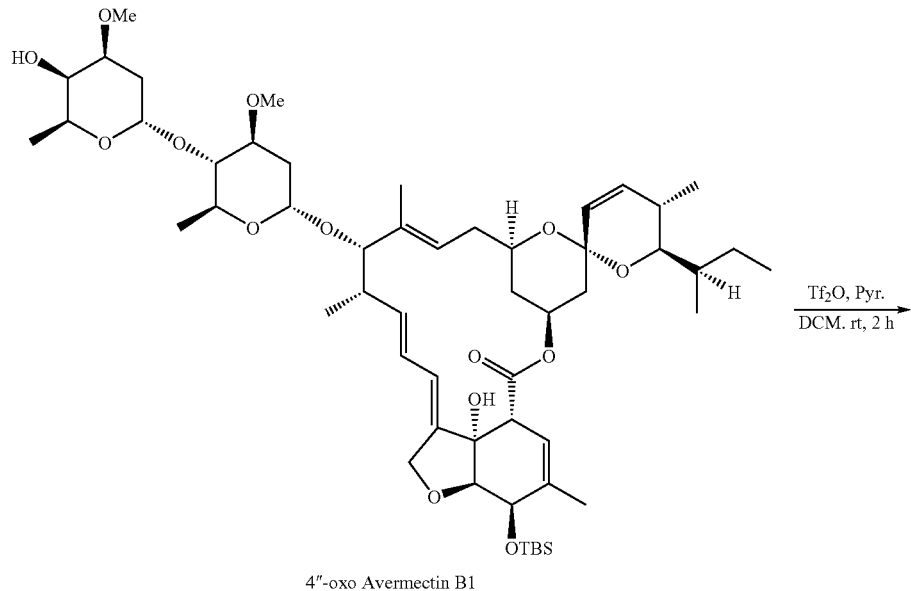

4"-oxo Avermectin B1

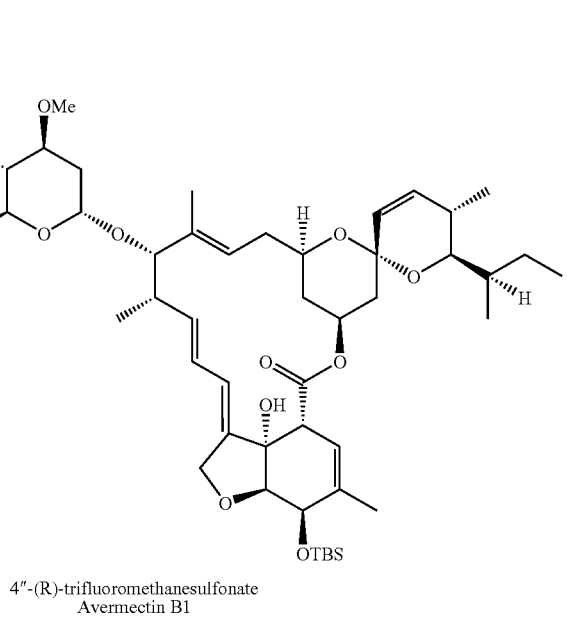

4"-(R)-trifluoromethanesulfonate
Avermectin B1

Trifluoromethanesulfonic anhydride (3.77 g, 13.4 mmol, 4.0 equiv) was added dropwise to a solution of 5-O-TBS-4"-epi-avermectin B$_1$ (3.3 g, 3.34 mmol, 1.0 equiv) and pyridine (2.11 g, 26.7 mmol, 8.0 equiv) in dichloromethane (100 mL) at 0° C. under an atmosphere of nitrogen. The resulting solution was stirred for 2 h at room temperature, diluted with dichloromethane (100 mL), and washed with 10% aqueous HCl (10 mL×2). The organic layers were dried over anhydrous sodium sulfate, filtered, and concentrated under vacuum to give 3.35 g (90%) of 5-O-TBS-4"-desoxy-avermectin B$_1$-4"-(R)-trifluoromethanesulfonate as a brown solid. LC-MS (electrospray) m/z 1141 (M+Na$^+$).

Step 5: 5-O-TBS-4''-desoxy-4''-(S)-phthalimidooxy Avermectin B1

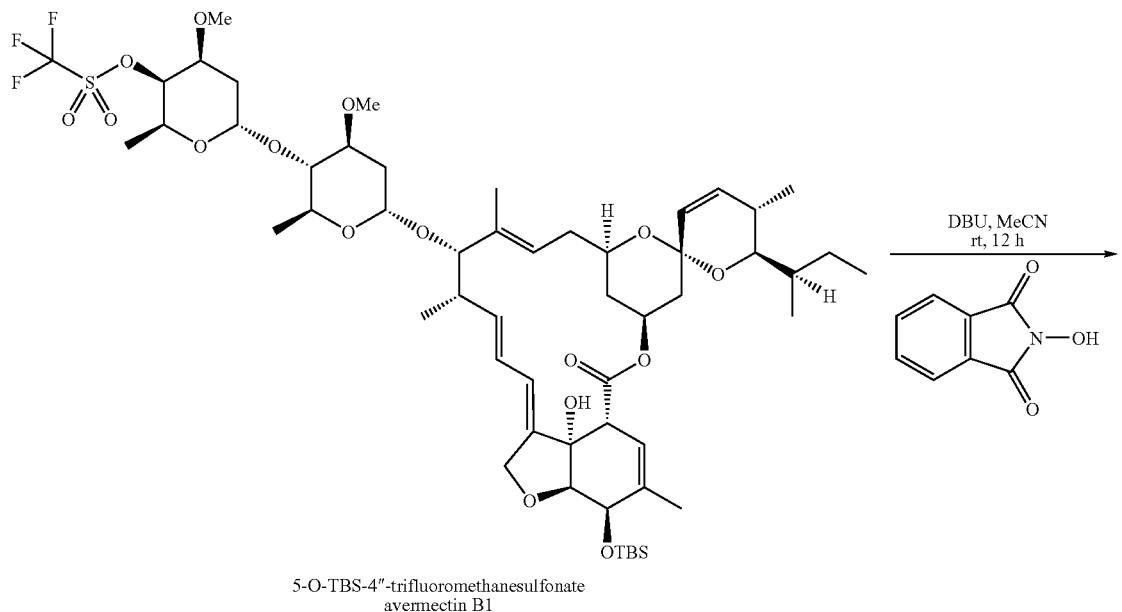

5-O-TBS-4''-trifluoromethanesulfonate avermectin B1

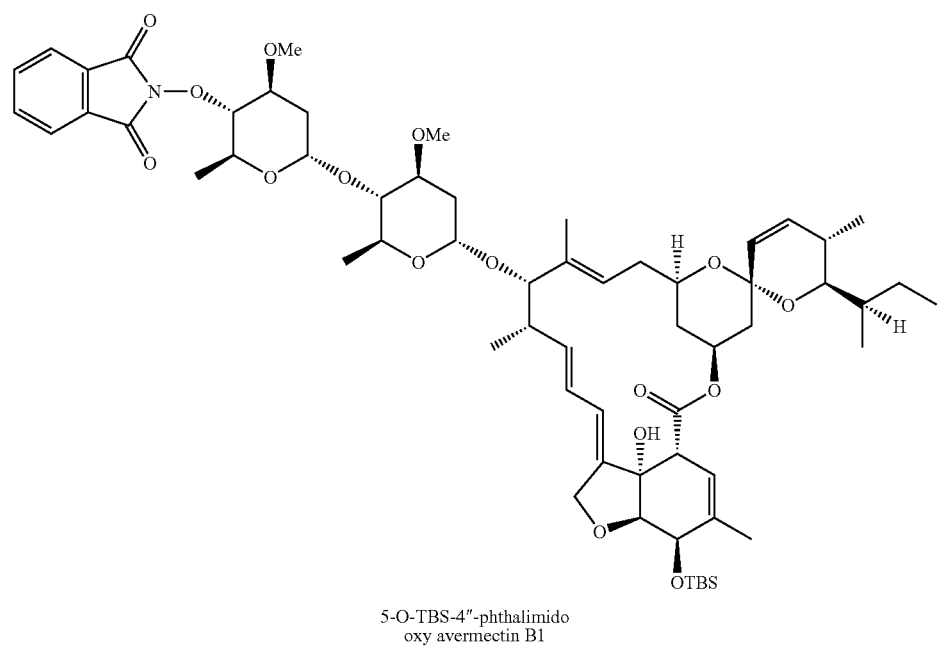

5-O-TBS-4''-phthalimido oxy avermectin B1

A suspension of N-hydroxyphthalimide (2.93 g, 18 mmol, 6.0 equiv) and 1,8-diazabicyclo[5.4.0]undec-7-ene (1.82 g, 12 mmol, 4.0 equiv) in $CH_3CN$ (40 mL) was stirred for 30 min at room temperature and added to a solution of 5-O-TBS-4''-desoxy-avermectin $B_1$-4''-(R)-trifluoromethanesulfonate (3.35 g, 3.0 mmol, 1.0 equiv) in acetonitrile (40 mL) at 0° C. The resulting mixture was stirred for 12 h at room temperature and concentrated under vacuum. The residue was purified by column chromatography on silica gel with ethyl acetate/petroleum ether (1:15 to 1:5) as eluent to give 1.7 g (50%) of 5-O-TBS-4''-desoxy-4''-(S)-phthalimidooxy-avermectin $B_1$ as a bright yellow solid. LC-MS (electrospray) m/z 1154 (M+Na$^+$).

Step 6: 4"-desoxy-4"-(S)-phthalimidooxy-avermectin $B_1$

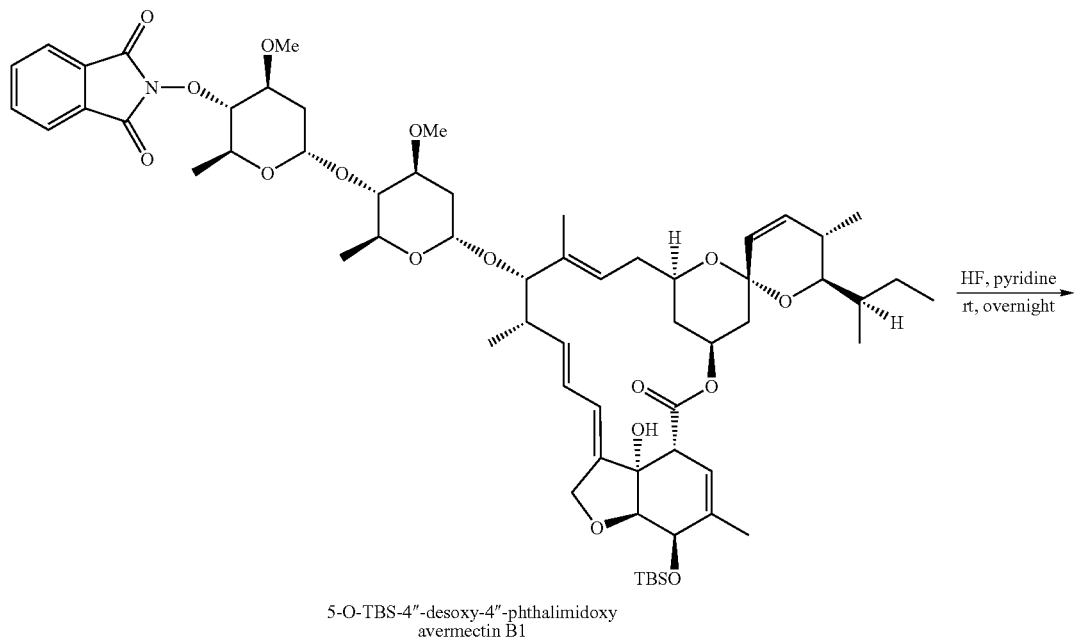

5-O-TBS-4"-desoxy-4"-phthalimidoxy avermectin B1

4"-desoxy-4"-(S)-phthalimidoxy avermectin B1

5-O-TBS-4"-desoxy-4"-(S)-phthalimidooxy-avermectin $B_1$ (400 mg, 0.35 mmol, 1.0 equiv) was dissolved in HF-Pyridine solution (15 mL, prepared by diluting 25 g of 70% HF-pyridine solution with 27.5 mL of dry tetrahydrofuran, then adding 12.5 mL of pyridine at 0° C. and stiffing the suspension for 5 min.). The resulting solution was stirred overnight at ambient temperature, diluted with water (20 mL), extracted with ethyl acetate (50 mL×3) and the organic layers combined, washed with saturated aqueous sodium bicarbonate (100 mL), dried over anhydrous sodium sulfate. After filtration and removal of solvent, the residue was purified by column chromatography on silica gel with ethyl acetate/petroleum ether (1:5 to 1:2) as eluent to give 172 mg (48%) of 4"-desoxy-4"-(S)-phthalimidooxy-avermectin $B_1$ as a white powder. LC-MS (electrospray) m/z 1040 (M+Na$^+$).

Step 7 4"-desoxy-4"-(S)-aminooxy-avermectin B₁

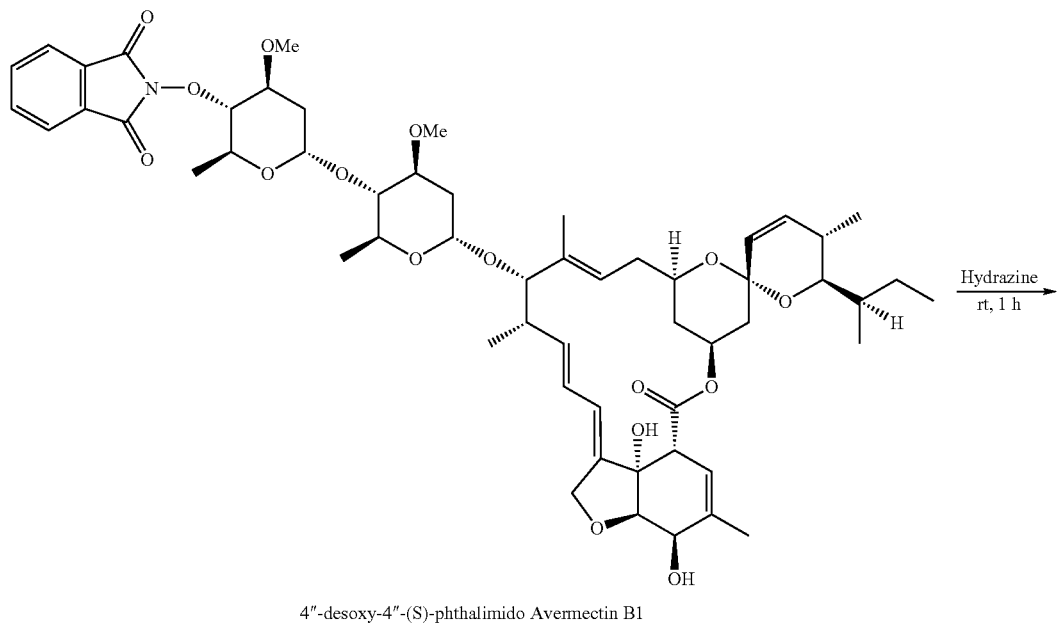

4"-desoxy-4"-(S)-phthalimido Avermectin B1

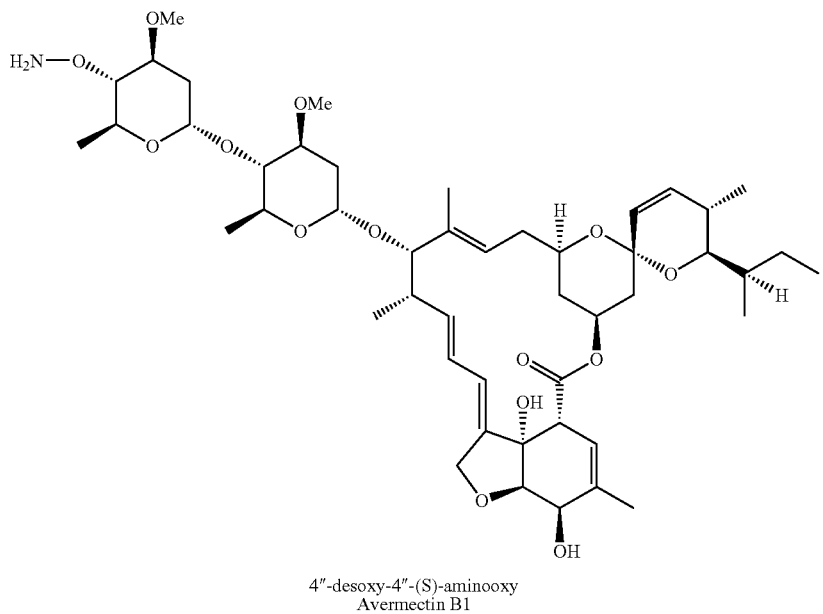

4"-desoxy-4"-(S)-aminooxy Avermectin B1

Hydrazine monohydrate (8.1 mg, 0.15 mmol, 1.5 equiv) was added to a solution of 4"-desoxy-4"-(S)-phthalimidooxy-avermectin B₁ (86 mg, 0.10 mmol, 1.0 equiv) in ethanol (5 mL). The resulting solution was stirred for 1 h at ambient temperature, diluted with water (10 mL) and extracted with ethyl acetate (20 mL×3) and the organic layers combined, washed with water (20 mL) and saturated aqueous sodium bicarbonate (20 mL), and dried over anhydrous sodium sulfate. After filtration and removal of solvent, the residue was recrystallized from dichloromethane/hexane (10:1) to give 60 mg (68%) of 4"-desoxy-4"-(S)-aminooxy-avermectin B₁ as a white powder. LC-MS (electrospray) m/z 910 (M+Na⁺).

Step 8: Compound 26-B1

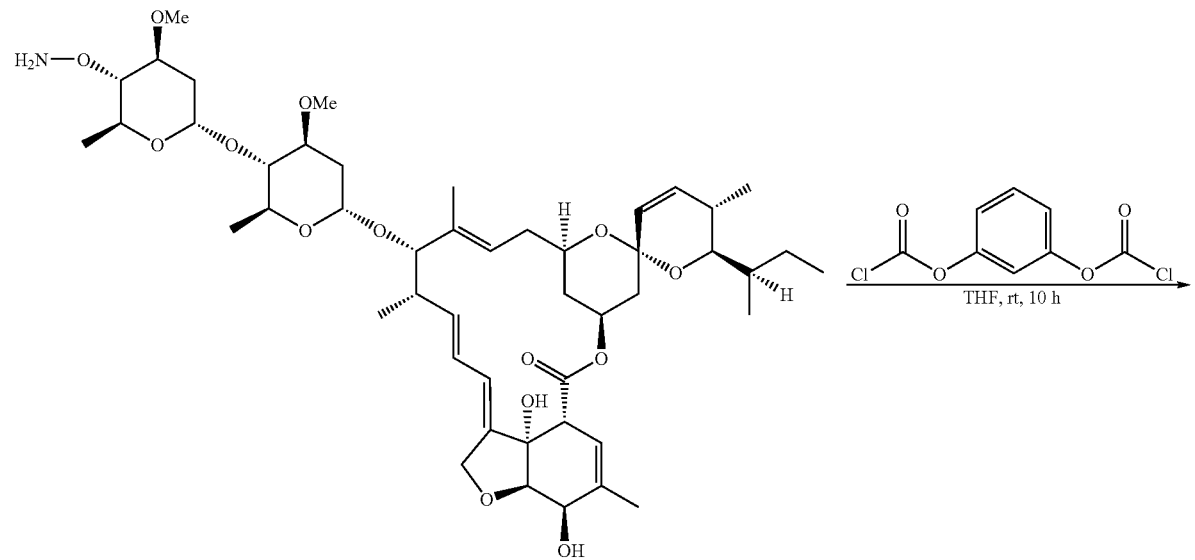

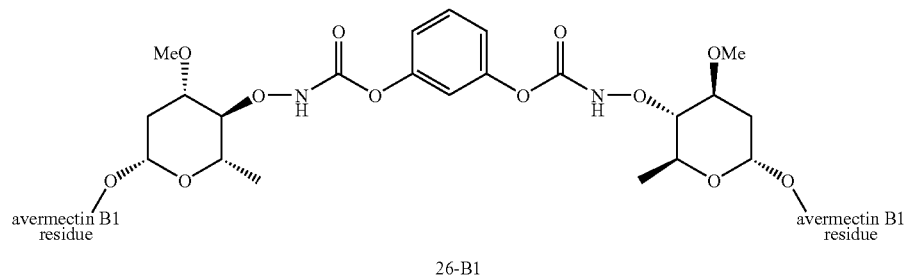

26-B1

Benzene-1,3-dichloroformate (2.4 mg, 0.01 mmol, 1.0 equiv) was added to a solution of 4"-desoxy-4"-(S)-aminooxy-avermectin $B_1$ (26.6 mg, 0.03 mmol, 3.0 equiv) in anhydrous tetrahydrofuran (2 mL) at 0° C. in a 10-mL tube. The resulting solution was stirred for 10 h at room temperature and concentrated under vacuum. The residue was purified by column chromatography on silica gel with methanol/dichloromethane (1:60 to 1:50) as eluent to give 14.3 mg (74%) of 26-B1 as a white powder. $^1$H NMR (300 MHz, DMSO) δ 10.96 (br s, 2H), 7.96 (s, 2H), 7.43 (m, 1H), 7.03 (m, 2H), 6.94 (m, 1H), 5.87 (br d, J=10.0 Hz, 2H), 5.78 (d, J=2.0 Hz, 2H), 5.77-5.50 (m, 4H), 5.36 (d, J=2.4 Hz, 2H), 5.27 (br s, 2H), 5.23 (d, J=4.0 Hz, 2H), 5.13 (m, 2H), 4.83 (br d, J=7.0 Hz, 2H), 4.72 (d, J=3.0 Hz, 2H), 4.69 (s, 2H), 4.57 (d, J=12.0 Hz, 2H), 4.43 (d, J=12.0 Hz, 2H), 3.91 (d, J=6.5 Hz, 2H), 3.79 (s, 2H), 3.85-3.63 (m, 6H), 3.62-3.50 (m, 4H), 3.41 (s, 2H), 3.39 (s, 6H), 3.30 (s, 6H), 3.17 (t, J=9.0 Hz, 2H), 3.05 (d, J=2.0 Hz, 2H), 2.88 (s, 4H), 2.74 (s, 4H), 2.58 (m, 2H), 2.32-2.07 (m, 10H), 2.02 (dd, J=12.0, 3.0 Hz, 2H), 1.71 (s, 6H), 1.58 (dd, J=10.5, 2.5 Hz, 2H), 1.65-1.40 (m, 8H), 1.48 (s, 6H), 1.29 (d, J=6.5 Hz, 6H), 1.16 (d, J=6.5 Hz, 6H), 1.08 (d, J=7.0 Hz, 6H), 0.95 (t, J=7.0 Hz, 6H), 0.93 (d, J=7.0 Hz, 6H), 0.89 (d, J=7.5 Hz, 6H), 0.80 (dd, J=12.5, 6.5 Hz, 2H). LC-MS (electrospray) m/z 1960 (M+Na$^+$).

EXAMPLE 10
An avermectin B1 dimer shown below wherein L is a $C_6$ alkylene linker and $R_9$ and $R_{10}$ are each —ONHC(=O)NH— was prepared by reacting 4"-aminooxy Avermectin B1 with a bis-isocyanate reagent.
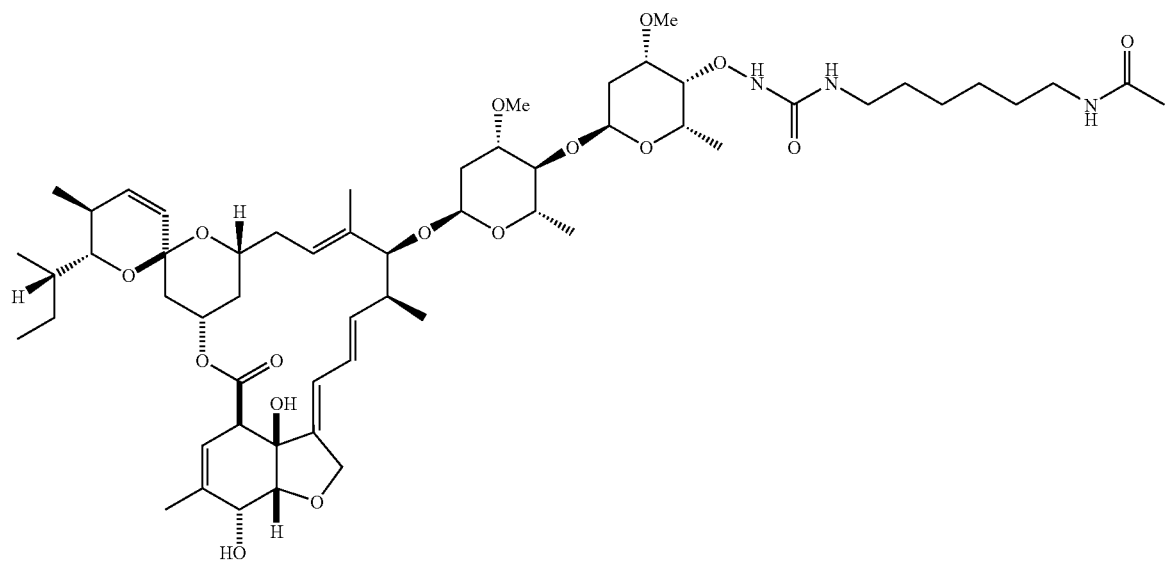
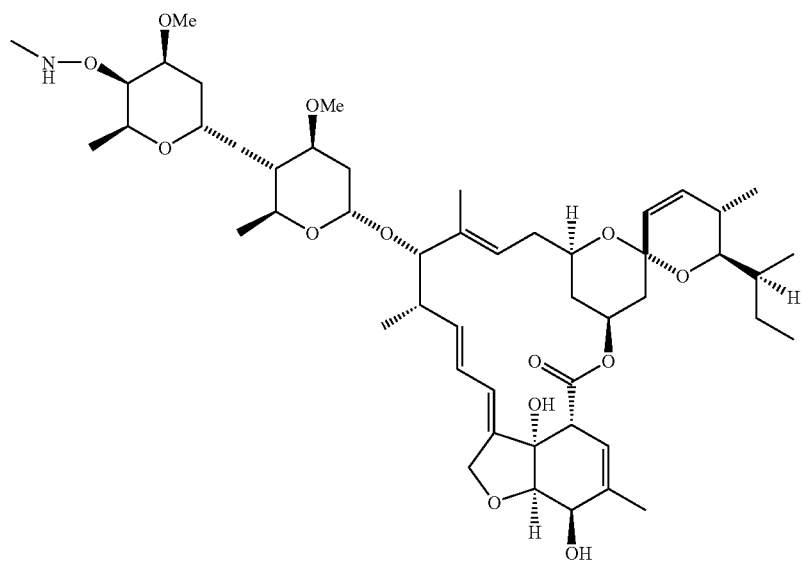

Step 1: 5-O-TBS-avermectin $B_1$

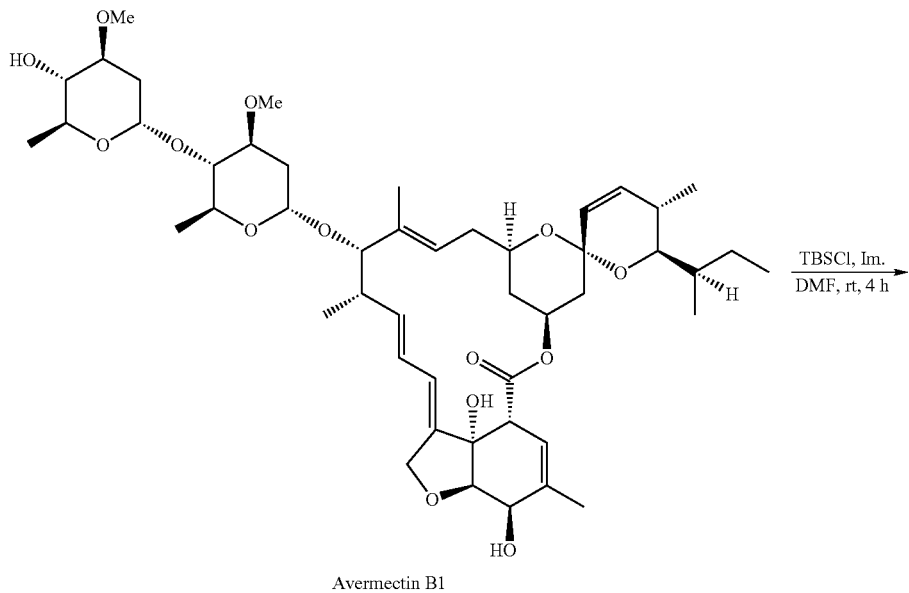

Avermectin B1

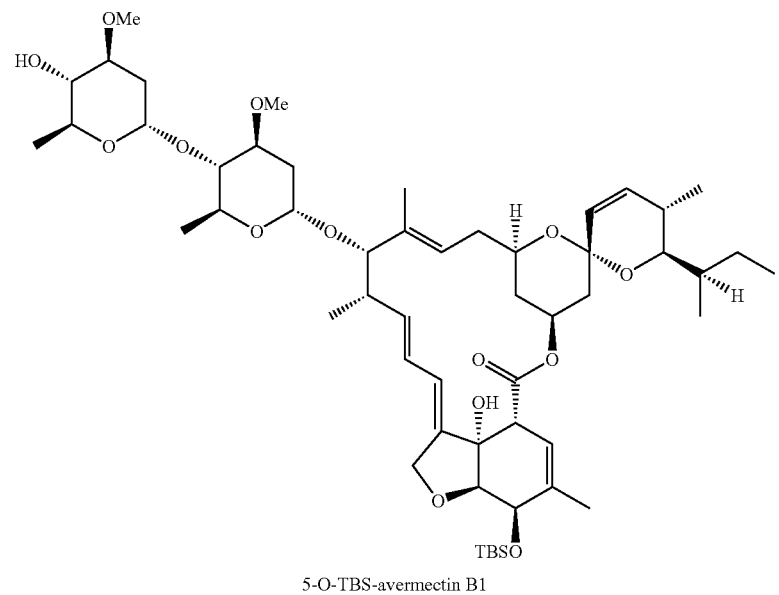

5-O-TBS-avermectin B1

To a solution of avermectin $B_1$ (43.7 g, 50.0 mmol, 1.0 equiv) and imidazole (18.7 g, 275 mmol, 5.5 equiv) in N,N-dimethylformamide (300 mL) was added a solution of tert-butylchlorodimethylsilane (18.9 g, 125 mmol, 2.5 equiv) in N,N-dimethylformamide (50 mL) dropwise at room temperature. The resulting solution was stirred for 4 h at room temperature and then concentrated under vacuum. The residue was chromatographed on a silica gel column with ethyl acetate/petroleum ether (1:10 to 1:2) as eluent to give 33.0 g (67%) of 5-O-TBS-avermectin $B_1$ as a white solid. LC-MS (electrospray) m/z 1009 (M+Na$^+$).

Step 2: 5-O-TBS-4"-desoxy-avermectin $B_1$-4"-(S)-trifluoromethanesulfonate

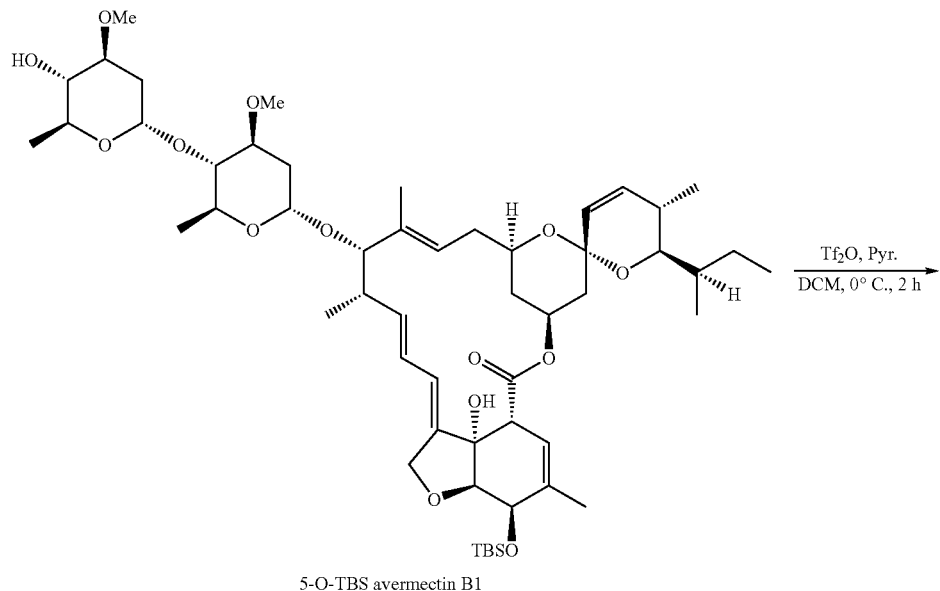

5-O-TBS avermectin B1

5-O-TBS-4"-trifluoromethanesulfonate avermectin B1

Trifluoromethanesulfonic anhydride (5.72 g, 20.28 mmol, 2.0 equiv) was added dropwise to a solution of 5-O-TBS-avermectin $B_1$ (10 g, 10.13 mmol, 1.0 equiv) and pyridine (3.2 g, 40.51 mmol, 4.0 equiv) in dichloromethane (150 mL) at 0° C. under an atmosphere of nitrogen. The resulting solution was stirred for 2 h at 0° C. in an ice/salt bath, diluted with dichloromethane (100 mL), and washed with 10% aqueous HCl (100 mL×2) and brine (100 mL). The organic layers were dried over anhydrous sodium sulfate, filtered, and concentrated under vacuum. The residue was purified by column chromatography on silica gel with petroleum ether/dichloromethane/ethyl acetate (10:2:1) as eluent to give 10 g (88%) of 5-O-TBS-4"-desoxy-avermectin $B_1$-4"-(S)-trifluoromethanesulfonate as a yellow solid. LC-MS (electrospray) m/z 1141 (M+Na$^+$).

Step 3: 5-O-TBS-4"-desoxy-4"-(R)-phthalimidooxy-avermectin $B_1$

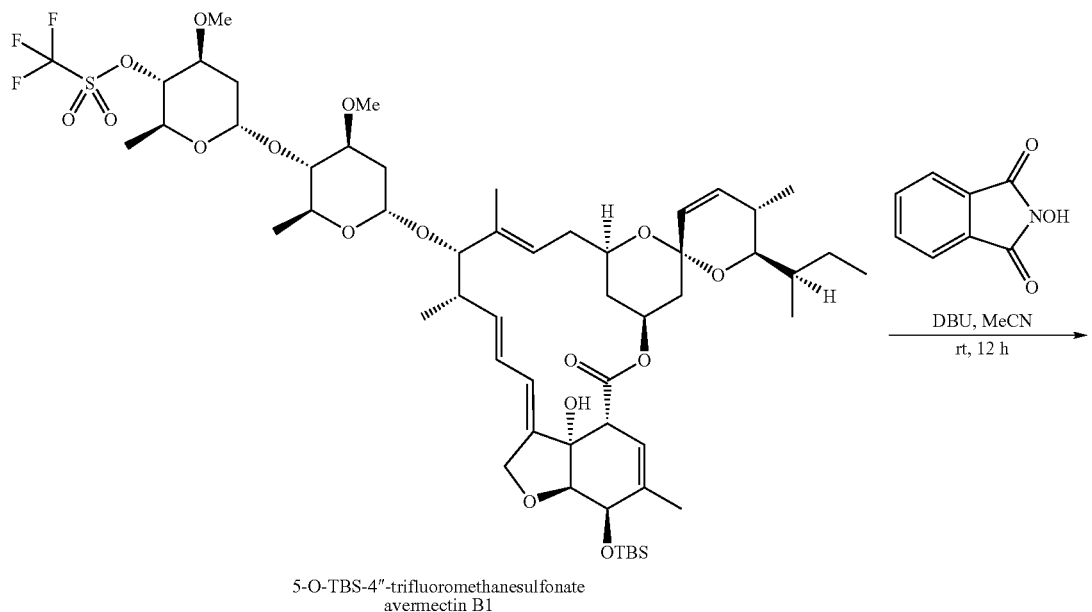

5-O-TBS-4"-trifluoromethanesulfonate avermectin B1

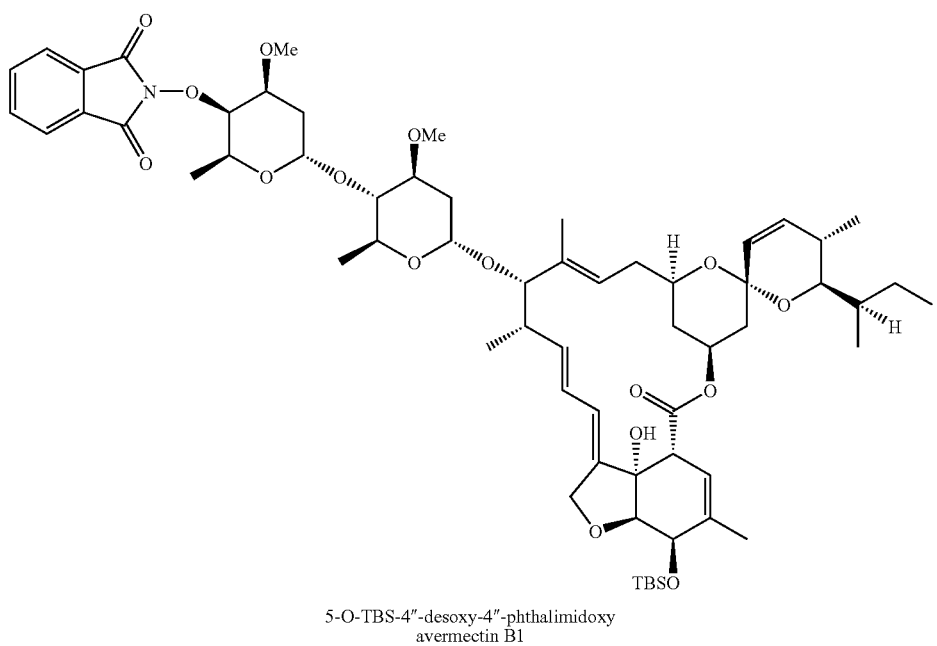

5-O-TBS-4"-desoxy-4"-phthalimidoxy avermectin B1

A suspension of N-hydroxyphthalimide (8.63 g, 52.90 mmol, 6.0 equiv) and 1,8-diazabicyclo[5.4.0]undec-7-ene (5.36 g, 35.21 mmol, 4.0 equiv) in acetonitrile (100 mL) was stirred for 30 min at room temperature and added to a solution of 5-O-TBS-4"-desoxy-avermectin $B_1$-4"-(S)-trifluoromethanesulfonate (9.87 g, 8.82 mmol, 1.0 equiv) in acetonitrile (100 mL) at 0° C. The resulting mixture was stirred for 12 h at room temperature, concentrated under vacuum, diluted with dichloromethane (100 mL), and washed with saturated aqueous ammonium chloride (100 mL×2). The combined organic layers were washed with brine (100 mL×2) and dried over sodium sulfate. After filtration and removal of solvent, the residue was purified by column chromatography on silica gel with ethyl acetate/petroleum ether (1:8) as eluent to give 4.0 g (40%) of 5-O-TBS-4"-desoxy-4"-(R)-phthalimidooxy-avermectin $B_1$ as a light yellow solid. LC-MS (electrospray) m/z 1154 (M+Na⁺).

Step 4: 5-O-TBS-4"-desoxy-4"-(R)-aminooxy-avermectin B$_1$

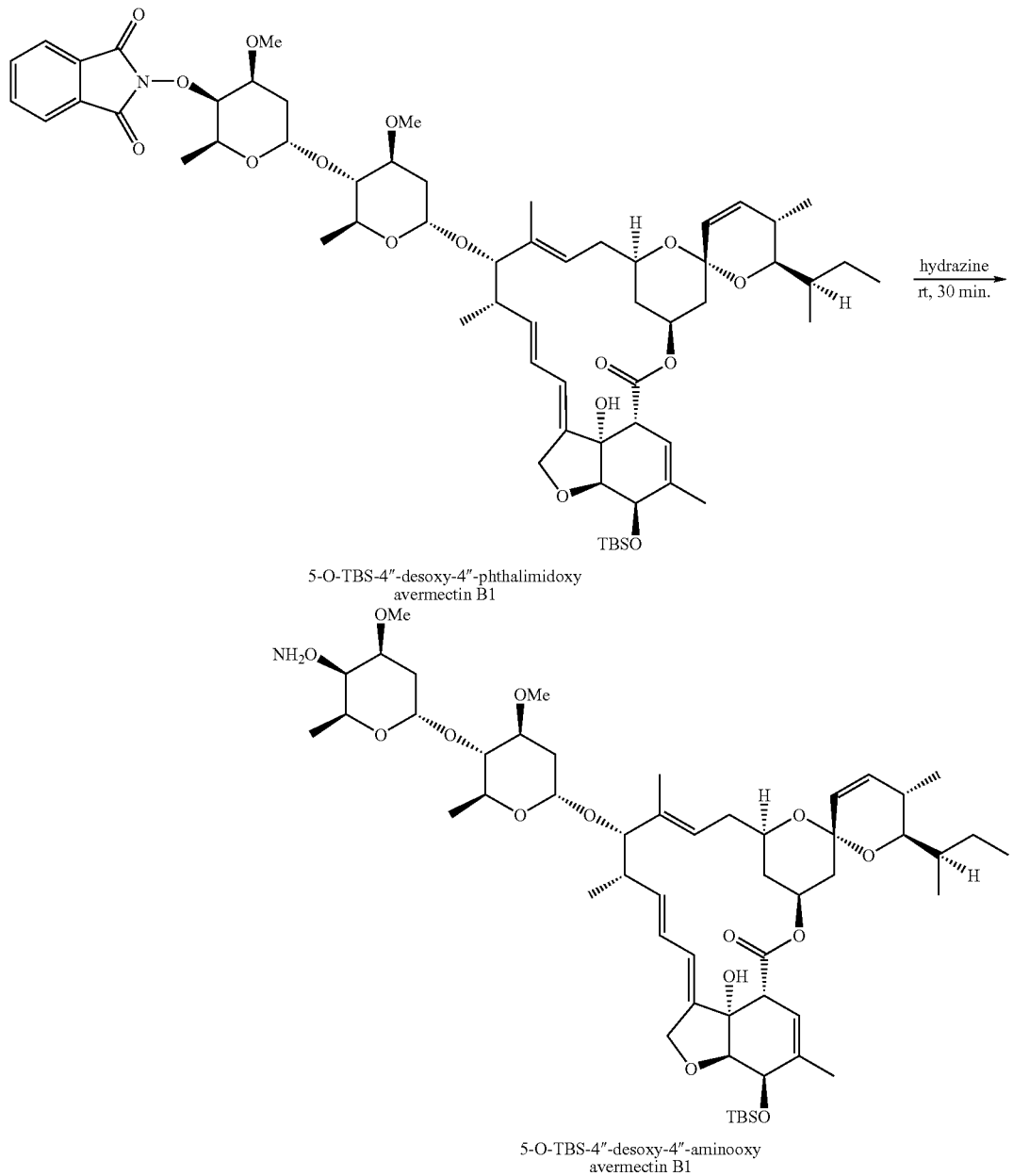

5-O-TBS-4"-desoxy-4"-phthalimidoxy avermectin B1

5-O-TBS-4"-desoxy-4"-aminooxy avermectin B1

Hydrazine monohydrate (18 mg, 0.33 mmol, 1.5 equiv) was added to a solution of 5-O-TBS-4"-desoxy-4"-(R)-phthalimidooxy-avermectin B$_1$ (250 mg, 0.22 mmol, 1.0 equiv) in ethanol (15 mL). The resulting solution was stirred for 30 min at ambient temperature, diluted with water (20 mL) and extracted with ethyl acetate (50 mL×3) and the organic layers combined, washed with water (50 mL) and saturated aqueous sodium bicarbonate (50 mL), and dried over anhydrous sodium sulfate. After filtration and removal of solvent, the residue was purified by column chromatography on silica gel with ethyl acetate/petroleum ether (1:5 to 1:2) as eluent to give 0.16 g (73%) of 5-O-TBS-4"-desoxy-4"-(R)-aminooxy-avermectin B$_1$ as a light yellow solid. LC-MS (electrospray) m/z 1025 (M+Na$^+$).

Step 5: 1,6-diisocyanatohexane

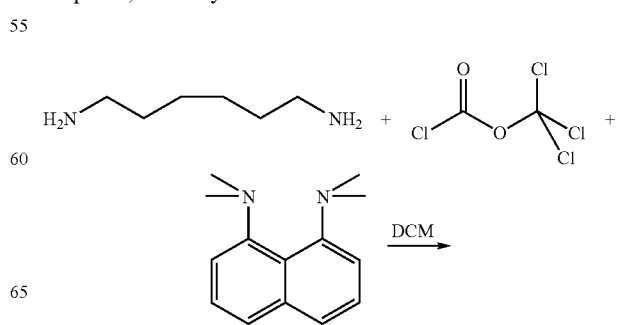

-continued

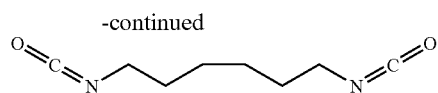

Diphosgene (238 mg, 1.2 mmol, 1.2 equiv) was added dropwise to a solution of hexane-1,6-diamine (116 mg, 1.0 mmol, 1.0 equiv) and $N^1,N^1,N^8,N^8$-tetramethylnaphthalene-1,8-diamine (857 mg, 4.0 mmol, 4.0 equiv) in dichloromethane (10 mL) at 0° C. under an inert atmosphere of nitrogen. The resulting solution was stirred for 10 min at 0° C., diluted with dichloromethane (20 mL), washed with 1 M aqueous HCl (10 mL×3) and 1 M aqueous sodium hydroxide (10 mL). The organic layer was washed with brine (20 mL), separated, dried over anhydrous sodium sulfate, filtered and concentrated under vacuum to give 101 mg (60%) of 1,6-diisocyanatohexane as a bright yellow oil.

Step 6: 5-O-TBS-30-B1-6

To a solution of 5-O-TBS-4″-desoxy-4″-(R)-aminooxy-avermectin $B_1$ (105 mg, 0.105 mmol, 2.1 equiv) and triethylamine (15.2 mg, 0.15 mmol, 3.0 equiv) in dichloromethane (5 mL) was added 1,6-diisocyanatohexane (8.4 mg, 0.05 mmol, 1.0 equiv) at room temperature under an atmosphere of nitrogen. The resulting solution was stirred for 12 h, diluted with dichloromethane (20 mL), washed with 1 M aqueous HCl (10 mL×3) and 1 M aqueous sodium hydroxide (10 mL). The organic layer was washed with brine (10 mL), separated, dried over anhydrous sodium sulfate, filtered and concentrated under vacuum. The residue was purified by column chromatography on silica gel with dichloromethane/methanol (150:1 to 50:1) as eluent to give 50 mg (46%) of 5-O-TBS-30-B1-6 as a bright yellow solid.

Step 7: 30-B1-6

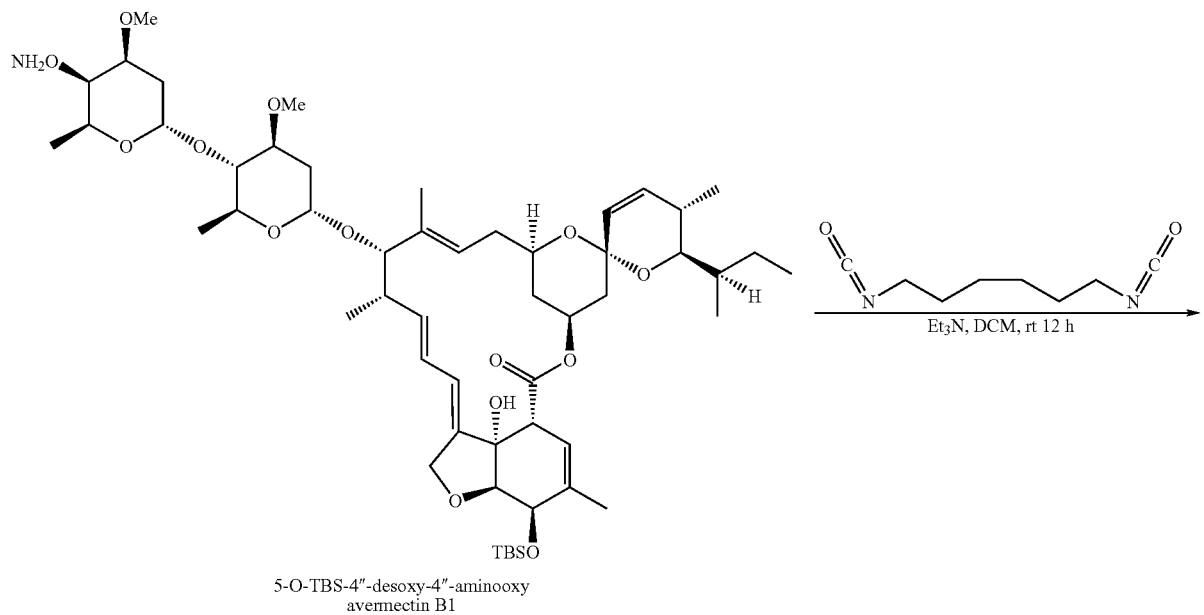

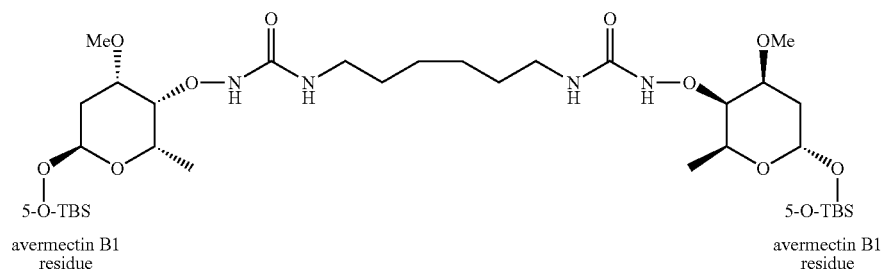

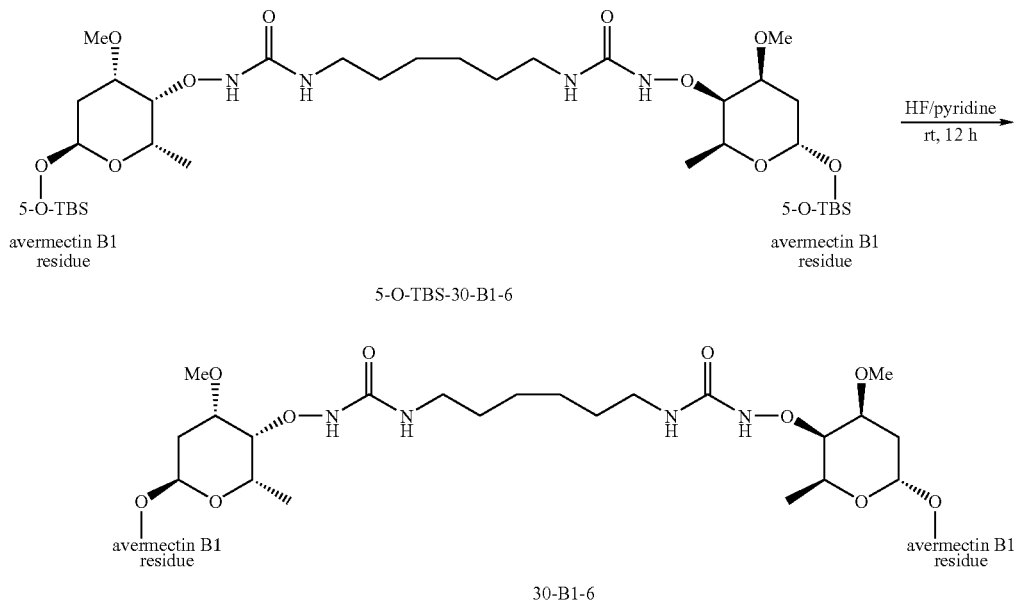

5-O-TBS-30-B1-6

30-B1-6

A solution of 5-O-TBS-30-B1-6 (50 mg, 0.023 mmol, 1.0 equiv) in 2 mL of HF-pyridine solution (prepared by diluting 25 g of 70% HF-pyridine solution with 27.5 mL of dry THF, then adding 12.5 mL of pyridine at 0° C. and stiffing the suspension for 5 min.) was stirred for 12 h at room temperature. The pH value of the reaction solution was adjusted to 6 with saturated aqueous sodium bicarbonate. The resulting solution was extracted with ethyl acetate (15 mL×2) and the organic layers combined, washed with brine (20 mL), dried over anhydrous sodium sulfate, filtered and concentrated under vacuum. The residue was purified by column chromatography on silica gel with dichloromethane/methanol (20:1) as eluent to give 30 mg (67%) of 30-B1-6 as a light yellow solid. $^1$H NMR (300 MHz, CDCl$_3$) δ 5.88 (br d, J=10.0 Hz, 2H), 5.81 (d, J=1.5 Hz, 2H), 5.80-5.72 (m, 4H), 5.59 (dd, J=10.0, 2.4 Hz, 2H), 5.45 (br s, 2H), 5.44-5.32 (m, 4H), 5.01 (br d, J=7.0 Hz, 2H), 4.79 (d, J=2.8 Hz, 2H), 4.70 (s, 4H), 4.32 (d, J=6.9 Hz, 2H), 3.99 (d, J=6.5 Hz, 2H), 3.95 (s, 2H), 3.94-3.79 (m, 6H), 3.60-3.52 (m, 4H), 3.48 (d, J=10.0 Hz, 2H), 3.47 (s, 6H), 3.36 (s, 6H), 3.31 (d, J=2.0 Hz, 2H), 3.30-3.14 (m, 4H), 3.18 (t, J=9.0 Hz, 2H), 2.54 (m, 2H), 2.32-2.15 (m, 10H), 2.05 (dd, J=12.0, 3.0 Hz, 2H), 1.90 (s, 6H), 1.81 (dd, J=10.5, 2.5 Hz, 2H), 1.75-1.40 (m, 16H), 1.52 (s, 6H), 1.40-1.20 (m, 4H), 1.28 (d, J=6.5 Hz, 6H), 1.19 (d, J=6.5 Hz, 6H), 1.17 (d, J=7.0 Hz, 6H), 0.99 (t, J=7.0 Hz, 6H), 0.95 (d, J=7.0 Hz, 6H), 0.93 (d, J=7.5 Hz, 6H), 0.88 (dd, J=12.5, 6.5 Hz, 2H). LC-MS (electrospray) m/z 1966 (M+Na$^+$).

Biological Activity Against Animal Parasites
Activity Against *Caenorhabditis Elegans*

Compounds formulated in 100% DMSO are tested in microtiter plates containing 50 µl nematode growth media, 1% *E. coli* and 20 L1 *C. elegans*. The efficacy of a compound is determined based on the motility of the larvae as compared to average motility of control wells containing DMSO only. A dose response assay is conducted with compounds with >80% reduction in motility in the primary assay to determine an EC$_{50}$ value. Compounds 21-B1-4, 22-B1-5, 22-B1-6, 27-B1, 28-B1-4, 29-B1-6, 30-B1-6 and 33-B1-4 were measured to have an EC$_{50}$ values of less than 0.5 ppm in this assay.

Activity Against *Haemonchus Contortus*

Compounds formulated in 100% DMSO are tested in microtiter plates containing 50 µl nematode media, 7% fecal slurry and 20 L1 *H. contortus*. The efficacy of a compound is determined based on the motility of the larvae as compared to average motility of control wells containing DMSO only. An MIC90 value is calculated by determining the lowest dose at which there was a 90% reduction in motility as compared to the control wells. Compounds 21-B1-4, 22-B1-5, 22-B1-6, 27-B1, 28-B1-4, 29-B1-6, 30-B1-6, 31-B1-4, 32-B1-4 and 33-B1-4 were measured to have an MIC$_{90}$ values of less than 0.5 ppm in this assay.

Activity Against *Aedes Aegypti*

Compounds formulated in 100% DMSO are tested in microtiter plates containing 180 ul 1× Luria Broth media and 10 neonate *A. aegypti* larvae. The efficacy of a compound is determined based on the motility of the larvae as compared to average motility of control wells containing DMSO only. A dose response assay is conducted with compounds with >80% reduction in motility in the primary assay to determine an EC$_{50}$ value. Selected compounds are advanced to insecticide secondary assays. In this assay, compounds 21-B1-4, 27-B1, 28-B1-4, 29-B1-6 and 33-B1-4 were found to have EC$_{50}$ values of less than 1 ppm The invention is further described by the following numbered paragraphs:

1. A compound of formula (I) or a pharmaceutically acceptable salt thereof:

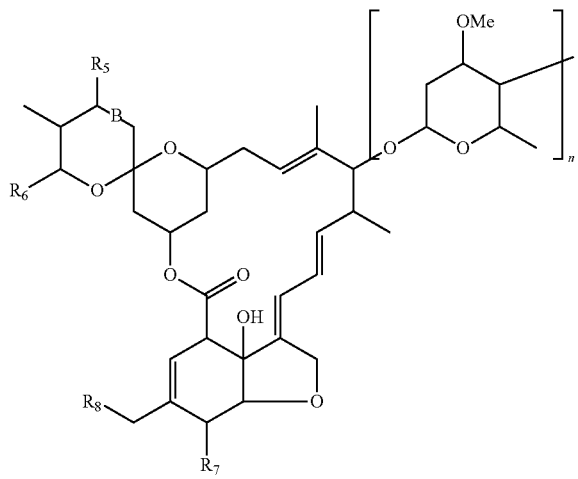
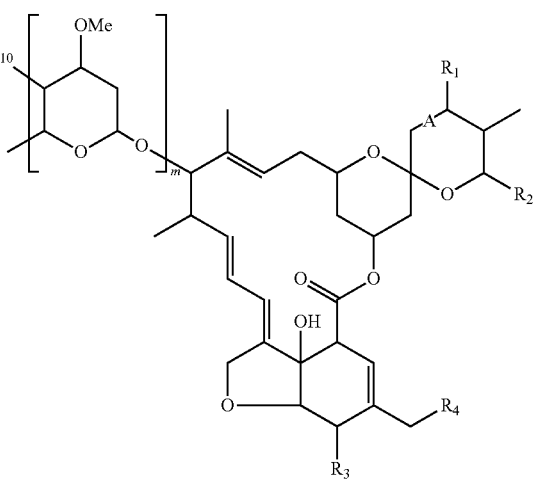

wherein:
A is a single or double bond;
B is a single or double bond;
$R_1$ and $R_5$ are independently hydrogen, hydroxyl, oxo, oximino or alkoxyimino, provided that $R_1$ is hydroxyl only when A is a single bond, and that $R_5$ is hydroxyl only when B is a single bond;
$R_2$ and $R_6$ are independently linear or branched $C_1$-$C_8$ alkyl, $C_2$-$C_8$ alkenyl, or $C_3$-$C_8$ cycloalkyl;
$R_3$ and $R_7$ are independently hydroxyl, methoxy, oxo, hydroximino, or alkoxyimino;
$R_4$ and $R_8$ are independently hydrogen, hydroxyl, $C_1$-$C_8$ alkanoyloxy, benzoyloxy, di-$C_1$-$C_8$ alkylamino benzoyloxy, $(C_1$-$C_8$ alkoxy$)_p$, $C_1$-$C_8$ alkylthio, $C_1$-$C_8$ alkylthioalkoxy or oleandrosyloxy;
$R_9$ and $R_{10}$ are independently diradical groups selected from a bond, O, $NR_{11}$, —$NR_{11}C(=O)$—, —$NR_{11}C(=S)$—, —$NR_{11}C(=O)O$—, —$ONR_{11}C(=O)$—, —$ONR_{11}C(=O)O$—, —$ONR_{11}C(=O)NR_{11}$—, —$OC(=O)O$—, —$N(R_{11})C(=O)N(R_{11})$—, —$N(R_{11})C(=S)N(R_{11})$—, —$N(R_{11})S(O)_2N(R_{11})$—, —$N(R_{11})S(O)_2$—, —$N(R_{11})S(O)N(R_{11})$—, —$N(R_{11})S(O)$—, —$C(=NR_{11})$—, —$C(=O)$—, —$C(=O)N(R_{11})$—, and —$C(=S)N(R_{11})$—;
$R_{11}$ is H or $R_2$;
L is a diradical linker selected from a bond, $C_1$-$C_{20}$ alkylene, $C_2$-$C_{20}$ alkenylene, $C_2$-$C_{20}$ alkynylene, $C_3$-$C_8$ cycloalkylene, arylene, aryloxy arylene, heteroarylene, or any combination thereof, which may optionally contain a N, O, S, P, or Si atom; and
wherein said linker may optionally be substituted with one or more groups selected from cyano, nitro, hydroxy, halogen, O, N, S, $C_1$-$C_6$ alkyl, $C_3$-$C_8$ cycloalkyl, $C_1$-$C_6$ alkoxy, $C_1$-$C_6$ thioalkyl, oxo, oximino, and alkoxyimino;
m and n are independently 0, 1, or 2; and
p is 1-3; wherein $R_9$ and $R_{10}$ may be connected to any two atoms of linker L.

1. The compound of paragraph 1 wherein:
A and B are both double bonds; and
n and m are 2.

2. The compound of paragraph 1 wherein:
A and B are both single bonds; and
n and m are 2.

3. The compound of paragraph 1, wherein $R_3$ and $R_7$ are independently hydroxyl or methoxy; and $R_2$ and $R_6$ are independently sec-butyl or iso-propyl.

4. The compound of paragraph 1, wherein $R_1$ and $R_5$ are independently hydrogen or hydroxyl.

5. The compound of paragraph 1 wherein L is $C_1$-$C_{20}$alkylene or arylene; and $R_9$ and $R_{10}$ are independently O, $NR_{11}$, —$NR_{11}C(=O)$—, —$NR_{11}C(=O)O$—, —$ONR_{11}C(=O)$—, —$ONR_{11}C(=O)O$—, —$ONR_{11}C(=O)NR_{11}$—, —$OC(=O)O$—, —$N(R_{11})C(=O)N(R_{11})$—, or —$N(R_{11})S(O)_2$—, —$N(R_{11})S(O)N(R_{11})$—.

6. The compound of paragraph 1 wherein:
$R_1$ and $R_5$ are independently hydrogen or hydroxyl;
$R_2$ and $R_6$ are independently sec-butyl, iso-propyl or cyclohexyl;
$R_3$ and $R_7$ are hydroxyl, methoxy or hydroximino;
$R_4$ and $R_8$ are hydrogen;
$R_9$ and $R_{10}$ are independently nitrogen or oxygen; and
L is $C_2$-$C_{20}$ alkylene or arylene; and
m and n are independently 0 or 2.

7. The compound of paragraph 1 wherein:
$R_1$ and $R_5$ are independently hydrogen or hydroxyl;
$R_2$ and $R_6$ are independently sec-butyl, iso-propyl or cyclohexyl;
$R_3$ and $R_7$ are hydroxyl, methoxy or hydroximino;
$R_4$ and $R_8$ are hydrogen;
$R_9$ and $R_{10}$ are independently —$NR_{11}C(=O)$—, —$NR_{11}C(=O)O$—, —$ONR_{11}C(=O)$—, —$ONR_{11}C(=O)O$—, —$ONR_{11}C(=O)NR_{11}$—, —$OC(=O)O$—, —$N(R_{11})C(=O)N(R_{11})$—, or —$N(R_{11}S(O)_2$—, —$N(R_{11})S(O)N(R_{11})$—; and
L is $C_2$-$C_{20}$ alkylene or arylene; and
m and n are independently 0 or 2

8. The compound of paragraph 1 wherein:
A is a double bond;
B is a double bond;
$R_1$ and $R_5$ are hydrogen;
$R_2$ and $R_6$ are independently isopropyl or sec-butyl;
$R_3$ and $R_7$ are hydroxyl or methoxy;
$R_4$ and $R_8$ are hydrogen;
$R_9$ and $R_{10}$ are independently oxygen or $NR_{11}$; and
L is $C_2$-$C_{10}$ alkylene or arylene.

9. The compound of paragraph 1 wherein:
A is a double bond;
B is a double bond;
$R_1$ and $R_5$ are hydrogen;

$R_2$ and $R_6$ are independently iso-propyl or sec-butyl;
$R_3$ and $R_7$ are hydroxyl, methoxy or hydroxyimino;
$R_4$ and $R_8$ are hydrogen;
$R_9$ and $R_{10}$ are independently —$NR_{11}C(=O)$—, —$NR_{11}C(=O)O$—, —$ONR_{11}C(=O)$—, —$ONR_{11}C(=O)O$—, —$ONR_{11}C(=O)NR_{11}$—, —$N(R_{11})C(=O)N(R_{11})$—, or —$N(R_{11}S(O)_2$—; and
L is $C_2$-$C_{10}$ alkylene or arylene.

10. The compound of paragraph 1 wherein:
A is a single bond;
B is a single bond;
$R_1$ and $R_5$ are hydrogen;
$R_2$ and $R_6$ are independently iso-propyl or sec-butyl;
$R_3$ and $R_7$ are hydroxyl, methoxy or hydroximino;
$R_4$ and $R_8$ are hydrogen;
$R_9$ and $R_{10}$ are independently —$NR_{11}C(=O)$—, —$NR_{11}C(=O)O$—, —$ONR_{11}C(=O)$—, —$ONR_{11}C(=O)O$—, —$ONR_{11}C(=O)NR_{11}$—, —$N(R_{11})C(=O)N(R_{11})$—, or —$N(R_{11}S(O)_2$—; and
L is $C_2$-$C_{10}$ alkylene or arylene.

11. The compound of paragraph 10 or 11 wherein:
$R_3$ and $R_7$ are hydroxyl;
$R_9$ and $R_{10}$ are independently —$NR_{11}C(=O)$—, —$NR_{11}C(=O)O$—, —$ONR_{11}C(=O)$—, —$ONR_{11}C(=O)O$—, —$ONR_{11}C(=O)NR_{11}$—, or —$N(R_{11})C(=O)N(R_{11})$—; and
L is $C_2$-$C_{10}$ alkylene.

12. The compound of paragraph 10 or 11 wherein:
$R_3$ and $R_7$ are hydroxyl;
$R_9$ and $R_{10}$ are independently —$NR_{11}C(=O)$—, —$NR_{11}C(=O)O$—, —$ONR_{11}C(=O)$—, —$ONR_{11}C(=O)O$—, —$ONR_{11}C(=O)NR_{11}$—, or —$N(R_{11})C(=O)N(R_{11})$—; and
L is phenylene.

13. The compound of paragraph 12, wherein:
$R_9$ and $R_{10}$ are independently —$ONR_{11}C(=O)$—, —$ONR_{11}C(=O)O$—, —$ONR_{11}C(=O)NR_{11}$—, or —$N(R_{11})C(=O)N(R_{11})$—;
$R_{11}$ is hydrogen or $C_1$-$C_8$ alkyl; and
m and n are 2.

14. The compound of paragraph 12, wherein:
$R_9$ and $R_{10}$ are independently —$ONR_{11}C(=O)$—, —$ONR_{11}C(=O)O$—, —$ONR_{11}C(=O)NR_{11}$—, or —$N(R_{11})C(=O)N(R_{11})$—;
$R_{11}$ is hydrogen or $C_1$-$C_8$ alkyl; and
m and n are 0.

15. The compound of paragraph 13, wherein:
$R_9$ and $R_{10}$ are independently —$ONR_{11}C(=O)$—, —$ONR_{11}C(=O)O$—, —$ONR_{11}C(=O)NR_{11}$—, or —$N(R_{11})C(=O)N(R_{11})$—;
$R_{11}$ is hydrogen or $C_1$-$C_8$ alkyl; and
m and n are 2.

16. The compound of paragraph 13, wherein:
$R_9$ and $R_{10}$ are independently —$ONR_{11}C(=O)$—, —$ONR_{11}C(=O)O$—, —$ONR_{11}C(=O)NR_{11}$—, or —$N(R_{11})C(=O)N(R_{11})$—;
$R_{11}$ is hydrogen or $C_1$-$C_8$ alkyl; and
m and n are 0.

17. A composition for the treatment or prevention of a parasitic infection in an animal comprising at least one compound of paragraph 1, or a pharmaceutically acceptable salt thereof, and a pharmaceutically acceptable carrier.

18. A composition for combating pests in plants or plant propagation material comprising at least one compound of paragraph 1, or an agriculturally acceptable salt thereof, and an agriculturally acceptable carrier.

19. A method for treating or preventing a parasitic infection or infestation in an animal comprising administering an effective amount of the compound of paragraph 1, or a pharmaceutically acceptable salt thereof, to the animal in need thereof.

20. A method for treating or preventing a parasitic infection or infestation in an animal comprising administering an effective amount of the compound of paragraph 1, or a pharmaceutically acceptable salt thereof, to the animal in need thereof.

21. A method for combating or controlling pests on growing plants, plant propagation material, wood-containing material, or material derived from wood comprising contacting the pests, plants, plant propagation material, or the soil or water in which the plants is growing, or the wood-containing material or material derived from wood, with a pesticidally effective amount of a compound of formula (I), or an agriculturally acceptable salt thereof.

22. Use of the compound of paragraph 1 in the treatment or prevention of a parasitic infection or infestation in an animal.

23. Use of the compound of paragraph 1 in the manufacture of a medicament for the treatment or prevention of a parasitic infection or infestation in an animal.

Having thus described in detail the preferred embodiments of the present invention, it is to be understood that the above description of the invention is intended to be illustrative and not limited to particular details set forth in the above description, as many apparent variations thereof are possible. Various changes or modifications in the embodiment described may occur to those skilled in the art. These variations, changes and modifications can be made without departing from the scope or spirit of the invention.

What is claimed is:

1. A compound of formula (I) or a pharmaceutically acceptable salt thereof:

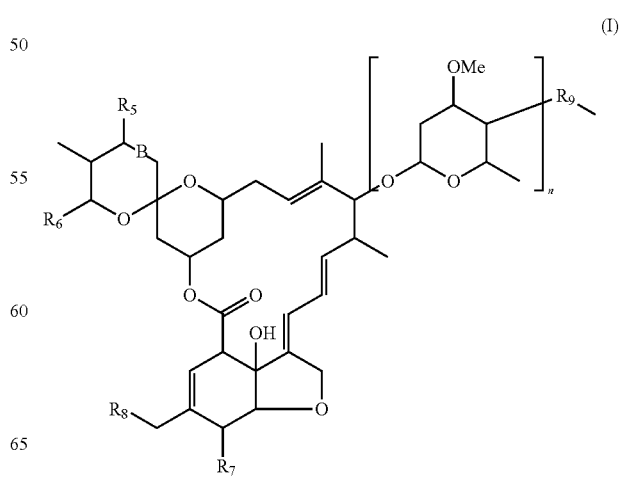

-continued

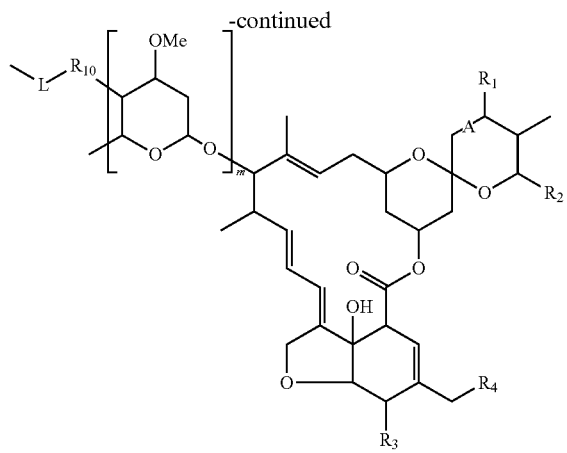

wherein:
A is a single or double bond;
B is a single or double bond;
$R_1$ and $R_5$ are independently hydrogen, hydroxyl, oxo, oximino or alkoxyimino, provided that $R_1$ is hydroxyl only when A is a single bond, and that $R_5$ is hydroxyl only when B is a single bond;
$R_2$ and $R_6$ are independently linear or branched $C_1$-$C_8$ alkyl, $C_2$-$C_8$ alkenyl, or $C_3$-$C_8$ cycloalkyl;
$R_3$ and $R_7$ are independently hydroxyl, methoxy, oxo, hydroximino, or alkoxyimino;
$R_4$ and $R_8$ are independently hydrogen, hydroxyl, $C_1$-$C_8$ alkanoyloxy, benzoyloxy, di-$C_1$-$C_8$ alkylamino benzoyloxy, ($C_1$-$C_8$ alkoxy)$_p$, $C_1$-$C_8$ alkylthio, $C_1$-$C_8$ alkylthioalkoxy or oleandrosyloxy;
$R_9$ and $R_{10}$ are independently diradical groups selected from a bond, O, $NR_{11}$, —$NR_{11}C(=O)$—, —$NR_{11}C(=S)$—, —$NR_{11}C(=O)O$—, —$ONR_{11}C(=O)$—, —$ONR_{11}C(=O)O$—, —$ONR_{11}C(=O)NR_{11}$—, —$OC(=O)O$—, —$N(R_{11})C(=O)N(R_{11})$—, —$N(R_{11})C(=S)N(R_{11})$—, —$N(R_{11})S(O)_2N(R_{11})$—, —$N(R_{11})S(O)_2$—, —$N(R_{11})S(O)N(R_{11})$—, —$N(R_{11})S(O)$—, —$C(=NR_{11})$—, —$C(=O)$—, —$C(=O)N(R_{11})$—, and —$C(=S)N(R_{11})$—;
$R_{11}$ is H or $R_2$;
L is a diradical linker selected from a bond, $C_1$-$C_{20}$ alkylene, $C_2$-$C_{20}$ alkenylene, $C_2$-$C_{20}$ alkynylene, $C_3$-$C_8$ cycloalkylene, arylene, aryloxy arylene, heteroarylene, or any combination thereof, which may optionally contain a N, O, S, P, or Si atom; and
wherein said linker may optionally be substituted with one or more groups selected from cyano, nitro, hydroxy, halogen, O, N, S, $C_1$-$C_6$ alkyl, $C_3$-$C_8$ cycloalkyl, $C_1$-$C_6$ alkoxy, $C_1$-$C_6$ thioalkyl, oxo, oximino, and alkoxyimino;
m and n are independently 1, or 2; and
p is 1-3; wherein $R_9$ and $R_{10}$ may be connected to any two atoms of linker L.

2. The compound of claim 1 wherein:
A and B are both double bonds; and
n and m are 2.

3. The compound of claim 1 wherein:
A and B are both single bonds; and
n and m are 2.

4. The compound of claim 1, wherein $R_3$ and $R_7$ are independently hydroxyl or methoxy; and $R_2$ and $R_6$ are independently sec-butyl or iso-propyl.

5. The compound of claim 1, wherein $R_1$ and $R_5$ are independently hydrogen or hydroxyl.

6. The compound of claim 1 wherein L is $C_1$-$C_{20}$ alkylene or arylene;
and $R_9$ and $R_{10}$ are independently O, $NR_{11}$, —$NR_{11}C(=O)$—, —$NR_{11}C(=O)O$—, —$ONR_{11}C(=O)$—, —$ONR_{11}C(=O)O$—, —$ONR_{11}C(=O)NR_{11}$—, —$OC(=O)O$—, —$N(R_{11})C(=O)N(R_{11})$—, —$N(R_{11})S(O)_2$—, or —$N(R_{11})S(O)N(R_{11})$—.

7. The compound of claim 1 wherein:
$R_1$ and $R_5$ are independently hydrogen or hydroxyl;
$R_2$ and $R_6$ are independently sec-butyl, iso-propyl or cyclohexyl;
$R_3$ and $R_7$ are hydroxyl, methoxy or hydroximino;
$R_4$ and $R_8$ are hydrogen;
$R_9$ and $R_{10}$ are independently nitrogen or oxygen; and
L is $C_2$-$C_{20}$ alkylene or arylene; and
m and n are independently 2.

8. The compound of claim 1 wherein:
$R_1$ and $R_5$ are independently hydrogen or hydroxyl;
$R_2$ and $R_6$ are independently sec-butyl, iso-propyl or cyclohexyl;
$R_3$ and $R_7$ are hydroxyl, methoxy or hydroximino;
$R_4$ and $R_8$ are hydrogen;
$R_9$ and $R_{10}$ are independently —$NR_{11}C(=O)$—, —$NR_{11}C(=O)O$—, —$ONR_{11}C(=O)$—, —$ONR_{11}C(=O)O$—, —$ONR_{11}C(=O)NR_{11}$—, —$OC(=O)O$—, —$N(R_{11})C(=O)N(R_{11})$—, —$N(R_{11})S(O)_2$—, or —$N(R_{11})S(O)N(R_{11})$—; and
L is $C_2$-$C_{20}$ alkylene or arylene; and
m and n are independently 2.

9. The compound of claim 1 wherein:
A is a double bond;
B is a double bond;
$R_1$ and $R_5$ are hydrogen;
$R_2$ and $R_6$ are independently isopropyl or sec-butyl;
$R_3$ and $R_7$ are hydroxyl or methoxy;
$R_4$ and $R_8$ are hydrogen;
$R_9$ and $R_{10}$ are independently oxygen or $NR_{11}$; and
L is $C_2$-$C_{10}$ alkylene or arylene.

10. The compound of claim 1 wherein:
A is a double bond;
B is a double bond;
$R_1$ and $R_5$ are hydrogen;
$R_2$ and $R_6$ are independently iso-propyl or sec-butyl;
$R_3$ and $R_7$ are hydroxyl, methoxy or hydroxyimino;
$R_4$ and $R_8$ are hydrogen;
$R_9$ and $R_{10}$ are independently —$NR_{11}C(=O)$—, —$NR_{11}C(=O)O$—, —$ONR_{11}C(=O)$—, —$ONR_{11}C(=O)O$—, —$ONR_{11}C(=O)NR_{11}$—, —$N(R_{11})C(=O)N(R_{11})$—, or —$N(R_{11})S(O)_2$—; and
L is $C_2$-$C_{10}$ alkylene or arylene.

11. The compound of claim 1 wherein:
A is a single bond;
B is a single bond;
$R_1$ and $R_5$ are hydrogen;
$R_2$ and $R_6$ are independently iso-propyl or sec-butyl;
$R_3$ and $R_7$ are hydroxyl, methoxy or hydroximino;
$R_4$ and $R_8$ are hydrogen;
$R_9$ and $R_{10}$ are independently —$NR_{11}C(=O)$—, —$NR_{11}C(=O)O$—, —$ONR_{11}C(=O)$—, —$ONR_{11}C(=O)O$—, —$ONR_{11}C(=O)NR_{11}$—, —$N(R_{11})C(=O)N(R_{11})$—, or —$N(R_{11})S(O)_2$—; and
L is $C_2$-$C_{10}$ alkylene or arylene.

12. The compound of claim 10 or 11 wherein:
$R_3$ and $R_7$ are hydroxyl;
$R_9$ and $R_{10}$ are independently —$NR_{11}C(=O)$—, —$NR_{11}C(=O)O$—, —$ONR_{11}C(=O)$—, —$ONR_{11}C(=O)O$—, —$ONR_{11}C(=O)NR_{11}$—, or —$N(R_{11})C(=O)N(R_{11})$—; and
L is $C_2$-$C_{10}$ alkylene.

13. The compound of claim 10 or 11 wherein:
$R_3$ and $R_7$ are hydroxyl;
$R_9$ and $R_{10}$ are independently —$NR_{11}C(=O)$—, —$NR_{11}C(=O)O$—, —$ONR_{11}C(=O)$—, —$ONR_{11}C(=O)O$—, —$ONR_{11}C(=O)NR_{11}$—, or —$N(R_{11})C(=O)N(R_{11})$—; and
L is phenylene.

14. The compound of claim 12, wherein:
$R_9$ and $R_{10}$ are independently —$ONR_{11}C(=O)$—, —$ONR_{11}C(=O)O$—, —$ONR_{11}C(=O)NR_{11}$—, or —$N(R_{11})C(=O)N(R_{11})$—;
$R_{11}$ is hydrogen or $C_1$-$C_8$ alkyl; and
m and n are 2.

15. The compound of claim 12, wherein:
$R_9$ and $R_{10}$ are independently —$ONR_{11}C(=O)$—, —$ONR_{11}C(=O)O$—, —$ONR_{11}C(=O)NR_{11}$—, or —$N(R_{11})C(=O)N(R_{11})$—;
$R_{11}$ is hydrogen or $C_1$-$C_8$ alkyl; and
m and n are 0.

16. The compound of claim 13, wherein:
$R_9$ and $R_{10}$ are independently —$ONR_{11}C(=O)$—, —$ONR_{11}C(=O)O$—, —$ONR_{11}C(=O)NR_{11}$—, or —$N(R_{11})C(=O)N(R_{11})$—;
$R_{11}$ is hydrogen or $C_1$-$C_8$ alkyl; and
m and n are 2.

17. A composition for the treatment of a parasitic infection in an animal comprising at least one compound of claim 1, or a pharmaceutically acceptable salt thereof, and a pharmaceutically acceptable carrier.

18. A composition for combating pests in plants or plant propagation material comprising at least one compound of claim 1, or an agriculturally acceptable salt thereof, and an agriculturally acceptable carrier.

19. A method for treating an endoparasitic infection in an animal comprising administering an effective amount of the compound of claim 1, or a pharmaceutically acceptable salt thereof, to an animal in need thereof, wherein said endoparasitic infection is caused by an endoparasite selected from the group consisting of *Anaplocephala, Ancylostoma, Anecator, Ascaaris, Capillaria, Cooperia, Dipylidium, Dirofilaria, Echinococcus, Enterobius, Fasciola, Haemonchus, Oesophagostumum, Ostertagia, Toxocara, Strongyloides, Toxascaris, Trichinella, Trichuris* and *Trichostrongylus*.

* * * * *